US011492617B2

(12) United States Patent
Bennett et al.

(10) Patent No.: US 11,492,617 B2
(45) Date of Patent: Nov. 8, 2022

(54) COMPOSITIONS AND METHODS FOR MODULATION OF PROTEIN AGGREGATION

(71) Applicant: Ionis Pharmaceuticals, Inc., Carlsbad, CA (US)

(72) Inventors: C. Frank Bennett, Carlsbad, CA (US); Xue-hai Liang, Del Mar, CA (US); Wen Shen, Carlsbad, CA (US)

(73) Assignee: Ionis Pharmaceuticals, Inc, Carlsbad, CA (US)

( * ) Notice: Subject to any disclaimer, the term of this patent is extended or adjusted under 35 U.S.C. 154(b) by 55 days.

(21) Appl. No.: 16/636,485

(22) PCT Filed: Aug. 7, 2018

(86) PCT No.: PCT/US2018/045660
§ 371 (c)(1),
(2) Date: Feb. 4, 2020

(87) PCT Pub. No.: WO2019/032613
PCT Pub. Date: Feb. 14, 2019

(65) Prior Publication Data

US 2020/0239888 A1 Jul. 30, 2020

Related U.S. Application Data

(60) Provisional application No. 62/542,730, filed on Aug. 8, 2017.

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/315* (2013.01); *C12N 2310/32* (2013.01); *C12N 2310/341* (2013.01); *C12N 2310/346* (2013.01)

(58) Field of Classification Search
None
See application file for complete search history.

(56) References Cited

U.S. PATENT DOCUMENTS

| | | | | |
|---|---|---|---|---|
| 2003/0072794 A1 | | 4/2003 | Boulikas | |
| 2015/0087691 A1* | | 3/2015 | Monia | C12N 15/113 514/44 A |
| 2018/0216113 A1* | | 8/2018 | Dillin | A61K 31/4458 |

FOREIGN PATENT DOCUMENTS

WO WO 2004/014306 2/2004

OTHER PUBLICATIONS

Aulas et al., "Alterations in stress granule dynamics driven by TDP-43 and FUS: a link to pathological inclusions in ALS?" Front Cell Neurosci (2015) 9: 1-13.

Bailey et al., "Nucleic acid binding proteins affect the subcellular distribution of phosphorothioate antisense oligonucleotides" Nuc Ac Res (2017) 45: 10649-10671.

Bolte et al. "A guided tour into subcellular colocalization analysis in light microscopy" J Microsc (2006) 224: 213-232.

Crooke et al. "Cellular uptake and trafficking of antisense oligonucleotides" Nature Biotech (2017) 35: 230-237.

Dormann et al. "Arginine methylation next to the PY-NLS modulates Transportin binding and nuclear import of FUS" EMBO J (2012) 31: 4258-4275.

International Search Report for PCT/US18/045660 dated Nov. 2, 2018.

King et al. "The tip of the iceberg: RNA-binding proteins with prion-like domains in neurodegenerative disease" Brain Res (2012) 1462: 61-80.

Li et al. "Stress granules as crucibles of ALS pathogenesis" J Cell Biol (2013) 201: 361-372.

Liang et al., "Rnase H1-Dependent Antisense Oligonucleotides Are Robustly Active in Directing RNA Cleavage in Both the Cytoplasm and the Nucleus" Mol Ther (2017) 25: 2075-2092.

Maziuk et al. "Dysregulation of RNA Binding Protein Aggregation in Neurodegenerative Disorders" Front Mol Neurosci (2017) 10: 1-9.

Ramaswami et al. "Altered ribostasis: RNA-protein granules in degenerative disorders" Cell (2013) 154: 727-736.

Schindelin et al. "Fiji: an open-source platform for bio logical-image analysis" Nat Methods (2012) 9: 676-682.

Seyfried et al. "Quantitative analysis of the detergent-insoluble brain proteome in frontotemporal lobar degeneration using SILAC internal standards" J Proteome Res (2012) 11: 2721-2738.

Shang et al. "Mechanisms of FUS mutations in familial amyotrophic lateral sclerosis" Brain Res (2016) 1647: 65-78.

Shelkovnikova et al. "Multistep process of FUS aggregation in the cell cytoplasm involves RNA-dependent and RNA-independent mechanisms" Hum Mol Genet (2014) 23: 5211-5226.

Shelkovninkova et al. "Fused in sarcoma (FUS) protein lacking nuclear localization signal (NLS) and major RNA binding motifs triggers proteinopathy and severe motor phenotype in transgenic mice" J Biol Chem (2013) 288: 25266-25274.

(Continued)

*Primary Examiner* — Kimberly Chong
(74) *Attorney, Agent, or Firm* — McNeill Baur PLLC

(57) ABSTRACT

In certain embodiments, the present disclosure provides methods comprising contacting a cell with a compound comprising a modified oligonucleotide complementary to a nucleic acid transcript. In certain such embodiments, the modified oligonucleotide does not interact or interacts poorly with a mRNP complex or granule. In certain such embodiments the modifications and/or motifs of the modified oligonucleotide do not promote interaction with a mRNP complex or granule. In certain embodiments, the present disclosure provides methods comprising contacting a cell with a compound comprising a modified oligonucleotide thereby reducing the size or amount of protein aggregation in the cell. In certain such embodiments, the protein aggregate is a mRNP granule. In certain such embodiments, the modifications and/or motifs of the modified oligonucleotide promote interaction with a protein aggregate, such as a mRNP granule, that results in disruption of the protein aggregate.

23 Claims, No Drawings

Specification includes a Sequence Listing.

(56) References Cited

OTHER PUBLICATIONS

Vickers et al. "Development of a Quantitative BRET Affinity Assay for Nucleic Acid-Protein Interactions" PLOS One (2016) 11(8): 1-17.

Xiang et al. "The LC Domain of hnRNPA2 Adopts Similar Conformations in Hydrogel Polymers, Liquid-like Droplets, and Nuclei" Cell (2015) 163: 829-839.

Zhang et al. "Structural and energetic basis of ALS-causing mutations in the atypical proline-tyrosine nuclear localization signal of the Fused in Sarcoma protein (FUS)" Proc Natl Acad Sci USA (2012) 109: 12017-12021.

* cited by examiner

COMPOSITIONS AND METHODS FOR MODULATION OF PROTEIN AGGREGATION

SEQUENCE LISTING

The present application is being filed along with a Sequence Listing in electronic format. The Sequence Listing is provided as a file entitled CORE0144USASEQ_ST25.txt, created Feb. 3, 2020, which is 144 Kb in size. The information in the electronic format of the sequence listing is incorporated herein by reference in its entirety.

BACKGROUND

Protein aggregates, such as mRNP granules, are present in cells of patients with ALS, Parkinsons's Disease, and some forms of dementia, as well as other diseases. (See, e.g., Li et al. *J Cell Biol,* 201, 361-372 (2013); Seyfried et al. *J Proteome Res,* 11, 2721-2738 (2012); Ramaswami et al. *Cell,* 154, 727-736 (2013); Aulas and Vande Velde. *Front Cell Neurosci,* 9, 423 (2015); Shelkovnikova et al. *Hum Mol Genet,* 23, 5211-5226 (20140); and King et al. *Brain Res,* 1462, 61-80 (2012).) FUS/TLS (Fused in Sarcoma/Translocated in Sarcoma) and PSF/SFPQ (Polypyrimidine-Tract Binding Protein-Associated Splicing Factor/Splicing Factor Proline/Glutamine Rich) are ubiquitously expressed RNA-binding proteins with multifunctional roles in RNA metabolism. Both proteins contain prion-like, low complexity domains (LCD) that can facilitate aggregation. (See, e.g., Maziuk et al. *Front Mol Neurosci* 10, (2017); Xiang et al. *Cell,* 163, 829-839 (2015).)

Wild type FUS contains a PY-nuclear localization sequence (NLS). Some FUS mutants that disrupt the NLS lead to cytoplasmic accumulation and aggregation of FUS into cytoplasmic granules. (See, e.g., Shang and Huang. *Brain Res,* 1647, 65-78 (2016); Dormann et al. *EMBO J,* 31, 4258-4275 (2012); Zhang and Chook *Proc Natl Acad Sci USA,* 109, 12017-12021 (2012); Shelkovnikova et al. *J Biol Chem,* 288, 25266-25274 (2013).) In vitro, cytoplasmic FUS granules can be formed from the expression of a FUS mutant having a P525L mutation that is naturally occurring in some ALS patients.

SUMMARY OF THE INVENTION

Modified oligonucleotides can interact with proteins, including mRNP complexes or granules and/or proteins associated with mRNP complexes or granules. Such interactions may not be beneficial when the mRNP complex or granule sequesters the modified oligonucleotide in the cytoplasm, and the target of the modified oligonucleotide is located in the nucleus. Such interactions may be beneficial when aggregation of a mRNP granule is modulated, e.g., disrupted by the modified oligonucleotide. In certain embodiments, the present disclosure provides methods comprising contacting a cell with a compound comprising a modified oligonucleotide complementary to a nucleic acid transcript. In certain such embodiments, the modified oligonucleotide does not interact or interacts poorly with a mRNP complex or granule. In certain such embodiments the modifications and/or motifs of the modified oligonucleotide do not promote interaction with a mRNP complex or granule. In certain embodiments, the present disclosure provides methods comprising contacting a cell with a compound comprising a modified oligonucleotide thereby reducing the size or amount of protein aggregation in the cell. In certain such embodiments, the protein aggregate is a mRNP granule. In certain such embodiments, the modifications and/or motifs of the modified oligonucleotide promote interaction with a protein aggregate, such as a mRNP granule, that results in disruption of the protein aggregate.

DETAILED DESCRIPTION OF THE INVENTION

Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described.

Definitions

As used herein, "2'-deoxynucleoside" means a nucleoside comprising 2'-H(H) ribosyl sugar moiety, as found in naturally occurring deoxyribonucleic acids (DNA). In certain embodiments, a 2'-deoxynucleoside may comprise a modified nucleobase or may comprise an RNA nucleobase (uracil).

As used herein, "2'-fluoro" or "2'-F" means a 2'-F in place of the 2'-OH group of a ribosyl ring of a sugar moiety.

As used herein, "2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

As used herein, "ALS" means amyotrophic lateral sclerosis.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means a compound comprising an antisense oligonucleotide and optionally one or more additional features, such as a conjugate group or terminal group.

As used herein, "antisense oligonucleotide" means an oligonucleotide having a nucleobase sequence that is at least partially complementary to a target nucleic acid.

As used herein, "ameliorate" in reference to a method means improvement in at least one symptom and/or measurable outcome relative to the same symptom or measurable outcome in the absence of or prior to performing the method. In certain embodiments, amelioration is the reduction in the severity or frequency of a symptom or the delayed onset or slowing of progression in the severity or frequency of a symptom and/or disease.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

As used herein, “cEt” or “constrained ethyl” means a ribosyl bicyclic sugar moiety wherein the second ring of the bicyclic sugar is formed via a bridge connecting the 4'-carbon and the 2'-carbon, wherein the bridge has the formula 4'-$CH(CH_3)$—O-2', and wherein the methyl group of the bridge is in the S configuration.

As used herein, “cleavable moiety” means a bond or group of atoms that is cleaved under physiological conditions, for example, inside a cell, an animal, or a human.

As used herein, “complementary” in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include adenine (A) and thymine (T), adenine (A) and uracil (U), cytosine (C) and guanine (G), 5-methyl cytosine ($^{m}$C) and guanine (G). Complementary oligonucleotides and/or nucleic acids need not have nucleobase complementarity at each nucleoside. Rather, some mismatches are tolerated. As used herein, “fully complementary” or “100% complementary” in reference to oligonucleotides means that such oligonucleotides are complementary to another oligonucleotide or nucleic acid at each nucleoside of the oligonucleotide.

As used herein, “conjugate group” means a group of atoms that is directly or indirectly attached to an oligonucleotide. Conjugate groups include a conjugate moiety and a conjugate linker that attaches the conjugate moiety to the oligonucleotide.

As used herein, “conjugate linker” means a group of atoms comprising at least one bond that connects a conjugate moiety to an oligonucleotide.

As used herein, “conjugate moiety” means a group of atoms that is attached to an oligonucleotide via a conjugate linker.

As used herein, “contiguous” in the context of an oligonucleotide refers to nucleosides, nucleobases, sugar moieties, or internucleoside linkages that are immediately adjacent to each other. For example, “contiguous nucleobases” means nucleobases that are immediately adjacent to each other in a sequence.

As used herein, “double-stranded antisense compound” means an antisense compound comprising two oligomeric compounds that are complementary to each other and form a duplex, and wherein one of the two said oligomeric compounds comprises an antisense oligonucleotide.

As used herein, “expanded repeat” in reference to a transcript or protein means a portion of a transcript or protein having a repeat region that has more repeats or repetitive elements than the corresponding repeat region of the corresponding wild type transcript or protein such that the number of repeats or repetitive elements in an “expanded repeat” transcript or protein is associated with a disease.

As used herein, “fully modified” in reference to a modified oligonucleotide means a modified oligonucleotide in which each sugar moiety is modified. “Uniformly modified” in reference to a modified oligonucleotide means a fully modified oligonucleotide in which each sugar moiety is the same. For example, the nucleosides of a uniformly modified oligonucleotide can each have a 2'-MOE modification but different nucleobase modifications, and the internucleoside linkages may be different.

As used herein, “FUS” means a FUS or TLS gene or a transcript or protein encoded by a FUS gene.

As used herein, “G3BP” means a G3BP stress granule assembly factor 1 gene or a transcript or protein encoded by a G3BP stress granule assembly factor 1 gene.

As used herein, “gapmer” means an antisense oligonucleotide comprising an internal “gap” region having a plurality of nucleosides that support RNase H cleavage positioned between external “wing” regions having one or more nucleosides, wherein the nucleosides comprising the internal region are chemically distinct from the nucleoside or nucleosides comprising the external regions.

As used herein, “hybridization” means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, “inhibiting formation” in reference to protein aggregates refers to a blockade or partial blockade of new protein aggregate formation and does not necessarily indicate a total elimination of new protein aggregate formation.

As used herein, the terms “internucleoside linkage” means a group or bond that forms a covalent linkage between adjacent nucleosides in an oligonucleotide. As used herein “modified internucleoside linkage” means any internucleoside linkage other than a naturally occurring, phosphate internucleoside linkage. Non-phosphate linkages are referred to herein as modified internucleoside linkages. “Phosphorothioate linkage” means a modified phosphate linkage in which one of the non-bridging oxygen atoms is replaced with a sulfur atom. A phosphorothioate internucleoside linkage is a modified internucleoside linkage. Modified internucleoside linkages include linkages that comprise abasic nucleosides. As used herein, “abasic nucleoside” means a sugar moiety in an oligonucleotide or oligomeric compound that is not directly connected to a nucleobase. In certain embodiments, an abasic nucleoside is adjacent to one or two nucleosides in an oligonucleotide.

As used herein, “linker-nucleoside” means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, “low complexity domain” means a domain of a protein that is intrinsically disordered or lacking tertiary structure and comprises a low complexity sequence containing repeats of single amino acids or short amino acid motifs. In certain embodiments, low complexity domains are prio-like domains.

As used herein, “non-bicyclic modified sugar” or “non-bicyclic modified sugar moiety” means a modified sugar moiety that comprises a modification, such as a substitutent, that does not form a bridge between two atoms of the sugar to form a second ring.

As used herein, “linked nucleosides” are nucleosides that are connected in a continuous sequence (i.e. no additional nucleosides are present between those that are linked).

As used herein, “liquid miscibility” in reference to a protein or protein aggregate means the extent to which the protein or protein aggregate can mix with a liquid, as opposed to phase separate from said liquid. In certain embodiments, an increase in liquid miscibility of a protein or protein aggregate means that the protein or protein aggregate forms a more homogeneous mixture in the cytoplasm and decreases the extent to which it phase separates from the cytoplasm. In certain embodiments, an increase in liquid miscibility comprises an increase in water solubility.

As used herein, "messenger ribonucleoprotein complex" or "mRNP complex" means mRNA bound with proteins. As used herein, "messenger ribonucleoprotein granule" or "mRNP granule" means a protein aggregate comprising multiple mRNP complexes.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "modulation" means a perturbation of function, formation, activity, size, amount, or localization. Modulation of sub-cellular localization or distribution of a molecule means a change in a ratio of the amount of the molecule in two sub-cellular locations. Modulation of protein aggregation means a change in the function, formation, activity, size, amount, or localization of a protein aggregate or protein aggregates.

As used herein, "MOE" means methoxyethyl. "2'-MOE" means a 2'-$OCH_2CH_2OCH_3$ group in place of the 2'-OH group of a ribosyl ring of a sugar moiety.

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means a naturally occurring nucleobase or a modified nucleobase. As used herein a "naturally occurring nucleobase" is adenine (A), thymine (T), cytosine (C), uracil (U), and guanine (G). As used herein, a modified nucleobase is a group of atoms capable of pairing with at least one naturally occurring nucleobase. A universal base is a nucleobase that can pair with any one of the five unmodified nucleobases. As used herein, "nucleobase sequence" means the order of contiguous nucleobases in a nucleic acid or oligonucleotide independent of any sugar or internucleoside linkage modification.

As used herein, "nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "pharmaceutically acceptable carrier or diluent" means any substance suitable for use in administering to an animal. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the parent compound and do not impart undesired toxicological effects thereto.

As used herein "pharmaceutical composition" means a mixture of substances suitable for administering to a subject. For example, a pharmaceutical composition may comprise an antisense compound and a sterile aqueous solution. In certain embodiments, a pharmaceutical composition shows activity in free uptake assay in certain cell lines.

As used herein, "phosphorus moiety" means a group of atoms comprising a phosphorus atom. In certain embodiments, a phosphorus moiety comprises a mono-, di-, or tri-phosphate, or phosphorothioate.

As used herein, "processing body" means an mRNP granule that comprises RNA and at least one decapping factor or at least one protein that represses translation.

As used herein "prodrug" means a therapeutic agent in a form outside the body that is converted to a different form within the body or cells thereof. Typically conversion of a prodrug within the body is facilitated by the action of an enzymes (e.g., endogenous or viral enzyme) or chemicals present in cells or tissues and/or by physiologic conditions.

As used herein, "protein aggregate" means a complex comprising multiple protein molecules non-covalently bound together. In certain embodiments, protein aggregates comprise oligonucleotides and/or nucleic acids. As used herein, "reducing the size or amount of protein aggregates" means dissociating at least one component of a protein aggregate from the complex and/or reducing the number of protein aggregates present.

As used herein, "PSF" means a SFPQ or PSF gene, or a transcript or protein encoded by a SFPQ or PSF gene.

As used herein, "RAN translation product" or "repeat-associated non-ATG translation product" means a peptide or protein encoded by a portion of an RNA that contains a repeat region and lacks an AUG start codon. In certain embodiments, the repeat region is an expanded repeat.

As used herein, "RNA recognition motif" or "RRM" means a sequence or protein domain comprising at least one of the consensus sequences RNP1 and RNP2.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to a compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex.

As used herein, “standard cell assay” means the assay described in Example X and reasonable variations thereof.

As used herein, “standard in vivo experiment” means the procedure described in Example X and reasonable variations thereof.

As used herein, “stress granule” means an mRNP granule that comprises components of the small ribosomal subunit, translation initiation factors, and/or poly(a)-binding protein. In certain embodiments, stress granules also contain G3BP.

As used herein, “sugar moiety” means an unmodified sugar moiety or a modified sugar moiety. As used herein, “unmodified sugar moiety” means a 2'-OH(H) ribosyl moiety, as found in RNA (an “unmodified RNA sugar moiety”), or a 2'-H(H) moiety, as found in DNA (an “unmodified DNA sugar moiety”). As used herein, “modified sugar moiety” or “modified sugar” means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars. As used herein, “sugar surrogate” means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, “target nucleic acid,” “target RNA,” “target RNA transcript” and “nucleic acid target” mean a nucleic acid that an antisense compound is designed to affect.

As used herein, “target region” means a portion of a target nucleic acid to which an antisense compound is designed to hybridize.

As used herein, “terminal group” means a chemical group or group of atoms that is covalently linked to a terminus of an oligonucleotide.

As used herein, “TDP-43” means a TAR DNA binding protein gene, or a transcript or protein encoded by a TAR DNA binding protein gene.

Certain Embodiments

The present disclosure includes but is not limited to the following embodiments.

Embodiment 1. A method of reducing the size or amount of protein aggregates in a cell comprising: contacting a cell with a compound comprising a modified oligonucleotide, thereby reducing the size or amount of protein aggregates in the cell.

Embodiment 2. A method of inhibiting the formation of protein aggregates in a cell comprising: contacting a cell with a compound comprising a modified oligonucleotide, thereby inhibiting the formation of protein aggregates in the cell.

Embodiment 3. A method of increasing liquid miscibility of a protein in a cell comprising: contacting a cell with a compound comprising a modified oligonucleotide, thereby increasing the liquid miscibility of a protein in the cell.

Embodiment 4. The method of embodiment 3, wherein the protein is in a protein aggregate.

Embodiment 5. The method of embodiment 3, wherein the liquid miscibility of the protein aggregate in the cell is increased.

Embodiment 6. The method of embodiment 4 or 5, wherein the size or amount of protein aggregates in the cell is reduced.

Embodiment 7. A method of modulating the sub-cellular distribution of at least one protein in a cell comprising: contacting a cell with a compound comprising a modified oligonucleotide, thereby modulating the sub-cellular distribution of at least one protein in the cell.

Embodiment 8. The method of embodiment 7, wherein the modulation of sub-cellular distribution of the at least one protein is an increase in the ratio of nuclear to cytoplasmic distribution of the at least one protein.

Embodiment 9. The method of embodiment 7 or 8, wherein the at least one protein is in a protein aggregate.

Embodiment 10. The method of embodiment 9, wherein the size or amount of protein aggregates in the cell is reduced.

Embodiment 11. The method of any of embodiments 1, 2, 4-6, 9, or 10, wherein the protein aggregates are present in the cytoplasm of the cell.

Embodiment 12. The method of embodiment 11, wherein the protein aggregates comprise an RNA-binding protein.

Embodiment 13. The method of embodiment 12, wherein the RNA-binding protein is FUS, TDP-43, or PSF.

Embodiment 14. The method of embodiment 12 or 13, wherein the RNA-binding protein comprises a mutation.

Embodiment 15. The method of embodiment 14, wherein the mutation is a point mutation.

Embodiment 16. The method of embodiment 14, wherein the mutation is an expanded repeat.

Embodiment 17. The method of embodiment 14, wherein the mutation is a deletion.

Embodiment 18. The method of any of embodiments 14-17, wherein the mutation causes protein aggregation, liquid immiscibility, and/or mislocalization of the protein in a cell.

Embodiment 19. The method of any of embodiments 12-18, wherein the RNA-binding protein comprises a low complexity domain.

Embodiment 20. The method of embodiment 19, wherein the modified oligonucleotide binds to the low complexity domain.

Embodiment 21. The method of any of embodiments 12-20, wherein the RNA-binding protein comprises an RNA recognition motif.

Embodiment 22. The method of embodiment 21, wherein the modified oligonucleotide does not bind to the RNA recognition motif.

Embodiment 23. The method of embodiment 21, wherein the modified oligonucleotide binds to the low complexity domain with higher affinity than it binds to the RNA recognition motif.

Embodiment 24. The method of any of embodiments 1-23, wherein the cell comprises a protein comprising an expanded repeat.

Embodiment 25. The method of any of embodiments 1-24, wherein the cell comprises Ran translation products.

Embodiment 26. The method of any of embodiments 1, 2, 4-6, or 9-25, wherein the protein aggregate is a messenger ribonucleoprotein granule.

Embodiment 27. The method of embodiment 26, wherein the protein aggregate is a stress granule Embodiment 28. The method of embodiment 26, wherein the protein aggregate is processing body.

Embodiment 29. The method of any of embodiments 1, 2, 4-6, or 9-28, wherein the protein aggregate comprises G3BP protein.

Embodiment 30. The method of any of embodiments 1-29, wherein the modified oligonucleotide is a gapmer, wherein the gap consists of linked 2'-deoxynucleosides and the wings consist of linked nucleosides comprising modified sugar moieties.

Embodiment 31. The method of any of embodiments 1-30, wherein the modified oligonucleotide comprises at least one modified sugar moiety.

Embodiment 32. The method of embodiment 31, wherein the at least one modified sugar moiety is a cEt modified sugar moiety, a 2'-MOE modified sugar moiety, or a 2'-fluoro modified sugar moiety.

Embodiment 33. The method of embodiment 31, wherein the at least one modified sugar moiety is a 2'-fluoro modified sugar moiety.

Embodiment 34. The method of any of embodiments 1-33, wherein the modified oligonucleotide comprises at least one phosophorothioate internucleoside linkage.

Embodiment 35. The method of embodiment 34, wherein each internucleoside linkage of the modified oligonucleotide is a phosphorothioate internucleoside linkage.

Embodiment 36. The method of any of embodiments 1-35, wherein the modified oligonucleotide comprises at least one modified nucleobase.

Embodiment 37. The method of embodiment 36, wherein the at least one modified nucleobase is a 5'-methyl cytosine.

Embodiment 38. The method of any of embodiments 1-37, wherein the nucleobase sequence of the modified oligonucleotide is not 100% complementary to a pre-mRNA or a mRNA in the cell.

Embodiment 39. The method of any of embodiments 1-38, wherein the compound comprises a conjugate group.

Embodiment 40. The method of any of embodiments 1-39, wherein the protein or protein aggregate is not a prion protein or prion protein aggregate.

Embodiment 41. The method of any of embodiments 1-40, wherein the cell is in an animal.

Embodiment 42. The method of any of embodiments 1-40, wherein the cell is in a human patient.

Embodiment 43. The method of embodiment 42, wherein the patient has a neurodegenerative disease.

Embodiment 44. The method of embodiment 42, wherein the patient has ALS.

Embodiment 45. The method of embodiment 42, wherein the patient has Alzheimer's Disease.

Embodiment 46. The method of embodiment 42, wherein the patient has juvenile onset ALS.

Embodiment 47. The method of embodiment 42, wherein the patient has Parkinson's Disease.

Embodiment 48. The method of embodiment 42, wherein the patient has frontotemporal dementia.

Embodiment 49. The method of embodiment 42, wherein the patient has Pick's Disease.

Embodiment 50. The method of any of embodiments 42-49, wherein at least one symptom in the patient is ameliorated.

Embodiment 51. The method of any of embodiments 42-50, wherein the patient's disease is treated or ameliorated.

Embodiment 52. The method of any of embodiments 1-51, comprising contacting a cell with a second compound comprising a modified oligonucleotide, wherein the second modified oligonucleotide is 100% complementary to a target nucleic acid in the cell.

Embodiment 53. The method of embodiment 52, wherein the target nucleic acid is a pre-mRNA or a mRNA.

Embodiment 54. A modified oligonucleotide for use in treating or ameliorating a neurodegenerative disease in a human in need thereof, wherein the modified oligonucleotide causes a reduction in the size or amount of cytoplasmic protein aggregates in the human.

Embodiment 55. Use of a modified oligonucleotide capable of causing a reduction in the size or amount of cytoplasmic protein aggregates in a cell for treatment of a neurodegenerative disease.

Embodiment 56. The method of any of embodiments 1-37 or 39-51, wherein the nucleobase sequence of the modified oligonucleotide is less than 70% complementary to a pre-mRNA or a mRNA in the cell.

Embodiment 57. A method of screening the sub-cellular distribution of at least one protein in a cell comprising: contacting a cell with a compound comprising a modified oligonucleotide and subsequently detecting the sub-cellular distribution of the at least one protein in the cell.

Embodiment 58. The method of embodiment 57, wherein the detection of the sub-cellular distribution of the at least one protein in the cell comprises contacting the cell with an antibody that binds to the at least one protein.

Embodiment 59. The method of embodiment 57 or 58, comprising contacting the cell with a vector that expresses a fusion protein prior to contacting the cell with the compound, wherein the fusion protein comprises a detectable tag.

Embodiment 60. The method of embodiment 59, wherein the detectable tag is a fluorescent protein.

Embodiment 61. The method of embodiment 59, wherein the detectable tag is an epitope tag.

Embodiment 62. The method of embodiment 60, wherein the fluorescent protein is a green fluorescent protein.

Embodiment 63. The method of any of embodiments 57-62, wherein the at least one protein is an RNA-binding protein.

Embodiment 64. The method of embodiment 63, wherein the RNA-binding protein is FUS, TDP-43, or PSF.

Embodiment 65. The method of embodiment 63 or 64, wherein the RNA-binding protein comprises a mutation.

Embodiment 66. The method of any of embodiments 59-65, wherein the fusion protein comprises FUS, TDP-43, or PSF.

I. Certain Oligonucleotides

In certain embodiments, the invention provides compounds that comprise or consist of oligonucleotides that consist of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 4', and/or 5' positions. In certain embodiments, the furanosyl sugar moiety is a ribosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-$OCH_3$ ("OMe" or "O-methyl"), and 2'-$O(CH_2)_2OCH_3$ ("MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, O—$C_1$-$C_{10}$ alkyl, O—$C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C$(═O)—N($R_m$)($R_n$), where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH{=}CH_2$, $OCH_2CH{=}CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C$(═O)—N($R_m$)($R_n$)), where each $R_m$ and $R_n$ is, independently, H, an amino protecting group, or substituted or unsubstituted $C_1$-$C_{10}$ alkyl.

In certain embodiments, a 2'-substituted nucleoside or 2'-non-bicyclic modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C$(═O)—N(H)$CH_3$ ("NMA").

In certain embodiments, a 2'-substituted nucleoside or 2'-non-bicyclic modified nucleoside comprises a sugar moiety comprising a non-bridging 2'-substituent group selected from: F, $OCH_3$, and $OCH_2CH_2OCH_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of such 4' to 2' bridging sugar substituents include but are not limited to: 4'-$CH_2$-2',4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-CH($CH_3$)—O-2' (referred to as "constrained ethyl" or "cEt" when in the S configuration), 4'-$CH_2$—O—$CH_2$-2', 4'-$CH_2$—N(R)-2', 4'-CH($CH_2OCH_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C($CH_3$)($CH_3$)—O-2' and analogs thereof (see, e.g., Seth et al., U.S. Pat. No. 8,278,283), 4'-$CH_2$—N($OCH_3$)-2' and analogs thereof (see, e.g., Prakash et al., U.S. Pat. No. 8,278,425), 4'-$CH_2$—O—N($CH_3$)-2' (see, e.g., Allerson et al., U.S. Pat. No. 7,696,345 and Allerson et al., U.S. Pat. No. 8,124,745), 4'-$CH_2$—C(H)($CH_3$)-2' (see, e.g., Zhou, et al., *J. Org. Chem.,* 2009, 74, 118-134), 4'-$CH_2$—C(═$CH_2$)-2' and analogs thereof (see e.g., Seth et al., U.S. Pat. No. 8,278,426), 4'-C($R_aR_b$)—N(R)—O-2', 4'-C($R_aR_b$)—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672).

In certain embodiments, such 4' to 2' bridges independently comprise from 1 to 4 linked groups independently selected from: —$[C(R_a)(R_b)]_n$—, —$[C(R_a)(R_b)]_n$—O—, —C($R_a$)═C($R_b$)—, —C($R_a$)═N—, —C(═N$R_a$)—, —C(═O)—, —C(═S)—, —O—, —Si$(R_a)_2$—, —S$(═O)_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl (S$(═O)_2$-$J_1$), or sulfoxyl (S(═O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25 (22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 20017, 129, 8362-8379; Elayadi et al., Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191;; Torsten et al., WO 2004/106356;Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

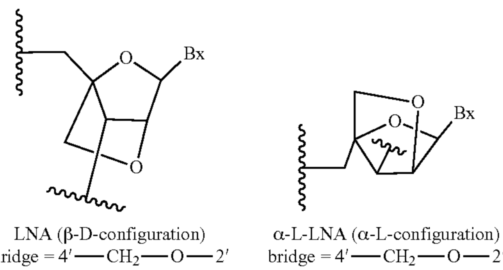

α-L-methyleneoxy ($4'-CH_2$—O-2') or α-L-LNA bicyclic nucleosides have been incorporated into antisense oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

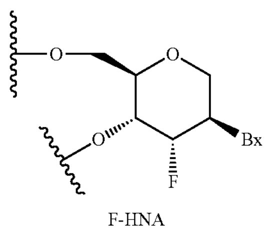

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

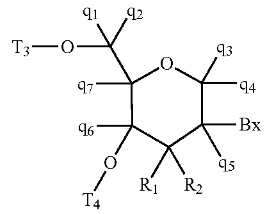

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom.

For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

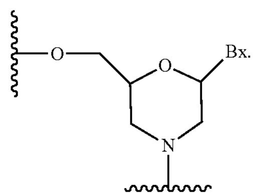

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine , 2-thiouracil, 2-thiothymine and 2-thiocytosine, 5-propynyl (—C≡C—$CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906;; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

B. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P═S"), and phosphorodithioates ("HS—P═S"). Representative non-phosphorus containing internucleoside linking groups include but are not limited to methylenemethylimino (—$CH_2$—N($CH_3$)—O—$CH_2$—), thiodiester, thionocarbamate (—O—C(═O)(NH)—S—); siloxane (—O—$SiH_2$—O—); and N,N'-dimethylhydrazine (—$CH_2$—N($CH_3$)—N($CH_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-

$CH_2$—$N(CH_3)$—O-5'), amide-3 (3'-$CH_2$—C(═O)—N(H)-5'), amide-4 (3'-$CH_2$—N(H)—C(═O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

C. Certain Motifs

In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the nucleobase sequence).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the nucleosides on the gap side of each wing/gap junction are unmodified 2'-deoxyribosyl nucleosides and the nucleosides on the wing sides of each wing/gap junction are modified nucleosides. In certain such embodiments, each nucleoside of the gap is an unmodified 2'-deoxyribosyl nucleoside. In certain such embodiments, each nucleoside of each wing is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain such embodiments, each nucleoside to the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

D. Certain Lengths

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides

E. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists if of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

In certain embodiments, oligonucleotides have a nucleobase sequence that is not 100% complementary to a target nucleic acid or any nucleic acid in a cell. In certain such embodiments, oligonucleotides are less than 90% complementary to any nucleic acid in a cell. In certain such embodiments, oligonucleotides are less than 80% or less than 70% complementary to any nucleic acid in a cell. In certain embodiments, oligonucleotides have a nucleobase sequence that is less than 100%, less than 90%, less than 80%, or less than 70% complementary to any known nucleic acid sequence in the cell.

In certain embodiments, methods described herein comprise contacting a cell with a first compound comprising a first modified oligonucleotide and a second compound comprising a second modified oligonucleotide, wherein the nucleobase sequence of one of the first and second modified oligonucleotides is complementary to a target nucleic acid and the nucleobase sequence of the other of the first and second modified oligonucleotides is less than 100%, less than 90%, less than 80%, or less than 70% complementary to any target nucleic acid or any nucleic acid in the cell. In certain such embodiments, the modified oligonucleotide that is less than 100%, less than 90%, less than 80%, or less than 70% complementary to any target nucleic acid or any nucleic acid in the cell modulates protein aggregation and/or sub-cellular distribution of at least one protein. In certain such embodiments, the size or amount of protein aggregates in the cell is decreased and/or the nuclear to cytoplasmic ratio of the sub-cellular distribution of the at least one protein is increased.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., Proc. Natl. Acad. Sci. USA, 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds comprising oligonucleotides, such as oligomeric compounds, the conjugate linker is a single chemical bond (i.e., the conjugate moiety is attached directly to an oligonucleotide through a single bond). In certain oligomeric compounds, a conjugate moiety is attached to an oligonucleotide via a more complex conjugate linker comprising one or more conjugate linker moieties, which are sub-units making up a conjugate linker. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

In certain embodiments, compounds of the invention are single-stranded. In certain embodiments, oligomeric compounds are paired with a second oligonucleotide or oligomeric compound to form a duplex, which is double-stranded.

III. Certain Antisense Compounds

In certain embodiments, the present invention provides antisense compounds, which comprise or consist of an oligomeric compound comprising an antisense oligonucleotide, having a nucleobase sequences complementary to that of a target nucleic acid. In certain embodiments, antisense compounds are single-stranded. Such single-stranded antisense compounds typically comprise or consist of an oligomeric compound that comprises or consists of a modified oligonucleotide and optionally a conjugate group. In certain embodiments, antisense compounds are double-stranded. Such double-stranded antisense compounds comprise a first oligomeric compound having a region complementary to a target nucleic acid and a second oligomeric compound having a region complementary to the first oligomeric compound. The first oligomeric compound of such double stranded antisense compounds typically comprises or consists of a modified oligonucleotide and optionally a conjugate group. The oligonucleotide of the second oligomeric compound of such double-stranded antisense compound may be modified or unmodified. Either or both oligomeric compounds of a double-stranded antisense compound may comprise a conjugate group. The oligomeric compounds of double-stranded antisense compounds may include non-complementary overhanging nucleosides.

In certain embodiments, oligomeric compounds of antisense compounds are capable of hybridizing to a target nucleic acid, resulting in at least one antisense activity. In certain embodiments, antisense compounds selectively affect one or more target nucleic acid. Such selective antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, the invention provides antisense compounds that are sufficiently "DNA-like" to elicit RNase H activity. Further, in certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain such embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain such embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

IV. Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism (SNP). In certain such embodiments, the antisense compound is capable of modulating expression of one allele of the SNP-containing target nucleic acid to a greater or lesser extent than it modulates another allele. In certain embodiments, an antisense compound hybridizes to a (SNP)-containing target nucleic acid at the single-nucleotide polymorphism site.

In certain embodiments, antisense compounds are at least partially complementary to more than one target nucleic acid. For example, antisense compounds of the present invention may mimic microRNAs, which typically bind to multiple targets.

A. Complementarity/Mismatches to the Target Nucleic Acid

In certain embodiments, antisense compounds comprise antisense oligonucleotides that are complementary to the target nucleic acid over the entire length of the oligonucleotide. In certain embodiments, such oligonucleotides are 99% complementary to the target nucleic acid. In certain embodiments, such oligonucleotides are 95% complementary to the target nucleic acid. In certain embodiments, such oligonucleotides are 90% complementary to the target nucleic acid. In certain embodiments, such oligonucleotides are 85% complementary to the target nucleic acid. In certain embodiments, such oligonucleotides are 80% complementary to the target nucleic acid. In certain embodiments, antisense oligonucleotides are at least 80% complementary to the target nucleic acid over the entire length of the oligonucleotide and comprise a region that is 100% or fully complementary to a target nucleic acid. In certain such embodiments, the region of full complementarity is from 6 to 20 nucleobases in length. In certain such embodiments, the region of full complementarity is from 10 to 18 nucleobases in length. In certain such embodiments, the region of full complementarity is from 18 to 20 nucleobases in length.

In certain embodiments, oligonucleotides comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the antisense compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region.

V. Certain Pharmaceutical Compositions

In certain embodiments, the present invention provides pharmaceutical compositions comprising one or more antisense compound or a salt thereof. In certain such embodiments, the pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one antisense compound and sterile water. In certain embodiments, the sterile water is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile PBS. In certain embodiments, the sterile PBS is pharmaceutical grade PBS.

In certain embodiments, pharmaceutical compositions comprise one or more or antisense compound and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an antisense compound encompass any pharmaceutically acceptable salts of the antisense compound, esters of the antisense compound, or salts of such esters. In certain embodiments, pharmaceutical compositions comprising antisense compounds comprising one or more antisense oligonucleotide, upon administration to an animal, including a human, are capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an antisense compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and other publications recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^{m}$CGAUCG," wherein $^{m}$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as α or β such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their racemic and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}$H hydrogen atoms. Isotopic substitutions encompassed by the compounds herein include but are not limited to: $^{2}$H or $^{3}$H in place of $^{1}$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

Example 1: Localization of Modified Oligonucleotides in Cells Expressing FUS

Compounds

Compounds comprising modified oligonucleotides were prepared using standard oligonucleotide synthesis techniques well known in the art. The compounds in the table below comprise modified oligonucleotides that are 5-10-5 cEt gapmers, wherein the central gap segment contains ten 2'-deoxynucleosides and is flanked by wing segments on the 3' and 5' ends, each containing five bicyclic nucleosides with a cEt (2',4'-constrained ethyl) modification. Every internucleoside linkage of each oligonucleotide is a phosphorothioate (PS) linkage. The nucleobase sequences of the modified oligonucleotides are either 100% complementary to the genomic sequence of human PTEN (GENBANK No. NM_030059.12, truncated from 8370000 to 8482000, herein referred to as SEQ ID No. 1) or are not 100% complementary to any known human gene. The compounds in the table below also comprise a Cy3 or Alex Fluor 594 conjugate group in order to allow detection of the oligonucleotides in cells.

TABLE 1

Compounds comprising modified oligonucleotides

| Compound ID | 5' End Cap | Sequence | Target | SEQ ID No. |
|---|---|---|---|---|
| 598987 | Cy3 | $^{m}C_{ks}T_{ks}G_{ks}{}^{m}C_{ks}T_{ks}A_{ds}G_{ds}{}^{m}C_{ds}{}^{m}C_{ds}T_{ds}{}^{m}C_{ds}T_{ds}G_{ds}G_{ds}A_{ds}T_{ks}T_{ks}T_{ks}G_{ks}A_{k}$ | PTEN | 2 |
| 766635 | AF594 | $^{m}C_{ks}T_{ks}G_{ks}{}^{m}C_{ks}T_{ks}A_{ds}G_{ds}{}^{m}C_{ds}{}^{m}C_{ds}T_{ds}{}^{m}C_{ds}T_{ds}G_{ds}G_{ds}A_{ds}T_{ks}T_{ks}T_{ks}G_{ks}A_{k}$ | PTEN | 2 |
| 950431 | Cy3 | $^{m}C_{ks}{}^{m}C_{ks}T_{ks}T_{ks}{}^{m}C_{ks}{}^{m}C_{ds}{}^{m}C_{ds}T_{ds}G_{ds}A_{ds}A_{ds}G_{ds}G_{ds}T_{ds}T_{ds}{}^{m}C_{ks}{}^{m}C_{ks}T_{ks}{}^{m}C_{ks}{}^{m}C_{k}$ | none | 3 |

Subscripts: "s" indicates a phosphorothioate internucleoside linkage; "k" indicates a 2',4'-constrained ethyl bicyclic sugar moiety (cEt); "d" indicates a 2'-deoxyribo unmodified sugar moiety. Superscript m preceding a "C" indicates a 5-methylcytosine.

Experimental Protocol

HeLa cells were cultured in Dulbecco's Modified Eagle Medium (DMEM) supplemented with 10% Fetal Bovine Serum (FBS) and 1% penicillin-streptomycin and seeded at 12,500 cells/cm$^2$ on collagen-coated coverslips (for immunofluorescence detection of 598987) or 35 mm collagen-coated live imaging dishes (P35GCOL-1.5-14-C, MatTek, Ashland, Mass.) (for live cell imaging). Plasmids containing a pCMV promoter and either tGFP-FUS(WT) or tGFP-FUS (P525L) were individually mixed with the TurboFect transfection reagent (Thermo Fisher Scientific) in Opti-MEM and incubated for 15 min at room temperature. HeLa cells were then treated for 16-24 hours per manufacturer's instructions for transient transfection. Cells were then washed once with PBS and incubated for 4-6 hours in Opti-MEM containing a final concentration of 50 nM of a compound listed in the table above. In a separate experiment, the cells were incubated with 50 nM with compound 598987 first, washed, and then transiently transfected with tGFP-FUS-P525L as above.

Confocal microscopy was used to visualize the cells. Confocal images were acquired on an Olympus FV1000 microscope using a PlanApo N 60×O objective (N.A.=1.42) with excitation laser lines at 450, 488, 542, and 635 nm. For immunofluorescence imaging, cells were fixed with 4% formaldehyde in PBS for 30 minutes at room temperature, permeabilized for 5 minutes with 0.1% Triton-X 100, washed three times with PBS, and blocked for 30 minutes at room temperature with blocking buffer (1 mg/mL BSA in PBS). Primary antibody incubation for G3BP protein (mouse-anti-G3BP, Abcam ab56574, 1:600) was performed for 2 hours at room temperature or overnight at 4° C. in blocking buffer, followed by 3 washes of 0.1% Nonidet P40 substitute 74385 (Sigma-Aldrich) in PBS. Secondary antibody (goat anti-mouse IgG (H+L)-Alexa Fluor 488, Jackson ImmunoResearch 115-525-146) was incubated 1:200 in blocking buffer for 1 hour at room temperature, followed by 3 washes.

Co-localization analysis of compounds with G3BP was performed using the JACoP plugin for ImagJ-Fiji using images captured under identical non-saturating exposure settings (Schindelin, J., Arganda-Carreras, I., Frise, E., Kaynig, V., Longair, M., Pietzsch, T., Preibisch, S., Rueden, C., Saalfeld, S., Schmid, B. et al. (2012) Fiji: an open-source platform for biological-image analysis. Nat Methods, 9, 676-682; Bolte, S. and Cordelieres, F. P. (2006) A guided tour into subcellular co-localization analysis in light microscopy. J Microsc, 224, 213-232). The thresholded Manders' co-localization coefficient was calculated using constant maximum and minimum threshold values within a set of conditions to be compared. Values reported in a single table were obtained using the same image exposure settings and threshold values. Inverted co-localization is a control value obtained by rotating one of the two images being compared 90 degrees and performing the same analysis. See Bolte, 2006 for a more in-depth discussion of JACoP software and the threshold Manders' coefficient. For image co-localization analysis, each field contained an average of approximately four cells. A high co-localization coefficient indicates co-localization with the G3BP stress granule marker, while a lower co-localization coefficient indicates random distribution relative to G3BP.

As an additional semi-quantitative way to analyze localization of compounds comprising oligonucleotides in cells, comparative quantification of granule/nuclear intensity was done by image analysis using ImageJ-FIJI macro scripts. First, images were captured under identical non-saturating exposure settings, and then the average pixel intensity in the nucleus was calculated based on the DAPI channel. An absolute intensity threshold was used to create a nuclear selection mask. In the Cy3 channel, a background subtraction was performed and the average pixel intensity in the nuclear selection was measured. For quantification of average pixel intensity in the tGFP channel (tGFP, tGFP-FUS-P525L, tGFP-PSF-ΔNLS channels), a uniform absolute intensity threshold was applied to create a tGFP (granule) selection mask. In the Cy3 channel, a background subtraction was performed in this selection and the average pixel intensity in the tGFP selection was measured. Results are presented as the average ratio of granule/nuclear intensity for 12-18 cells for each condition.

For live cell imaging, cells were treated with 1 μg/mL Hoechst 33342 (Thermo Fisher) and imaged in FluoroBrite DMEM (Thermo Fisher) at 37° C.

Imaging Results

Fixed Cells

In fixed HeLa cells transiently transfected with tGFP-FUS-WT, a diffuse GFP signal localized to the nucleus of cells, overlapping with the signal from the nuclear stain DAPI, and no GFP signal was observed in the cytoplasm. In cells transiently transfected with tGFP-FUS-P525L, the GFP signal was instead observed as bright spots in the cytoplasm, non-overlapping with nuclear DAPI stain. These cytoplasmic spots overlapped with the G3BP stress granule maker.

When cells expressing tGFP-FUS-WT were treated with compound 598987, the Cy3 signal was visible throughout the image, and was more prevalent in the nucleus than the cytoplasm. In contrast, when cells expressing tGFP-FUS-P525L were treated with 598987, the Cy3 signal localizes to the G3BP-containing granules in the cytoplasm. This result indicated that the P525L mutation of FUS caused localization of FUS to change from the nucleus to the cytoplasm and co-localization with G3BP-positive granules. The localization of the cEt modified oligonucleotide also changed from primarily in the nucleus to the cytoplasm where it also co-localized with granules containing the mutant FUS.

A similar result was observed with two other cEt modified oligonucleotides. In fixed HeLa cells transiently transfected with tGFP-FUS-WT and then treated with compound 950431 or 766635, no co-localization was seen between the compound and G3BP. In contrast, statistically significant ($p<0.001$) co-localization was observed between the compound and G3BP in cells transiently transfected with tGFP-FUS-P525L and then treated with compound 950431 or 766635.

TABLE 2

| Thresholded Mander's co-localization coefficient: compound with G3BP (%) | | | |
|---|---|---|---|
| Compound | Expressed Protein | Colocalization Coeffcient | Inverted Colocalization Coefficient |
| 766635 | tGFP | 11.5 | 9.6 |
| | tGFP-FUS-WT | 11.6 | 2.8 |
| | tGFP-FUS-P525L | 30.2 | 7.3 |

TABLE 3

| Thresholded Mander's co-localization coefficient: compound with G3BP (%) | | | |
|---|---|---|---|
| Compound | Expressed Protein | Colocalization Coeffcient | Inverted Colocalization Coefficient |
| 950431 | tGFP | 9.1 | 6.8 |
| | tGFP-FUS-WT | 4.1 | 2.2 |
| | tGFP-FUS-P525L | 33.9 | 5.6 |

TABLE 4

| Granule/Nuclear Ratio | | |
|---|---|---|
| Compound | Expressed Protein | Granule/Nuclear Ratio |
| 766635 | tGFP | 0.55 |
| | tGFP-FUS-WT | 1.00 |
| | tGFP-FUS-P525L | 3.88 |

TABLE 5

| Granule/Nuclear Ratio | | |
|---|---|---|
| Compound | Expressed Protein | Granule/Nuclear Ratio |
| 950431 | tGFP | 0.58 |
| | tGFP-FUS-WT | 0.99 |
| | tGFP-FUS-P525L | 3.03 |

Live Cells

Live HeLa cells were transiently transfected with either tGFP-FUS-WT or tGFP-FUS-P525L, then treated with 598987 as above. In a parallel experiment, live HeLa cells were treated with 598987 for 5 hours prior to transient transfection with tGFP-FUS-WT or tGFP-FUS-P525L, followed by live cell imaging. Granule/nuclear ratios for compound localization were determined as above.

TABLE 6

| Granule/Nuclear Ratio | | |
|---|---|---|
| Compound, time of addition | Expressed Protein | Granule/ Nuclear Ratio |
| 598987, added 16 hr after plasmid transfection | tGFP-FUS-WT | 0.98 |
| | tGFP-FUS-P525L | 1.56 |
| 598987, added before plasmid transfection | tGFP-FUS-WT | 1.01 |
| | tGFP-FUS-P525L | 1.76 |

A431 Cells

To confirm that these results were not specific to the HeLa cell type, A431 cells were stably transduced with lentiviral particles (MOI ~5) containing tGFP, tGFP-FUS-WT, or tGFP-FUS-P525L. Localization of tGFP-FUS-WT was similar to that described in HeLa cells above. In many cells, tGFP-FUS-P525L was diffuse through the cytoplasm, while in a subset of these cells, cytoplasmic aggregates were observed. A431 cells were transfected with 50 nM of compound 950431 for 5 hours. In cells with cytoplasmic aggregates of tGFP-FUS-P525L, compound 950431 co-localized with these aggregates. In cells expressing tGFP-FUS-WT, compound 950431 primarily localized to the nucleus, as observed in HeLa cells.

Example 2: Localization of Modified Oligonucleotides in Cells Expressing PSF

Background

The C-terminal nuclear localization sequence of PSF is required for nuclear localization of the protein. A mutant lacking the final 6 amino acids of the protein lacks this sequence and is defective for nuclear uptake.

Experimental Protocol

HeLa cells were transiently transfected with EGFP-PSF-WT(1-707) or EGFP-PSF-ΔNLS(1-701) and treated with 50 nM of compound as described in Example 1. Confocal immunofluorescence imaging was used to visualize GFP (PSF), Cy3 (modified oligonucleotide), G3BP (cytoplasmic granule marker), and DAPI (nuclear stain), with cell fixing and labeling as described in Example 1.

Imaging Results

TABLE 7

| Thresholded Mander's co-localization coefficient: compound with G3BP (%) | | | |
|---|---|---|---|
| Compound | Expressed Protein | Colocalization Coeffcient | Inverted Colocalization Coefficient |
| 766635 | EGFP | 11.5 | 9.6 |
| | EGFP-PSF-WT(1-707) | 3.2 | 3.0 |
| | EGFP-PSF-ΔNLS(1-701) | 36.6 | 6.6 |

TABLE 8

| Thresholded Mander's co-localization coefficient: compound with G3BP (%) | | | |
|---|---|---|---|
| Compound | Expressed Protein | Co-localization Coeffcient | Inverted Co-localization Coefficient |
| 950431 | EGFP | 9.1 | 6.8 |
| | EGFP-PSF-WT(1-707) | 3.1 | 3.6 |
| | EGFP-PSF-ΔNLS(1-701) | 32.2 | 5.2 |

TABLE 9

| Granule/Nuclear Ratio | | |
|---|---|---|
| Compound | Expressed Protein | Granule/Nuclear Ratio |
| 766635 | tGFP | 0.55 |
| | tGFP-PSF-WT(1-707) | 1.00 |
| | tGFP-PSF-ΔNLS(1-701) | 2.65 |

TABLE 10

| Granule/Nuclear Ratio | | |
|---|---|---|
| Compound | Expressed Protein | Granule/Nuclear Ratio |
| 950431 | tGFP | 0.58 |
| | tGFP-PSF-WT(1-707) | 0.99 |
| | tGFP-PSF-ΔNLS(1-701) | 2.34 |

Example 3: Effect of Modified Sugar Moieties on Oligonucleotide Localization

Compounds

Compounds comprising modified oligonucleotides were prepared using standard oligonucleotide synthesis well known in the art. Compounds 446654, 598987, 626825, and 851810 are 5-10-5 gapmers, wherein each central gap segment containing ten 2'-deoxynucleosides is flanked by wing segments on the 3' and 5' ends, each containing 5 nucleosides with a modification indicated in the table below. The modified oligonucleotide of compound XL198 contains only 2'-deoxyribonucleosides. These oligonucleotides comprise full phosphothioate (full PS) linkages. The modified oligonucleotides are 100% complementary to the genomic sequence of PTEN, GENBANK No. NM_030059.12, truncated from 8370000 to 8482000, SEQ ID No. 1.

TABLE 11

| Compounds comprising modified oligonucleotides | | | | |
|---|---|---|---|---|
| Compound ID | 5'-End Cap | Chemistry Notation | Target | Seq ID No |
| 446654 | Cy3 | ${}^{m}C_{es}T_{es}G_{es}{}^{m}C_{es}T_{es}A_{ds}G_{ds}{}^{m}C_{ds}{}^{m}C_{ds}T_{ds}{}^{m}C_{ds}T_{ds}G_{ds}G_{ds}A_{ds}T_{es}T_{es}T_{es}G_{es}A_{e}$ | PTEN | 2 |
| 598987 | Cy3 | ${}^{m}C_{ks}T_{ks}G_{ks}{}^{m}C_{ks}T_{ks}A_{ds}G_{ds}{}^{m}C_{ds}{}^{m}C_{ds}T_{ds}{}^{m}C_{ds}T_{ds}G_{ds}G_{ds}A_{ds}T_{ks}T_{ks}T_{ks}G_{ks}A_{k}$ | PTEN | 2 |
| 626825 | Cy3 | $C_{fs}U_{fs}G_{fs}C_{fs}U_{fs}A_{ds}G_{ds}{}^{m}C_{ds}{}^{m}C_{ds}T_{ds}{}^{m}C_{ds}T_{ds}G_{ds}G_{ds}A_{ds}U_{fs}U_{fs}U_{fs}G_{fs}A_{f}$ | PTEN | 4 |
| XL198 | Cy3 | $C_{ds}T_{ds}G_{ds}C_{ds}T_{ds}A_{ds}G_{ds}C_{ds}C_{ds}T_{ds}C_{ds}T_{ds}G_{ds}G_{ds}A_{ds}T_{ds}T_{ds}T_{ds}G_{ds}A_{d}$ | PTEN | 2 |
| 851810 | AF647 | ${}^{m}C_{es}T_{es}G_{es}{}^{m}C_{es}T_{es}A_{ds}G_{ds}{}^{m}C_{ds}{}^{m}C_{ds}T_{ds}{}^{m}C_{ds}T_{ds}G_{ds}G_{ds}A_{ds}T_{es}T_{es}T_{es}G_{es}A_{e}$ | PTEN | 2 |

Subscripts: "s" indicates a phosphorothioate internucleoside linkage; "k" indicates a 2',4'-constrained ethyl bicyclic sugar moiety (cEt); "d" indicates a 2'-deoxyribo unmodified sugar moiety; "e" indicates a 2'-MOE sugar moiety; "f" indicates a 2'-F sugar moiety. Superscript m preceding a "C" indicates a 5-methylcytosine.

Experimental Protocol

HeLa cells were transfected with tGFP-FUS-P525L and 50 nM Cy3-modified oligonucleotide as described in Example 1 as well as 50 nM Alexa-647-labeled modified oligonucleotide, compound 851810 as a reference standard. To allow semi-quantitative comparisons among experimental groups, comparative quantification was done by image analysis using ImageJ-FIJI macro scripts. First, images were captured under identical non-saturating exposure settings, and then the average pixel intensity in the nucleus was calculated based on the DAPI channel. An absolute intensity threshold was used to create a nuclear selection mask. In the Cy3 channel, a background subtraction was performed and the average pixel intensity in the nuclear selection was measured. For quantification of average pixel intensity in the tGFP channel (tGFP, tGFP-FUS-P525L, tGFP-PSF-ANLS channels), a uniform absolute intensity threshold was applied to create a tGFP-selection mask. In the Cy3 channel, a background subtraction was performed in this selection and the average pixel intensity in the tGFP selection was measured. Results are presented as the average ratio of granule/nuclear intensity for 15-18 cells for each condition. The results indicate that the compounds comprising 2'-MOE and cEt modifications localized to cytoplasmic granules over the nucleus to a greater extent than the other compounds tested.

Results

TABLE 12

| Granule/nuclear average pixel intensity ratio | |
|---|---|
| Compound ID | Granule/nuclear ratio |
| 446654 | 1.12 |
| 598987 | 2.80 |
| 626825 | 0.95 |
| XL198 | 0.90 |

Example 4: Protein-Oligonucleotide Interactions

Compounds

Compounds comprising oligonucleotides were prepared using standard oligonucleotide synthesis well known in the art and are shown in the table below.

TABLE 13

| Compounds comprising modified oligonucleotides | | | | |
|---|---|---|---|---|
| Compound ID | 5'-End Cap | Chemistry Notation | Target | Seq ID No |
| 766633 | AF594 | ${}^{m}C_{es}T_{es}G_{es}{}^{m}C_{es}T_{es}A_{ds}G_{ds}{}^{m}C_{ds}{}^{m}C_{ds}T_{ds}{}^{m}C_{ds}T_{ds}G_{ds}G_{ds}A_{ds}T_{es}T_{es}T_{es}G_{es}A_{e}$ | PTEN | 2 |
| 766635 | AF594 | ${}^{m}C_{ks}T_{ks}G_{ks}{}^{m}C_{ks}T_{ks}A_{ds}G_{ds}{}^{m}C_{ds}{}^{m}C_{ds}T_{ds}{}^{m}C_{ds}T_{ds}G_{ds}G_{ds}A_{ds}T_{ks}T_{ks}T_{ks}G_{ks}A_{k}$ | PTEN | 2 |
| 766637 | AF594 | $C_{fs}U_{fs}G_{fs}C_{fs}U_{fs}A_{ds}G_{ds}{}^{m}C_{ds}{}^{m}C_{ds}T_{ds}{}^{m}C_{ds}T_{ds}G_{ds}G_{ds}A_{ds}U_{fs}U_{fs}U_{fs}G_{fs}A_{f}$ | PTEN | 4 |
| JB39 | AF594 | $C_{ro}U_{ro}G_{ro}C_{ro}U_{ro}A_{ro}G_{ro}C_{ro}C_{ro}U_{ro}C_{ro}U_{ro}G_{ro}G_{ro}A_{ro}U_{ro}U_{ro}U_{ro}G_{ro}A_{r}$ | PTEN | 5 |

Subscripts: "s" indicates phosphorothioate internucleoside linkage; "o" indicates phosphodiester internucleoside linkage; "k" indicates 2'-4' constrained ethyl bicyclic sugar moity (cEt); "e" indicate 2'-MOE sugar moiety; "f" indicate 2'-fluoro sugar moiety; "r" indicate unmodified ribosyl sugar moiety; and "d" indicate unmodified 2'-deoxyribosyl sugar moiety. "${}^{m}C$" indicates 5-methylcytosine.

Proteins

DNA constructs described herein were cloned into NEB-IVT (New England Biolabs DHFR Control Plasmid) using standard protocols and expressed using the PURExpress in vitro Protein Synthesis Kit (New England Biolabs). All constructs included nanoluciferase (NLUC) and an HA tag or a FLAG tag. Aside from the control protein NLUC-HA, all constructs included all or part of FUS, as indicated by amino acid numbers in the table below. For several constructs, arginine to serine ("R/S") mutations were made for all arginine residues in one of the two RGG domains of FUS, as indicated in the table below.

Experimental Protocol

NanoBRET (bioluminescence resonance energy transfer) binding assays were performed with protein bound to magnetic beads (Vickers and Crooke. *PLOS One,* 11 (8), (2016).). First, the relative amount of purified protein per volume of bead suspension (based on nluc activity) was determined in 2× binding buffer (200 mM potassium acetate, 40 mM Tris pH 8.0, 2 mM EDTA, 0.02% NP-40, 6 μg/mL BSA, and 1:1000 Promega Nano-Glo luciferase substrate) using an eight-point dilution curve over ~3.5 orders of magnitude. The Alexafluor594-labeled modified oligonucleotides were diluted into water in opaque white 96-well plates at concentrations ranging from pM to low μM in 50 μL final volume. 50 μL/well of 2× binding buffer containing $10^6$ RLU (relative luminescence units) beads/well was added and plates were shaken for 10 minutes at room temperature. Nanoluciferase activity and BRET were measured in a Glowmax Discover plate reader and $K_D$ values, shown in the tables below, were calculated using GraphPad Prism. The results indicate that the compound comprising 2'-F modifications bound with higher affinity to the FUS domains and mutants tested, including the low complexity domain (amino acids 1-283), than the other compounds tested.

TABLE 14

| $K_D$ values (nM) determined using nanoBRET | | | |
|---|---|---|---|
| | Compound ID | | |
| Protein Construct | 766633 | 766635 | 766637 |
| NLUC-HA | >1,000 | >1,000 | >1,000 |
| FUS(1-283)-NLUC-HA | 44.7 | 35.2 | 7.1 |

TABLE 14-continued

| $K_D$ values (nM) determined using nanoBRET | | | |
|---|---|---|---|
| | Compound ID | | |
| Protein Construct | 766633 | 766635 | 766637 |
| FUS(1-375)-NLUC-HA | 16.7 | 12.1 | 1.4 |
| FUS(284-375)-NLUC-HA | >1,000 | >1,000 | 340.4 |
| FUS(375-526)[P525L]-NLUC-HA | 36.8 | 30.7 | 4.4 |
| FUS(1-526)[P525L]-NLUC-HA | 16.4 | 17.2 | 2.2 |
| NLUC-FUS(1-526)[P525L]-HA | 16.6 | 12.4 | 1.9 |

TABLE 15

| $K_D$ values (nM) determined using nanoBRET | | | |
|---|---|---|---|
| | Compound ID | | |
| Protein Construct | 766633 | 766635 | 766637 |
| FUS(1-375)-NLUC-HA | 11.8 | 11.3 | 0.8 |
| FUS(284-375)-NLUC-HA | >1,000 | >1,000 | 424.1 |
| FUS(213-375)-NLUC-HA | 10.0 | 9.0 | 0.9 |
| FUS(242-375)-NLUC-HA | 102.8 | 117.2 | 11.0 |

TABLE 16

| $K_D$ values (nM) determined using nanoBRET | | | |
|---|---|---|---|
| | Compound ID | | |
| Protein Construct | 766633 | 766635 | 766637 |
| FUS(375-526)1[P252L]-NLUC-HA | 23.7 | 19 | 2.9 |
| FUS(375-421)-NLUC-HA | 290.6 | 203 | 40.8 |
| FUS(375-526)[P525L][R/S in 454-526]-NLUC-HA | 282.3 | 290.1 | 38.4 |
| FUS(375-526)[P525L][R/S in 375-422]-NLUC-HA | 12.4 | 14.3 | 1.8 |
| FUS(455-526)[P525L]-NLUC-HA | 39.4 | 34.3 | 6.6 |

TABLE 17

| $K_D$ values (nM) determined using nanoBRET | | | | |
|---|---|---|---|---|
| | Compound | | | |
| Protein Construct | 766633 | 766635 | 766637 | JB39 |
| FUS(1-526)[P525L]-NLUC-FLAG | 1.2 | 3 | 0.4 | 143.3 |
| FUS(1-421)-FUS(455-526)[P525L]-NLUC-FLAG | 4.2 | 6.8 | 1.1 | 205.9 |
| FUS(1-526)[P525L][R/S in 375-422 and 454-526]-NLUC-FLAG | 1.6 | 3.7 | 0.3 | 248.2 |

Example 5: Protein-Oligonucleotide Interactions in Presence of Unlabed Competitor Olignucleotide Compounds comprising or consisting of oligonucleotides were prepared using standard oligonucleotide synthesis well known in the art and are shown in the table below.

TABLE 18

| Compounds comprising oligonucleotides | | | | |
|---|---|---|---|---|
| Compound ID | 5′-End Cap | Chemistry Notation | Target | Seq ID No |
| JB39 | AF594 | $C_{ro}U_{ro}G_{ro}C_{ro}U_{ro}A_{ro}G_{ro}C_{ro}C_{ro}U_{ro}C_{ro}U_{ro}G_{ro}G_{ro}A_{ro}U_{ro}U_{ro}U_{ro}G_{ro}A_{r}$ | PTEN | 5 |
| JB40 | none | $C_{do}T_{do}G_{do}C_{do}T_{do}A_{do}G_{do}C_{do}C_{do}T_{do}C_{do}T_{do}G_{do}G_{do}A_{do}T_{do}T_{do}T_{do}G_{do}A_{d}$ | PTEN | 2 |
| B41 | none | $C_{ds}T_{ds}G_{ds}C_{ds}T_{ds}A_{ds}G_{ds}C_{ds}C_{ds}T_{ds}C_{ds}T_{ds}G_{ds}G_{ds}A_{ds}T_{ds}T_{ds}T_{ds}G_{ds}A_{d}$ | PTEN | 2 |
| JB42 | none | $C_{rs}U_{rs}G_{rs}C_{rs}U_{rs}A_{rs}G_{rs}C_{rs}C_{rs}U_{rs}C_{rs}U_{rs}G_{rs}G_{rs}A_{rs}U_{rs}$UrsUrsGrsAr | PTEN | 5 |

Subscripts: "s" indicates phosphorothioate internucleoside linkage; "o" indicates phosphodiester internucleoside linkage; "r" indicate unmodified ribosyl sugar moiety; and "d" indicate unmodified 2′-deoxyribosyl sugar moiety.

Proteins

Binding assays were performed using full length FUS [P525L]-NLUC-FLAG as described in Example 4.

Experimental Protocol

Competitive NanoBRET binding assays were performed with unlabeled oligonucleotides JB40, JB41, and JB42. First, the relative amount of purified protein per volume of bead suspension (based on nluc activity) was determined in 2× binding buffer (200 mM potassium acetate, 40 mM Tris pH 8.0, 2 mM EDTA, 0.02% NP-40, 6 μg/mL BSA, and 1:1000 Promega Nano-Glo luciferase substrate) using an eight-point dilution curve over ~3.5 orders of magnitude. Alexafluor594-labeled JB39 was diluted into water in opaque white 96-well plates a single concentration, and varying concentrations of JB40, JB41, or JB42, spanning the pM to low μM range were added to a final total volume of 50 μL/well. 50 μL/well of 2× binding buffer containing $10^6$ RLU (relative luminescence units) beads/well was added and plates were shaken for 10 minutes at room temperature. Nanoluciferase activity and BRET were measured in a Glowmax Discover plate reader and $K_D$ values, shown in the table below, were calculated using GraphPad Prism. The $K_D$ values shown in the table below represent the concentration of competitor oligonucleotide required to cause 50% dissociation of the BRET pair. The results indicate that the phosphorothioate containing oligonucleotides bound the FUS mutant with higher affinity than the phosphodiester containing oligonucleotides.

TABLE 19

| $K_D$ (nM) values determined using competitive nanoBRET | | | |
|---|---|---|---|
| | Compound ID | | |
| BRET pair | JB40 | JB41 | JB42 |
| FUS(1-526)[P525L]-NLUC-HA/JB39 | >1000 | 0.4 | 7.2 |

Example 6: Protein-Oligonucleotide Interactions

NanoBRET binding assays were performed as described in Example 4 using oligonucleotides described in Example 4 and β23 containing protein constructs. β23 is an artificially designed β-sheet forming protein that aggregates in cells and that can be targeted to the cytoplasm by including a nuclear export sequence, together referred to as NES-β23. Three fusion proteins containing NES-β23 were constructed and used in NanoBRET binding assays: control HA-NES-β23-NLUC, HA-NES-β23-NLUC-FUS(375-526)[P525L], and HA-NES-β23-NLUC-FUS(375-526)[P525L][R/S in 375-422 and 454-526]. The resulting $K_D$ values are shown in the table below. These protein constructs were also tested in immunofluoresence imaging experiments in HeLa cells using compounds 598987, as described in Example 1. The results in the tables below show that the compounds comprising 2'-F modifications bound the beta-sheet forming proteins with higher affinity than the other compounds tested.

TABLE 20

$K_D$ values (nM) determined using nanoBRET

| Protein Construct | Compound ID 766633 | 766635 | 766637 |
|---|---|---|---|
| HA-NES-β23-NLUC | >1,000 | 949.7 | 345.1 |
| HA-NES-β23-NLUC-FUS(375-526)[P525L] | 163.7 | 58.4 | 13.8 |
| HA-NES-β23-NLUC-FUS(375-526)[P525L] [R/S in 375-422 and 454-526]. | >1,000 | >1,000 | 200.1 |

TABLE 21

Nuclear/granule intensity ratios

| Protein Construct | Nuclear/granule intensity ratio |
|---|---|
| HA-NES-β23-NLUC | 0.78 |
| HA-NES-β23-NLUC-FUS(375-526)[P525L] | 2.15 |
| HA-NES-β23-NLUC-FUS(375-526)[P525L] [R/S in 375-422 and 454-526]. | 0.62 |

Example 7: Protein-Oligonucleotide Interactions

Modified oligonucleotides were prepared using standard oligonucleotide synthesis well known in the art and are shown in the table below. The modified oligonucleotides are 5-10-5 gapmers, wherein the central gap segment containing ten 2'-deoxynucleosides is flanked by wing segments on the 3' and 5' ends, each containing 5 nucleosides with modified sugar moieties as indicated in the table below. These oligonucleotides comprise full phosphothioate (full PS) linkages. See table legend in Tables 1, 2, 4, and 8.

TABLE 22

Modified oligonucleotides

| Compound ID | 5'-End Cap | Chemistry Notation | Target | Seq ID No |
|---|---|---|---|---|
| 116847 | none | ${}^{m}C_{es}T_{es}G_{es}{}^{m}C_{es}T_{es}A_{ds}G_{ds}{}^{m}C_{ds}{}^{m}C_{ds}T_{ds}{}^{m}C_{ds}T_{ds}G_{ds}G_{ds}A_{ds}T_{es}T_{es}T_{es}G_{es}A_{e}$ | PTEN | 2 |
| 404130 | none | $C_{fs}U_{fs}G_{fs}C_{fs}U_{fs}A_{ds}G_{ds}{}^{m}C_{ds}{}^{m}C_{ds}T_{ds}{}^{m}C_{ds}T_{ds}G_{ds}G_{ds}A_{ds}U_{fs}U_{fs}U_{fs}G_{fs}A_{f}$ | PTEN | 3 |
| 582801 | none | ${}^{m}C_{ks}T_{ks}G_{ks}{}^{m}C_{ks}T_{ks}A_{ds}G_{ds}{}^{m}C_{ds}{}^{m}C_{ds}T_{ds}{}^{m}C_{ds}T_{ds}G_{ds}G_{ds}A_{ds}T_{ks}T_{ks}T_{ks}G_{ks}A_{k}$ | PTEN | 2 |

Proteins

Protein p54nrb is a nucleic acid binding protein that forms a heterodimer with PSF. HA-NLUC tagged PSF and HA-HaloTag618 (Promega) tagged p54nrb were coexpressed in HeLa cells. NLUC and HaloTag618 form a BRET pair that can be used to detect interactions between the two proteins, and BRET is observed between HA-NLUC-PSF and HA-HaloTag618-p54nrb in cell lysate.

Experimental Protocol

HeLa cells coexpressing the two proteins were lysed, and the lysate was incubated with various concentrations of modified oligonucleotide in a competition experiment. BRET signal was analyzed as in Example 4. The $K_D$ values shown in the table below represent the concentration of competitor oligonucleotide required to cause 50% dissociation of the BRET pair. The results show that the oligonucleotide comprising 2'-F modifications disrupted the p54nrb-PSF interaction more effectively than the other compounds tested.

TABLE 23

$K_D$ values (nM) for HA-NLUC-PSF and HA-HaloTag618-p54nrb

| BRET pair | Competitor Compound ID 116847 | 582801 | 404130 |
|---|---|---|---|
| HA-NLUC-PSF/HA-HaloTag618-p54nrb | 2.46 | 5.12 | 0.66 |

Example 8: Localization of Modified Oligonucleotides in Cells Induced to Produce Stress Granules Compounds described above and in the table below were used to test oligonucleotide co-localization with induced stress granules.

TABLE 24

Compound comprising modified oligonucleotide

| Compound | 5'-End Cap | Chemistry Notation | Target | Seq ID No |
|---|---|---|---|---|
| 391857 | FITC | ${}^{m}C_{ls}T_{ls}G_{ls}{}^{m}C_{ls}T_{ls}A_{ds}G_{ds}{}^{m}C_{ds}{}^{m}C_{ds}T_{ds}{}^{m}C_{ds}T_{ds}G_{ds}G_{ds}A_{ds}T_{ls}T_{ls}T_{ls}G_{ls}A_{l}$ | PTEN | 2 |

Subscripts: "s" indicates a phosphorothioate internucleoside linkage; "l" indicates a β-D locked nucleic acid (β-D LNA); "k" indicates a 2',4'-constrained ethyl bicyclic sugar moiety (cEt); "d" indicates a 2'-deoxyribo unmodified sugar moiety. Superscript m preceding a "C" indicates a 5-methylcytosine.

Experimental Protocol

HeLa cells were either transfected for 5 hours or NEON electroporated with 50 nM compound 598987 or 391857. Cells were then incubated with DMSO, sodium arsenite, or 15d-PGJ2 for 1 hour, and then imaged with confocal immunofluorescence as described in Example 1. Sodium arsenite induces stress granules through a eIF2α-dependent mechanism and 15d-PGJ2 induces stress granules through a eIF2α-independent mechanism. The results of co-localization of the compounds with G3BP are shown in the tables below.

Imaging Results

TABLE 25

| Threshold Manders' Co-localization for transfected 598987 | | |
|---|---|---|
| Treatment condition | Co-localization | Inverted co-localization |
| Vehicle | 5.9 | 2.5 |
| Sodium arsenite | 10.6 | 4.0 |
| 15d-PGJ2 | 11.3 | 2.5 |

TABLE 26

| Threshold Manders' Co-localization for electroporated 598987 | | |
|---|---|---|
| Treatment condition | Co-localization | Inverted co-localization |
| Vehicle | 1.7 | 1.9 |
| Sodium arsenite | 9.3 | 2.3 |
| 15d-PGJ2 | 13.0 | 2.0 |

TABLE 27

| Threshold Manders' Co-localization for transfected 391857 | | |
|---|---|---|
| Treatment condition | Co-localization | Inverted co-localization |
| Vehicle | 5.7 | 3.5 |
| Sodium arsenite | 13.5 | 3.0 |
| 15d-PGJ2 | 10.8 | 1.4 |

TABLE 28

| Threshold Manders' Co-localization for electroporated 391857 | | |
|---|---|---|
| Treatment condition | Co-localization | Inverted co-localization |
| Vehicle | 0.4 | 0.3 |
| Sodium arsenite | 5.5 | 1.6 |
| 15d-PGJ2 | 10.3 | 1.3 |

Example 9: Granule/Nuclear Ratios

Granule/nuclear ratios of compounds 598987 and 391857 in the presence of transiently transfected HA-FUS-WT or HA-FUS-P525L were measured in HeLa cells using the immunofluorescence techniques described in Example 1. HA-FUS was detected using rabbit-anti-HA (Abcam Ab9110, 1:300) with secondary antibody goat anti-rabbit IgG(H+L)-AlexaFluor488 (Jackson ImmunoResearch 111-545-155, 1:200) for 598987 and with goat anti-rabbit IgG (H+L)-Cy5 (Jackson ImmunoResearch 115-175-144, 1:200) for 391857. The results are shown in the tables below.

TABLE 29

| Granule/Nuclear Ratio | | |
|---|---|---|
| Compound | Expressed Protein | Granule/Nuclear Ratio |
| 598987 | HA-FUS | 1.02 |
| | HA-FUS-P525L | 1.57 |

TABLE 30

| Granule/Nuclear Ratio | | |
|---|---|---|
| Compound | Expressed Protein | Granule/Nuclear Ratio |
| 391857 | HA-FUS | 0.99 |
| | HA-FUS-P525L | 1.82 |

Example 10: Oligonucleotide Localization in Presence of Protein Aggregates

HA-NES-β23-tGFP, HA-NES-β23-tGFP-FUS(375-526) [P525L], and HA-NES-β23-tGFP-FUS(375-526)[P525L] [R/S in 375-422 and 454-526] (see Example 6) were transiently transfected in HeLa cells. Cells were treated with 50 nM 598987 for 5 hr and then treated with 500 μM sodium arsenite for 1 hr prior to imaging. Image analysis was performed as described in Example 1. Each value represents the average of 18-19 images.

TABLE 31

| Granule/Nuclear Ratio for 598987 | |
|---|---|
| Protein | Granule/nuclear ratio |
| HA-NES-β23-tGFP | 0.79 |
| HA-NES-β23-tGFP-FUS(375-526)[P525L] | 1.95 |
| HA-NES-β23-tGFP-FUS(375-526)[P525L] [R/S in 375-422 and 454-526] | 0.75 |

TABLE 32

| Threshold Mander's co-localization coefficient of 598987 with G3BP | | |
|---|---|---|
| Protein | Co-localization coefficient | Inverted co-localization coeffecient |
| HA-NES-β23-tGFP | 12.8 | 4.1 |
| HA-NES-β23-tGFP-FUS(375-526)[P525L] | 7.8 | 1.9 |
| HA-NES-β23-tGFP-FUS(375-526)[P525L][R/S in 375-422 and 454-526] | 7.7 | 2.4 |

The invention claimed is:

1. A method of reducing the size or amount of protein aggregates in a cell comprising contacting a cell with a compound comprising a modified oligonucleotide, wherein the modified oligonucleotide comprises at least one 2'-fluoro modified sugar moiety, and wherein the protein aggregates are present in the cytoplasm of the cell, wherein the protein aggregates comprise an RNA-binding protein, and wherein the RNA-binding protein is PSF, thereby reducing the size or amount of protein aggregates in the cell.

2. The method of claim 1, wherein the RNA-binding protein comprises a mutation.

3. The method of claim 2, wherein the mutation is a point mutation, an expanded repeat, or a deletion.

4. The method of claim 2, wherein the mutation causes protein aggregation, liquid immiscibility, and/or mislocalization of the protein in a cell.

5. The method of claim 1, wherein the RNA-binding protein comprises a low complexity domain.

6. The method of claim 5, wherein the modified oligonucleotide binds to the low complexity domain.

7. The method of claim 1, wherein the RNA-binding protein comprises an RNA recognition motif.

8. The method of claim 7, wherein the modified oligonucleotide does not bind to the RNA recognition motif.

9. The method of claim 7, wherein the modified oligonucleotide binds to the low complexity domain with higher affinity than it binds to the RNA recognition motif.

10. The method of claim 1, wherein the protein aggregate is a messenger ribonucleoprotein granule.

11. The method of claim 10, wherein the protein aggregate is a stress granule.

12. The method of claim 10, wherein the protein aggregate is a processing body.

13. The method of claim 1, wherein the protein aggregate comprises G3BP protein.

14. The method of claim 1, wherein the modified oligonucleotide is a gapmer, wherein the gap consists of linked 2'-deoxynucleosides and the wings consist of linked nucleosides comprising modified sugar moieties.

15. The method of claim 1, wherein at least one modified sugar moiety is a cEt modified sugar moiety or a 2'-MOE modified sugar moiety.

16. The method of claim 14, wherein each of the linked nucleosides of the wings comprises a 2'-fluoro modified sugar moiety.

17. The method of claim 1, wherein the modified oligonucleotide comprises at least one phosphorothioate internucleoside linkage.

18. The method of claim 17, wherein each internucleoside linkage of the modified oligonucleotide is a phosphorothioate internucleoside linkage.

19. The method of claim 1, wherein the modified oligonucleotide comprises at least one modified nucleobase.

20. The method of claim 19, wherein the at least one modified nucleobase is a 5-methyl cytosine.

21. The method of claim 1, wherein the nucleobase sequence of the modified oligonucleotide is not 100% complementary to a pre-mRNA or a mRNA in the cell.

22. The method of claim 1, wherein the compound comprises a conjugate group.

23. The method of claim 1, wherein the protein or protein aggregate is not a prion protein or prion protein aggregate.

* * * * *

SEQUENCE LISTING

```
<160> NUMBER OF SEQ ID NOS: 5

<210> SEQ ID NO 1
<211> LENGTH: 112001
<212> TYPE: DNA
<213> ORGANISM: Homo sapien

<400> SEQUENCE: 1

ctcaccagct caggggtagt gactggacgt ttgttgcaac atcggagaat gcacgctctg     60
```

```
ggctgcagca ggagataccc tcaagcacag aaccaaaagg gttcacccta agcggcaggg    120
catcagcgat ggagaggccc gagagcccta gcgcccagct ccttttccca cgtttgggaa    180
ggcgcagaat aggtcgatgt agagcaagga gtgagtctca ggtctcagtc ctttggcttg    240
ctcttagggt agcaggcgag gagtggcacc agtttgggga ctctctcccc gcgttctgta    300
agaatcggcg gcagccagca ggcggggagg cgggggcacg tgtttggatg tgggtgcttg    360
tgtaaccagt tccccaagcg ccagccccga cagcgctcct tcgggaggct ggtccgagcc    420
cctgtttccg ccgcggcgca ggaagggttg gggttccgct gcctgcacca ggcaagagca    480
ccccgagcaa aggaagaaga cgacttgcct ccggagctat cactggggag tgggaatttg    540
gaaagttccc caactaggga cacacgtgac ctccttcgga aagtagttcc gactgtggcc    600
cgtgtatcct tccacctcct tttgaaccct cctaggtctc ctcgccccgc ccactcgctg    660
ggctgcagct tcctaccgtt ccgtactttc cactcaaccc ggtaacccca aacgtgcacg    720
gtccggccgg ggcgcgcgga gcctggcccc gggcgatcca tcctgccggg ttttcacggc    780
ggccaagggg gggcggggct aggtggtctc tgagaaccga gcttgactcc gacgccgcga    840
accgacctgg agcccgaggg gaaagatgct cgactctctt gggggcaccg gagcgggcgc    900
aggagaggcc tgcggggtgc gtcccactca cagggatcct ctttcagttc atttagatag    960
gtgccctttg ggcccttgaa attcaacggc tatgtgttca cgttcagcac gctcggctga   1020
gagctttcat ttttagggca aacgagccga gttaccgggg aagcgagagg tggggcgctg   1080
caagggagcc ggatgaggtg atacacgctg gcgacacaat agcaggttgc tctttgtgct   1140
aagactgaca ccatgaggac acagatttgg gggaaggggg aatctctagg caaaggctgt   1200
tacagtcaaa tctctgcgaa cgattgtgat ccgacagcgg tgcaaaagga aagagcgaat   1260
gcagtccacg ccgcggaaat ctaggggtag aggcaagggg ggagggtatt ccccttgcag   1320
ggaccgtccc tgcatttccc tctacactga gcagcgtggt cacctggtcc ttttcacctg   1380
tgcacaggta acctcagact cgagtcagtg acactgctca acgcacccat ctcagctttc   1440
atcatcagtc ctccaccccc gccccacaac agcctaccct gcctccggct gggtttctgg   1500
gcagaggccg aggcttagct cgttatcctc gcctcgcgtt gctgcaaaag ccgcagcaag   1560
tgcagctgca ggctggcggc tggaaccgg cccgagcaag ccccaggcag ctacactggg    1620
catgctcagt agagcctgcg gcttggggac tctgcgctcg cacccagagc taccgctctg   1680
ccccctccta ccgcccccctg ccctgccctg ccctcccctc gcccggcgcg gtcccgtccg  1740
cctctcgctc gcctcccgcc tcccctcggt cttccgaggc gcccgggctc ccggcgcggc   1800
ggcggagggg gcgggcaggc cggcgggcgg tgatgtggcg ggactcttta tgcgctgcgg   1860
caggatacgc gctcggcgct gggacgcgac tgcgctcagt tctctcctct cggaagctgc   1920
agccatgatg gaagtttgag agttgagccg ctgtgaggcg aggccgggct caggcgaggg   1980
agatgagaga cggcggcggc cgcggcccgg agcccctctc agcgcctgtg agcagccgcg   2040
ggggcagcgc cctcggggag ccggccggcc tgcggcggcg gcagcggcgg cgtttctcgc   2100
ctcctcttcg tcttttctaa ccgtgcagcc tcttcctcgg cttctcctga aagggaaggt   2160
ggaagccgtg ggctcgggcg ggagccggct gaggcgcggc ggcggcggcg gcacctcccg   2220
ctcctggagc ggggggggaga agcggcggcg gcggcggccg cggcggctgc agctccaggg  2280
agggggtctg agtcgcctgt caccatttcc agggctggga acgccggaga gttggtctct   2340
ccccttctac tgcctccaac acggcggcgg cggcggctgg cacatccagg gacccgggcc   2400
```

-continued

```
ggttttaaac ctcccgtgcg ccgccgccgc accccccgtg gcccgggctc cggaggccgc   2460
cggcggaggc agccgttcgg aggattattc gtcttctccc cattccgctg ccgccgctgc   2520
caggcctctg gctgctgagg agaagcaggc ccagtcgctg caaccatcca gcagccgccg   2580
cagcagccat tacccggctg cggtccagag ccaagcggcg gcagagcgag ggcatcagc    2640
taccgccaag tccagagcca tttccatcct gcagaagaag ccccgccacc agcagcttct   2700
gccatctctc tcctcctttt tcttcagcca caggctccca gacatgacag ccatcatcaa   2760
agagatcgtt agcagaaaca aaaggagata tcaagaggat ggattcgact tagacttgac   2820
ctgtatccat ttctgcggct gctcctcttt acctttctgt cactctctta gaacgtggga   2880
gtagacggat gcgaaaatgt ccgtagtttg ggtgactata acatttaacc ctggtcaggt   2940
tgctaggtca tatattttgt gtttcctttc tgtgtattca acctagggtg tgtttggcta   3000
gacggaactc ttgcctggtt gcaagtgtca agccaccgat tgctttctta ggctatctat   3060
atggtctctt cctgagggct attgtccgtt aatacagaat acagtacact gttagtggat   3120
tagcgagctc ggtaatccgg tctcctaaat gaacaaaaaa gtagacgctt tttgaggttg   3180
agcatatttc gattaaatct tggcttaggc cctagatcaa gggtttagat cagaataaaa   3240
tgaaaattag tgttgcacgt acgcatattg catcagaatc ttgcagtgat tgttttagtt   3300
tcctgagttg cattgataga ttcttttaaa atatgactga tttgcataac tttagaagca   3360
gaatcatttt cagtatatat ggtgcacatt gagggcaaaa agtagttttg ttaatgttta   3420
aacttaagtt acctacaact ttgaactgta tgtagaagtt ttgtagtttg aagtcaatag   3480
tgccataata taccttataa ggcgttctta ctagatcttt gttatattta ccttttctc    3540
tccctatggg gtgatgtagg atagtgcttg aaatttgcac ttcagtagca tttaatgttc   3600
agtgctcttg tcataaacat agaatggata ttgagtagtt tctgatccca gatggtaatg   3660
tgtaggttca agggtattgt gtgtagcaag tgaagattgc agaaataaaa cttcagttca   3720
tgcttgaaat ttaagtattg ttgtgatgcc agaattgctg ctcaccgttt ttaggtttca   3780
ggtcctctga caccttttgg tatcgttaat tttactgatt tgtgtagaat gtcagttgta   3840
ttttaccagc taatatctag aaatgctggc aagaggggtt tactccagct ttagattgta   3900
ggtatgttag ctttttttcat acagtgtatt aaatttactg agtcagcttg ctgaataaga   3960
cagaagccca agaattttaa cagtgtgtag ctttagttgt ctaaaagtta ggccttcggg   4020
cttcaaaagt tagtggtcat cgaaaagcat taatctttgc agtttcaggt acaacacatt   4080
ggttttgatt agggatgggg atggggccct ctttttgcag aatggggaaa gtattgacag   4140
gaattgagag ctattggtag gccagtgtat aaggtatgtg aaaacagaat taagttattg   4200
gtctgaagtg actgaagcat ttaggctcta tcaaggccta aaatttggta atatgagttt   4260
ggtaatgcga attgtggcag tggacaatat ttagttaaaa ttatgtaatt gcataagtac   4320
tagcacagta tttttaataa aagttatttc ttagcaaatg tcagttgcat tttgtctaaa   4380
ggtagagtga cactacagtg tctatatgtc ctgctaaaaa ttgtggggaa tattttttt    4440
taagacagcg tttatatcgg gagaggtttt attccgttgg attatgttag ctgcatataa   4500
atgtgcacag ttaattttgc ccaagttttt gttttgaaat gaatgtaaaa cttactgaag   4560
aagtagcttc ccaaaattta gttttctgtt aagccaaaaa tattatttta aaagagtatt   4620
tgcaaatttt gaagttgaca ttaattgaga atgttactaa ggctaaactg gacccgcttg   4680
cccagaagat aattatggaa aaattctttt gtgacttcca aagcagtcta ctattagcat   4740
gaattactga cagtcatcca aatatatagg aacaaaaaat taaatgttta tgtaactttg   4800
```

```
aaaaaaaagc ctttgaagaa aataattgaa tgctgtctgg gagacagatt tctttcagca   4860
cttaaagtac ataacacact acttttactt ttcccacttg attttaaatt atcagggtta   4920
ttaagacctt aaaattattt taccaggttt ttacatgtga gctgtgacat gactggcatt   4980
ttctttgatt tcagcgtatg ttggtctcta cacatgaaat ttgtgtgact taaaactttc   5040
tctaaaactg tacttttagt tatgatatgc atagaaagca gtatcaaata ttgcgtcaaa   5100
tgactaataa cacttaattt ctagagttgt ggttttattg agccaaaagt tgatatgaaa   5160
aaaagtcagt aaggaaagtc agtgaagtgc ttgctttttt gataattgca ctcccaataa   5220
ttttgatatt ccaacgtact tggtttgctt gttttcacgt taatgttttc tgtttattgg   5280
agtgggaagg cattaaaatt gtcattgaag actttgtctt tgacatgttg tagtatttat   5340
ttcagtaact aacctgtgaa aagttaaatt cctttatgaa agtagtgatt ggagtatttt   5400
tatctgataa agaaagatta ataatgaagc catttctccg aggaaaattg aggacaataa   5460
ttcagtttta aaatattatc gcaaaattaa attattctaa aaatttgtta gtagggttat   5520
atgcttaata ttagtctgaa atatagtgct gaatttgaga ctatagaaaa attaagtgta   5580
tttagggtat gtggaaacgt taggcttctg ttgtattttt attgtttggt agatttgcct   5640
cttttcaaat aaatgttcac agggaatact tttaacttgt agagagtaca gtgactattg   5700
aagttaccta aattacctca aggtaagtga ttactgaaat taatcatgag ggttttaaaa   5760
agtattctat tcacaacatt tattttacat tgttttgtat ctgctaagtt atatttcctg   5820
aaaaacatga ctggaccacc taattgctgt atgataactt acaaacttca tttttcatag   5880
tgcttattca agtgtaaagc acaactgaaa ggagtaatgt acagtttata tgaggaaaaa   5940
ggaattttat tgctgccagt gtaaaagttt gcacagcagt atagtcatca atgcagattt   6000
acattgctta taatatacta agtaaatact aaatgattaa agataataaa atatggtgag   6060
gtataaccac cttcatttta aacttagttt tagaagatag taaagaaaga ttcctttatt   6120
acctttttag aattttattt ttaataacat gggaaaggca actggtgata ttttaatttt   6180
tgtatggaac agtgcatctg ctttctcata gccacataaa atacataaac ttcttagtgt   6240
tatgaaatgg cttacttttt ggaagtgaag aagtcttcaa ttcttatttt ctaatgttat   6300
tttgaaattt gcctccattt gctgtttgtt catttggtga tagcgcaaca cttaaaaaaa   6360
tattttaagc cgcttctgaa gtaatcactt cagtgacttt taatggagga gtatttgtta   6420
tgggaaattc acttcacaaa gttttaacat taattcactt gaagtaaacg tgctattttt   6480
aaattttcat ctcaatcttt taagtaagac gaaagcttag gaaatcactt ttattattga   6540
tattgtgtgt gacttcagag tttgtaaaga gaattgtaga agtgttgcat gcatatgaca   6600
attttctgct taattgaaat gtgaggcctc tgccatacta caaggattta gcttccagaa   6660
aatgtaatat taacatagct taagaaatgt attttttttt ttctgtagaa accgttgggt   6720
taaacaaaca gttcagaagt tttattacat ggaacccatt agttcttaat cttgttacct   6780
ttttcttcat tttttctgtt aaacttgatt ttcacagtca gcattgaaga attcatcttg   6840
tggcctgaat tcattaagaa aagatgttag gatttgttct gaagatagtg acttaggaaa   6900
tttgtgagac tggggtcagt cagttctgtt ttacaattgc tttctatttg gtagctttga   6960
aattaattta gttgcttatc agagagaata atgttgaggt tagactaacc ttaaattggt   7020
aaggctttgc tgagcaaact gataactgta agtcttttat agggtgcatt actgccacat   7080
atacgttctt ccataggtgg ttaaaagtat attggtctgt gtttggtgat tctctttgta   7140
```

```
catattgagt atatgcattc actaatgtaa aataatttgc caagaaaggt gaaattagta   7200
tattgtactt gactattcac ctttccctta gtttttgaa ttttttcat tggttgcaga   7260
ggaagtatta gcaatttaat tcttttaaaa taatttgcac tggaataaat aagtatcggc   7320
aaatataaga agagtaacat aatttaaggg tgaattaatt ttatttggga agttttagtt   7380
ctgtatagtt aaggcagatt cttcatttgc aacagttgac attgggacat gtgtgaacat   7440
cttcaaggta ttaggacatc ttcaaggcat tactttttgg cagtgttgag aattttttt   7500
ttttttttt tttttgag atggaatctc gctctatcgc ccagtctggg gtgcagtggc   7560
aggatctcgg ctcactggaa cctctgcctc ccaggttcag gcgattctcc tgcctgaacc   7620
tcccaagcag ctgggattat aggtgcatgc caccacgccc agatagtttt tgtactttta   7680
gtagagatgg ggttttacca ccttggccag gctggtctca aactccagac ctcaagtgat   7740
ccgcctgcct cggcctccca aaatgctggg attacaggcg tgagccactg cgcctggcca   7800
gtgttgagaa tattgagaga tggatattgt agctgtacct gccatcaaaa gaattttctt   7860
gacctccaca tagtgtgaaa aagaagactg tttacacatt atattttaag taattataca   7920
cataattatt atcagtactc accacttcaa atatgaacag tgaatctaac cagtgtttga   7980
tttctctgtg tgtgtatgtg tatacaaagt tagcaaacct tttatcttaa tatttattaa   8040
aaaacgaatt tttgtttctt taaagaaaag actaccttag agaatattgt tctatagttt   8100
ttaaatatgg tcagatctat tttaaattat gttaaaattt tgagtattac gtttatctat   8160
acttttaagc atatatacat tgtttcattt tagattttag ggaggcagtg tgggctctgg   8220
agccagactg cttgttttgt aatcctggat cttccattta gtagctggat gactttgagt   8280
aggttattta gattttctca atctatttta tctgtaaaat ggggatgata atggaaccta   8340
ccgcatacgt ttatcttgaa tagtaagtga gataataata agtaatttca tttagcatag   8400
tacctgccac attgtaaata cttaaatggt agctactgct ctgaaaaact gtaatttcag   8460
gttatgtatg tagggaaatt atttgtattt tcatttatgg tgtatgattg taactgaatt   8520
tcctcagttt gggccatgtt aggattttgt ttcaagttat aagtgttttt aaaaataagg   8580
gtattccttt aggaagtctg ggtatgacat gtctgtgatt ttgctggttc atcacaaatg   8640
ggaaataaat ctctgctaac tcaaactgtt gaccaaagta aaattaatta tgccaatcaa   8700
aaactatttg ctttaaaata taaaaggcaa aaacttccta ttagcataat gaagtagaat   8760
ttttaaactt tgttataatc ttaaattttc tttagtgttg aagataggtc aacttaacta   8820
tcatacattt ttattcacat aaagtaaact ctgcctcaaa tgtaataaac ttaatatgag   8880
ttatgtaaac tttggtcaat agaggtatat tttttagcat ttccttttga aaatttcagc   8940
cttttgaggg agtcttgcaa ctgaatgtca agttacattt attacaataa aatggacact   9000
taatataatc tgtaatgcat taacataata tgggaacttt taaagtattc agtctctgta   9060
ttattgagtc ctatttccac atttggccag gattctcaat atgatttagg cccaagacgt   9120
gggaagaaag aagtaaagaa ctaaaggatt tttttcttca ttttttttaat tgaatatggg   9180
gaaagatgga ataagcttat ctgtccagta aaggccatta tgtgtacata gggattatta   9240
tttttccccc ccttgggctg tactgatttc ccagatgtac cacagcactc ttagtagtga   9300
agcacttgac ttctagtgag tggatttttt gtgtgtgtgt tttatattgc agagtgaata   9360
cactctgtct gatactatgt gactttctga ttatgtgatt tttatgcatt ttatgtgttt   9420
tgtaaactag ctgtattttt ggtccatgtc taggttgtag aattgaattg tgcattttgg   9480
catctgagca cagctgagtt ttctaaatca atctctctcc ttgcacctag tttttgcttt   9540
```

```
agatcactac ctaagactta ctgttgattt aatattagag cacttaagca tagctttgac   9600
ttttatttcc tttgattttt gtagattttc aggctgaagt acaataaggt tctctgttct   9660
ttactagtaa ttgcaaagat tgtattctgt gaattttatt tgtttaatac ttttgatctt   9720
ttgaagagga tgtaattatt taaggtatta tgaaatgcat tgtgatttga attagatact   9780
ctttggagat ggagttttgc tgttgttgcc caggctggag tgcaatggtg tgatctcggc   9840
tcaccacagc ctccgcctcc tgggttcaag caattctctt gccgcagcct cccaagtagc   9900
tggaattaca ggcatgcgcc accacgcccg gctaatttta tatttttttt ttcagtagag   9960
atggggggtt tctccatgtt ggtcaggctg gcctcgaact cttgacctca ggtaatctgc  10020
ctgtctcagc ctgctaaagt gctgagatta caggcatgag ccactgcgcc cggcctcaga  10080
tactctttta attagatgcg tttaaaaatt taacccacca ttgctggcat gaatagatgt  10140
atttttagag tgattcataa atatcgtata catgtttaaa gttacaaact ttttgcttat  10200
ttcaaaatgc aggattcttt tccatttaaa attccctctc tttgtgagac ttctttttga  10260
gtattctggt tactctaaac tgattggaga tgaaattaga tagaattgaa aactgtactt  10320
ttaaaatgaa attttgggga tgtcattaag cttgattttt taggtttttt ttttagtgtg  10380
tattataaat tattttacac tgattgtcag cgataaaatg gaatgcctgg gatttttttaa  10440
aatttatttt attcattttt ataaggtaaa aacagtgttt tgctaggctt aatttgacca  10500
tgttgtaaaa tttattgtat accttgaaag aatcatttat gaaagatact gaattagcta  10560
atatatactc tgtcttatgt agtttttgat taacaataca ctttttaaat cattagctca  10620
tttgattttg caaagaagaa caggtaacct aagaggcaga cagaacaggc attactttta  10680
tttttctttc ttttttattt tatttattta tttatttatt tattttttgc agcttaggaa  10740
ttgtagctcc agtggaatca gtatcttgtt aatggctagt gaaagactga gtctgaagaa  10800
ggatgcagga ctttttttggc acttggtgca gtatttttcc cattatgtta catgagtggt  10860
tcttaaactt cagtgtgtta gaacaacctg aagggcttat taagctatgg attgcttact  10920
ccaccctcag agtttctgat tcagtaggtc tggattggga cctgagaatt tttatttctt  10980
agaagttttc aagtgatgct gatgctggtg ctctggggat cacactttga ggaccaccaa  11040
tgaacattat ctcccaccaa gcaaaccctt aacatgttat actcctttag gttattagaa  11100
tttatacatg cattatttca tttgacctgt aaactctaag taactttgca tggaaaatgt  11160
tatcctgatt ttatagacga gatagtgagt ttagaaaggc agtatggtgg aatggagcat  11220
agatttggag ttggctagac ctaaagtcca gattaaatct ctgctcaagg ctgggcgtgg  11280
tggctcatgc ctgtaatccc agtgctttgg gaggccagcg ttggcagatt gcttgagtct  11340
ggaagttcga gaccagtctg ggcaacatag gcagaccctg tctctacaaa aaaaaataca  11400
aaaattagtc gggtgttata gtgcgcattg gtagtcccag ctactgagga ggctgaggtg  11460
ggatcacctg agactgggac tttgaggctg cattgagctg tgattgggac actgtactcc  11520
tgcctgggtg acagagtgag accctctctc aaaaataaat aaataaatac atccccgctc  11580
agccacttat cagttacgta gatacactgc ctaaccttag tgaaccctgt ttcgacaact  11640
ccaaaatggg agtaaaaatc ctaaacttgt acagtggttt tttagttttg ttaaaagtac  11700
aggtgaggtt tttttcagag tattggttgc catctgagag tgatcccctt tcacctcctc  11760
taggactttt agcattttct ggagacattt tggtggtcac agctggggtg gtagagtgtg  11820
ctattggcta ggggcttgaa gccagtgatg ctgcttaaca tcctatatgg cacaagaccc  11880
```

-continued

```
ctccccatca acaaagaatt atctagccca aaatgctgtg taaaatgtct ggtatataat  11940
aagtataata tttgatgaaa atcagtacct ttgcccccag gtgtgatatt taagaaggtc  12000
aacttactaa atcagtgatg gagttagtcc taacatctgg gtgttctgac tgctgctagg  12060
ccagtattct ttatatgata ataagaactt tgtccacaga agatatccct aataacaaaa  12120
aaggtttatt tgaagaggac tcatgtgttc tttggctgat tgtgaaagtg ttgctttgaa  12180
cttctgttag aaaaggttga agatgttttc cgtaagtgtt tttaatactg tacgtagtat  12240
tcagaaggat gtttaatttt ttttttaatt ttgctagtag tttttaaagt aatccttttt  12300
cctttaatta tgtagttgtt gaactgttgg gagttacttt tctcttacta ttttgttatt  12360
taatgtattc tttgacctta tgctttttta ttctaaagct gcttttatta tagtcagata  12420
tgatgaagtt aaatgtacaa tgtaaaattg caaatttcca acgagctata caaacttaaa  12480
tatttctaag taaagaaaat agggctgact ctaaggttct ttgatccatg tgttgcattc  12540
ttttctaggc cctaaatttg ctatgccagc ctgttgaatt aaagtgcttt atttatctaa  12600
attagaaact tgtattaaag tgaagtttta gaaaaaaaga aacaaaatcg gaatggagtt  12660
ttaggttagc ccagagatgg gaagatgcca agaaggtagc tttagtggat tctgaatttt  12720
ttggttttgt tttgttttta gggcaggcaa atgtaattac aaaagggttc taggaataga  12780
ttgctgtgat ttttttctg tttgcatgat tttacagttt gctttgcctc tcacttttga  12840
atgcagaata aaatgtcaag gccttatttt tttttaaatt cttaagaaat ttaagatttg  12900
actgttaatt ccttttgaaa tatgggatat tttgagatac caattattta agacaaatag  12960
gactcattgt tacaattcag ttgaataagg cttatgatgt ttatttcagt atatgaatga  13020
aaactatgtg cttattgtac ttaagaaaat ttcttttatt aaaaacatga ctaaagagaa  13080
ttttaaaaat cacccactgt cctacttctc taaaacttaa tgttttcata ttagcttcca  13140
gttttgttca tatgcatata ctttaaaacc tagttcatgg tgaacttaag agggtgttct  13200
ttttaaaaaa caatttccat tgcactttgt cgttgcctta attaaatggt gaaatcatca  13260
gaaatattta ttttcctata cttatacatt tattaagctt gtttccattt ttttattttg  13320
tgattttttta agtggattta agataaccta aacattagag aggattttca tggttttgat  13380
tcatgaaatc ataatgttat acaaacctaa ctgaagtgtt agagccttga agatttttcc  13440
cccgaattac atatagtaac tctacttgta tttaatactg aaagcatatt ttacttattt  13500
aagtgagaca aagtaaaatt tagctgaata ctttagatct atcatttcct tttcctgttg  13560
taagaacatt acattgtgtt gaaattaaag tggatataga aggtaattag aataaactgc  13620
cacatcattt ttatagtaaa gtggtaataa cactattgct ttctgttttt ttaatcagaa  13680
ggagtatggg cttataatga tgttactgtt ccctgaagca tattttgaat gatacggttt  13740
atatttgcac agttgcccag gtaatcattg tgatattaat tgatcaattt gctatttatt  13800
tgcgttttaa atcagtacta gtatttgtgc ttaaaaattt tgcatatgtt ttatcagatt  13860
taatttttaa gtgtcagata ctaaaacaaa taaccttaac tttattaaat tataattttt  13920
tatcatgagg tggtattcat ttattcatat agttagaaca aaaaatattt aaaatattga  13980
ggtagaaaca aattagtctc tttttaatta aaagccagat tacttgttag agtaacattt  14040
tcccaaatga ggtaaaattg ttgcgactgt taaacttaag gaaattttga tctaggtgtg  14100
gtatatacct tcttgtgggg tgctaatgaa aacagggatg gcaaaaatat tttgtttgtg  14160
agtgtatgca tttatgcttt ttgacaacct aagaaacact cttacatctg agtatctttc  14220
atggactagc tgtaggaaat ctatataaaa tagcttagta tactgaaagt atgacatagt  14280
```

```
tttacatatc tagattgtgg ttgtgattat atataatact ataaaatatg ctaacgtgct  14340
gcttaataat actatttgga tttttttaa tactgaaaag gtcacacaga ttgtgattat  14400
tgtgtagtgt ccaagaacta aggcctacca tctgttactc aaatgtatga aaaagttaag  14460
ataatttagt gatataagtg gttttgacac cactgttttt ggaataatct aattatgatt  14520
tttataaaga ctaatatcaa attttaaacg tttgcaaaaa tgaaacctaa tagttatact  14580
gttatttata tttttctatt acaatacaga tactggctga gaactaaaga ttgtgtaata  14640
aacgcctggc cttcagtcat ttggtttttt ttttccctcg attgtttgga tagttaactg  14700
gacatcatgt tttaacttga gaaattaagt tatacaagat tttgatattt taaactagtt  14760
ttcctaactg gttgagatat ataagaattt agtattacag gactcaatca gggaactgat  14820
ttaataagaa tttcttaaaa atttgtttaa atatttttca agttcttttc ttcatcttct  14880
acaacttaat tcttgtctgt atgcaaatga gcttccccat ttaaaatttt gctgttgcat  14940
tttaggccac tatagaagtt gtttctttaa ttttcactca caagaatttg gtcttaccaa  15000
attgtgtaaa tctttaaaat tgtgtatttg gcttaatatt atagaatctg attgatttaa  15060
tctaccttgt ttcatttagt atgttgacat tttcttgaga aatttgttat gccaaatgat  15120
taacataata atattttaag tttagatatg attttgaatt tacattttca aatgcaactt  15180
tgtgtctgtg gccttttttt tttttttttt tttacgagaa acatcttgcc aattttcaga  15240
ttaatctgtg aggaaagtag attggtttac tagactcagt ttgtagactt tggtgagaac  15300
tgaattggag gctatgaaaa aaataccttt tgggcctttc tgaatagaca tatatacata  15360
aattatatct cttacattaa gtgaggcaca tatgtaggtg agatttttac ctgaatatta  15420
aaagtttaaa agtcgttacc tattctgttt acttaatagt atttaaaggg tgtgagaggt  15480
gttatgtgtt tctgtccctt gtttttattc ctatccctcc catctaactg ttggtactct  15540
tatcttccca ggtattaaac ttgtatgttt taaaagctta tttacttgtt gaaatggtta  15600
acttaattag tttttcttt gaagtttcag cctaaatatt ttctgttttt ttatatgtcc  15660
tttaaatatg aaaattctac agctaatcat aattagtaat tgtacttttt cccctattac  15720
aataactggt ttcataataa aatggtatcc cttcaataac aagcatttat agtagtttat  15780
taaaactaag ggtgttatct attcaaacca agcaatgcag acttactgtt gactctgtta  15840
atatatttta aaattgcata ttactaaaat ttaaaatatg attttgacta gtattttggt  15900
gtatgttatt ttagatattt tgattatgca ctacttaaga atgaattgtc aagtatgatt  15960
ataaagttga tataatagtt aaccttcagt gggaatagga atcatttaat attgttagat  16020
atttgtatta ttagaacaat ctcctatgat tcttactaat atagtaatga atgacagaca  16080
atatgttggc tttcatattt aaaaattcac atgcatttct agtttatgtt tttcttcgac  16140
taaaattctg cagcacttag gcaaagctat ttttaccagt tggaaaaaaa gtaagtcatt  16200
tccaaccaat tttcctggct tgtagtatag aataaagaga cttgatttta ttacattaaa  16260
gccaaatata aaatgatgca atctagcaca cacttgtttg gaacttttct cttttaaata  16320
ttcagattaa gaggacgttg aaaggtaaat tttttttttt ttttgagacg gagtctagct  16380
ctgtcaccca ggctggagtg cactggcacg atttcggctt actgcaagct ctgcctccca  16440
ggttcatgcc attctcctgc ctcagcctcc cgagtagctg ggactacagg cgcctaccac  16500
ggtggcgccc ggctaatttt ttgtattttt agtagagacg gggtttcacc gtgttagcca  16560
ggatggtctc gatctcctga cctcgtgatc tgcctgcctc ggcctcccaa agtgctggga  16620
```

```
ttacaggtaa attttgattg ttattagcaa ctataaaagt tttgcagttg gcttattgga  16680
aaaagaaaac ctccttgccg gagacggaga cgcatttgta ttagaacttt gttttctgag  16740
taccttacct atagtaggtt tcaaatattg gtgaattagt tgatggttag gtctgcataa  16800
ttactgcgta tggaaattct ggaaccctat tttttcaaaa tgcagctaat gttgagagaa  16860
tatgcactaa atattactag atctttgttt ttcaagatgc tgatatccct taacatcttc  16920
tgcactttac ctgtttgaat atcttttttg ctgtaaaaat tagtggcctt atgtctttct  16980
gcataattat agagtagcca aaacctgttt taggttaatc acctctggca aaataaatga  17040
taaaagcata gcttttgtaa gcagaatgat attacagaag ttaacttata aatctaagtg  17100
tattaaagac acttaggaaa tttatgataa tgctgggtca gcattacagt tttaactttt  17160
tacagttttt catatgcttt ttttgtgatt ttgctgtaga aaattaacag ttggcatttg  17220
gcttagttca agtataatgc tgttgacaag tatatctgac acgtcattga actaataata  17280
tttttgaaag ctgataggta agttatatct attttgtttc attcgtcatt agtgatcggt  17340
cttagatgtt tttagcgaga gcaaaactgt agaggaatgt gtgtctgtgt gtgtatatgt  17400
gtgtgtgtgt gtgtgtattt taacagcagg agagttctga aacaggaaac cagtcttatc  17460
atattcatcc agagacctag gaagaaggta attgtttggt atactcgtta aaaccagttg  17520
gttgggcaac ttaaattttt agaggatcac agatgtaggc ttgagcagtt gtagatagat  17580
gatttctttt tttttctttc tttttttcttt ttttttttgag atagagtctc tctctgtcat  17640
ccaggctgga gtgcggtggc gcgatcttgg cttactgcaa cctctgcctc ccaggttcag  17700
gcgtttctcc tgtctcagcc tcctgagtag ctgggattac aggcgcatgc tgccatgccc  17760
ggctaatttt ttgtatttta gtagagacgg ggtttcaccg tgttccccag gctggtctcg  17820
aactcctgag ctcaggcaat ctacccacct cggcctccca aagtgctggg attacaggcg  17880
tgagccaccg tgtctggcga tagattattt cataattaac acctgctatg aagaaaaatt  17940
gattaaaata gttgagaagt ctagtacact ctcagctaat atactaaatt atactatgga  18000
ttttagagta ttgttaacat tatcagtgac ttgatatctt cctgaggttc taatttgctt  18060
aactttaaat aattggggtt cagatcacct tgattgttcc cttaaagatt aaattttgta  18120
aaactgtgtg taattttcct gtatctggtt tggatagctt taaaaatggt tcttaagttt  18180
aatgagttca actgggaaaa aagttagttc tattttagat gttgtgtcac tggaaattat  18240
gtttccctgt ttgttatatg cacattatta caaagttgta atcaatgttt tcatactgtt  18300
ctctggtctg ttttttttcac aaatacactt tttatttgtc gccaggtact tatttttaaa  18360
gctatagagg taatatttca tcaggtgagg gtaactacca tggtttgttt gctatactgt  18420
gttagggtta ttttcgtttt ttttttcttt tataaactat agttgtgaat atgtttatgt  18480
agtttacttt tggtttatta gaatatattg ctagagtggg attacaggat taaagagtgt  18540
acagtatttt agtttttttt ttttttttac aagttgcaga tttgttgcca aatgaacgag  18600
tttgtagtat tgctaacaag gagaagaatt actagcaagt cttgatgtta cttttgaaga  18660
gtgtgatgat tgcatttagg aagatatcta aacttctgtt tcaaagcaaa aagtatgtgc  18720
aaatttctta ctcatgacaa attcatataa tataaaaaca tgaaagttgt gaggtcaggt  18780
tgtttggaga agtagaaaac ttcagtagag tttatagata ggcagtcttc ctttctggtt  18840
tggcactgac agcagattaa ctagaaagtg ttagaaggaa cctaaaattt atactaaagt  18900
caatttaagt taattaatat accagaattc cttcttttac aatttattta taaaaacacc  18960
atattgagtt gccttgtaat gagacattta aactaaattt aaataacaga attcatgcac  19020
```

```
catctaataa caaccccctta tttacaatta tagagtcctt tgcaatttta tagatatttt  19080
catgtatccc atttggtcct tgaaacaatt aatgaagaag ttacagcaag tggtattatc  19140
attattttac agaagaacaa aacaaaaata tatgtggccc agagattgag tgatttacct  19200
gaggttatag gctttagatt gcatagctgg aagtagaacc ttgttcttct atattaaatg  19260
acaatattca ttaagtactt agcacaggat ttggtaccta gtaaatattt aaatgttcct  19320
gtgttattcc tgactattcc ttctttattc ttaaaacgcc attttttgag cactcttaat  19380
atttatagtt caaactttgt acctatgtac ctttttctct ttagaaaata agatttcagg  19440
ctgcattaat ttgatctgta caggaatgat tatatgtttt acatattggg acaaattgct  19500
cttttttat ataccttaag ctctagggta catgtgcaca acatacagat ttgttacata  19560
tgtatacatg tgccatgtta gtgtgctgca cccattaact catcacttac attaggtata  19620
tctcctaatg ctatccctcc cccctcccca taccccatga caggccctgg tgtgtgatgt  19680
tccccaccct gtgtccaagt gttctcattg ttcagttccc acctatgagt gagaacacgc  19740
ggtgtttggt tttctgtcct tgcgatagtt tgctcagaat gatggtttct agcttcatcc  19800
atgtccctac caaggacatg aagctcatcc ttttttatgg ctgcatagta ttccatggtg  19860
tctatgtgtc acattttctt aatccagtct atcattgatg gacatttggg ttggttccaa  19920
gtctttgcta ttgtgaatag tgctgcagta aacatacatg tgcatgtgtc tttatagcag  19980
catgatttat actcctttgg gtatataccc agtaatggga ttgctgggtc aaatggtatt  20040
tctagttcta gatcactgag gaattgccac actgacttga actagtttac agtcccacca  20100
acagtgtaaa agtgttcctg tttctccaca tcctctccag cacctgttgt ttcctgactt  20160
tttaatgatc actattctaa ctggtgtgag atggtatctc attgtggttt tgatttgcat  20220
ttctctgatg gccagtgatg atgagcattt tttcatgtgt ctgttcgctg cataaatgta  20280
ttcttttgag tagtgtctgt tcatatcctt cgcccacttt ttgatggggt tgtttgattt  20340
tttcttggaa gtttgtttaa gttctttgta gattctggat attagccctt tgtcagatgg  20400
gtagattgta aaagttttct cccattctct aggttgcctg ttcactctca tggtagtttc  20460
ttttgctgtg cagaagctct ttaggacaaa ttgttcttaa ataatgaaca gttggcactt  20520
tttcaactgg aaaattcaag gaactgctct ttctgctttc tgctcaatat gaatcttcaa  20580
tttagaaatg agagtccatc attaacaatt caacatagct tattaatagg aaaaaaaaac  20640
ctagtaacaa atgtaaaatc tttgattaaa tgagaaagtc atagaagttc atcagatttg  20700
tatttaaagc atgatttcat tagaaaagtt gataataagg atttaactgt gacataattg  20760
gaaaatactt gtttaaactt aaaattttga aaagaaatgt aaatgtgatg taacttatga  20820
atcagtggtt gagtttcttt tttgctcaca agaaccctaa ctgtgtgtta cttgaaagca  20880
ctgatggaaa tcagggaaaa agctccagaa gttcctacga aataaaatta aatgataaag  20940
tcctggtatc tgctaacttg ccttccattc ctgttatctt ttcttcttag tctgacttca  21000
ttaattcttt caccctggct actggtttag ctcagtgttt tatgagccag gcagcttcag  21060
actttgcttt tgatgctctt tgttcattac ctctaaagct gtattatcac tttcatttta  21120
tcattaatgt ttcatgtata tgttatagtt tcatattgtt actgcaactt ttacttagct  21180
ataatttaaa aaatatctgt gatctgtgga aataattatt ctatggcaga aaagtagtta  21240
ttgcatttta ctttataagt tgtttaagga taagcatacc tatatattaa gcactacaaa  21300
gaaactttta caatggcttt atttttagca aaccatcata gttaaaataa gatttagtgt  21360
```

```
acatgtcagg aacacagtct tatgaaataa ggtttaggga gctattttta gttactatat  21420
cctacttgaa aattgtagtt aaatttctag catataccct attaatttag atgcaagtac  21480
agatttgaga taaggtagat acattatttg gatgtcaact cggaagttgt tcaagaaaag  21540
atattttgtt atttagatgt aacttggaac atatttctag tgtttcaagt catgattgta  21600
tgcctagaac aggcaataaa aatttactta gctggtaaaa cagccacatt atttcaaata  21660
tagtttagtt atattatgga ttaaattgat ttttgtggac agactttaga acttaattgc  21720
tattaattac attttttctt tgggacggta tttgttcttt ggtgagaaag gattcttgta  21780
acacctaaat caagactgtc caaacatggc atatgcagtt taccagtcaa aacaaactaa  21840
tcacttaaga tctgtgtatt ttgttttatt tgaattatac ctcaattaaa acaaatttag  21900
catgtttaca caaaggtggg gggaaactgt ctaatatatc tgagatctgt tggagctggg  21960
gtgaccatcc aacttaggca agatagctag taccatgtat gcatttcttt tacctttctt  22020
attgtatata cagtaatcac tgatattatg agaaaaagaa ctttttaata attcaggaga  22080
tattttatcg ctagtatata ttgagtgctt attatgtgcc ttatatactt tggactcatt  22140
taatcctcaa cacaacaacc ctatgtagtt catactagaa ttattcccat ttaaagatgg  22200
ggaaagtgat gtttagagag gctaagtgac ttgcccatgg ccaaagtatt agaactggga  22260
tttgaacaca ggtagcctga ttcctaaata aatgaccact aacattaaaa agacataaac  22320
atagaggtgt ttgttgcaat gttagtcata atacctaaaa attgtgaact agttaaatgt  22380
ccaatagtag taaaatggtt cattaaccat ggtacaccca tcaatataat gttatattgt  22440
catttaaaat tgtattccca agtttcgtat caggaaaata taataaattt ttgaaaaatg  22500
taatgggata tattgtattt ataatacagt aatcactatg taaccaacat ttttatttcc  22560
atcaaaaatt agttataaag aaatagaaat ctaagaagtt taatagatat taccattgaa  22620
cactagattt gtattagtat cttttatatt tatctctctc atttcctata ttggccatgt  22680
ttacttttaa aatagtaaaa gtcataagct ctattttaaa aataaatgtt agtttattaa  22740
cccaagaata atagctaact ataaattcat atttgataaa ataaaaagat gacattcatc  22800
ataagggata catacctgtg ctagcatatg gcatttttaa aatcacatga gtaatttgta  22860
atcatcatag aaatattaga aaatacaaat aagcaaacac atactgaaaa tttagtgttc  22920
ccaaatctaa aacagagaca ctgttttttt cttttgggat tgtattttag atatgttctt  22980
aagttataat aaagtaaata cttaaaaggc aaattgatac attaaggatt tcaaagagta  23040
aaactttttg ttaagctttg atgttcttta gaaagtttag attattccac aagtcactgt  23100
cgttgaaaga aaagtagtta cagtggggtc ttatgggata aggcattacc atttgttcag  23160
ttgagagaca gctatcacta tgttttaagc attgttcata tattagctca tttaatcctc  23220
atagcaacct tatatgatag gtacctttat tagccccatt ctgcttagga agcaacagaa  23280
agagtatgta ttttgcctaa ggttgcacaa taagttaagc tggggttcca attctagcaa  23340
gttggttcta gagtgtatgt tattaaccat tatgccgtag tgcctgcaag tagatctcta  23400
gatgtcagaa atactcatct tcctctggtt acctggttgt tataaatctt tatgcttaat  23460
acttatgtca ttatatgtaa atttcgtatt aaacactcaa cttattcaga agaatatcag  23520
gtaagtgtag gttaaggctg ttttctatca gaaatcatta tatgtatata tattcctcag  23580
ttcttatgtt gtttagtttt tctaaaatgt caaattttat aatatatgga gaagtataaa  23640
tgtatattag aaagattttg tttatttgtg taatttgtgg cataagaaat atttgcctca  23700
agatttggtg cttgtttagg tagttgctgg cattactttt ggaaatgtca gtaaattttc  23760
```

```
atactgtctt ggaatttttt caatttttac attttattag taaatgtaat tacaggttag  23820
taaatcactt atttgaacct gtttcctttg aaagttttat atttttattt ggaaatagaa  23880
aaaccttaat ttcctctcgt tgggcagtat ggtgtcaaaa gcttgggctt tggagcttcg  23940
tatataatct gggttcaaat tataacttac tagttactaa cttgggcaaa ttacccagtc  24000
tttttgactc tcaatttctt tgtctatgaa atgtaatact atttaggatt gttaggatta  24060
aatgagaata tatttggcat actgtctggt acatgatact taacaggtac tagttgtcta  24120
catctttcta acttaggatg gatgccgatg tcttgggtaa catctcaaac tttatcagta  24180
aggaaggtga gaatctgaag aaaatgaaac cttaaaaaga ttgaattcct ggactccatt  24240
taaaggagta aatagctcac gaacaagact tgctgctctg caaagtcttc catgttgatc  24300
ctggtctttg actccttatc tgtctgatta aattgaattc gctgccgtgg catccttaaa  24360
gctggacctt actttgtcag tcctgccttc tccatgttgc tttgtgtgta agcttcactg  24420
gactgtttgc tttttgctga ttattttatg tatttccata tgtctacttt agcctttgct  24480
tggaatgttc taactgctct tgtttcttcc tctgtttact ggtttctgac ttaactctta  24540
aggattatct aatatattac ctacttggtg aaggtttatc tgtgtcccca cagaattaat  24600
ccttccctct ttaactctta agctatctta ttttttatct aatcgggtct ttggcacaat  24660
tataggtctg tgtgtctgtc ttccctaata gaataggaaa gccttgagga cagtagtctt  24720
tgcttactta gccttatatt ctcagtgccc cttgtgcaaa acgttcaata tatgtttgaa  24780
tgattatgtg aatgaaggag ggggccagct gaatttactt taatgattat gtaacaccca  24840
tttatgtata gttatagact tgtctgaaat gagttaaatc ctttgcaacg tttgctgcta  24900
tgctttgaat gtctcttaca aaactcatgt tgaaatttaa ttgccattgt aatggtatta  24960
agagatggaa cctttaagag gtgattagat aatggtatct ctatccttat gaatggatta  25020
atgctgtttg aatggtagtg gatgagttat cttgggagtt tggcctcctc cgtctcacat  25080
gcttccttac cttctgccat gtggtaactc aacacaaaga tccttgccag atgctgatgc  25140
catgctcttg gacttcccag tctccagaac cgtgagccaa atacatttct gttcattcta  25200
aactacctgt tttgtggtat tctagtaaag caacataaaa tttactaaga aaactggtac  25260
caagagtgtg attgttgcca taacaaatac ctgaaaatgt tcaaatggct tgggttctgg  25320
ctagagaagg atggaagagt ttggatgaac aggctagaaa aagcctgtat tgctgagaat  25380
agagcattaa ggacaattct gatgaggatt cagaagaaga gagctgtagg gaaaatctgg  25440
aacttcttag agagttgtca tcagttggta gaactataag tggtaaaggt ctttctgatg  25500
atatctcaga aatgaagaac aagatactgg acactggagt aaaggccatc cttgttaaat  25560
agttgcaaag aacttggcga aattatgttc atatcctaag actttatgga atgcagaatt  25620
taagagtgat gaactaggat atgctgcaga agaaataact cagcagcaga gcatttaggt  25680
tactggatgg ctacttttaa ccacttaaac taagctgggg gaagggaatg acttgaagac  25740
agaatttata attaaaagag aggcagaatg gaaatacttg gaaaatttgc agcctggcca  25800
tagtaaagaa tgcaaaaggt atgtttagga gagcaaacca agggtgtggt ccaggaacca  25860
tttgctgaag agattaatat tcctagagga gacccaaggg ctatttatca agacagtgga  25920
aaaagacccc agaggcattt tggagatctt tgaggctgcc tgccccatca caggcccaga  25980
gctctaggag ggcagaatgg tttgtggctc aggtggtcct tcacaagctt gctgcccagg  26040
gctacctcag ctccccatat ttcaacccag tgggccttgg ctgtcctagg tctggttcag  26100
```

```
aggggcccag gtgtggctta ggctactgct gagtactcaa atggtaaacc ttggcagcgt  26160
ctatatggtg ctaattctgc aggctcacag gatgaaagag ctgtgggaga catggctacc  26220
accaccagga tttcaaagga tgatggggat agtctgggag agacttgcca caggcttgga  26280
gcctctgaag ggtggaaatg tgggttggag tcactacaga gagtccctac tagggcattg  26340
cataatggag ccatggcagc aggcccacca ccaaagcttc agaactgtag agctacaagt  26400
atacagtgcc agcctgggag aacttcaggc ttgagaccct aacctgtgaa agctgcatgg  26460
gctaagtaca gcaaagccat ggaggtgggg cttcccaggg tctattggga tgaaacgaat  26520
gtattttgta ggtgagaagg acatgagttt tgaggcccag gggcagaatg ctatggtttg  26580
gttgtttcct tcaaaactca tgttgaaact tcattgccat gtggcattat tatgaggtgg  26640
aacctttcag aagtggttac attataaggg ctttgccttc attaatggat taatgccatt  26700
attgcaggtg tgggttagtt atctctggag tttggccccc tttttctcta tcatgtgctc  26760
atgccctctt ttgccatgtg atgccttcta ccatgttatg atgcatccag aagactctca  26820
ccacatgcag ccccttgatc ttagacttct cagcttctag aactgtgagt gaaataaact  26880
tcttttcttt ataaattacc ccgtctgtgg tattgtatag cagcagaaaa tagacatcag  26940
cctgaagttc ccccaggctg gcattaaata ctaattatta attagtattt atagtgcaag  27000
gataaattca agtttagccc tggttagaat gaccacattt caagggaggg gctttgtact  27060
tctgtgcata tctgtaagga taaaaatctt aatactattc tcactgaaat taatggttta  27120
ggttaggtaa ggttgttagt gctaataatt atttctttta ataaaatatt cttagttgcg  27180
ttgttcaaaa aacatagatg atttgaattt atatttttg gccaaaatat atttataatt  27240
ttgagtagga attccagagt attggtagct ataaccactt tgggttccct gccattgctt  27300
ctggtgcctc attttttctg acgtcttcca ttttcttaca tttgtcttct aaggtggagt  27360
taagattact cagttaagat tatttcactt taggcctctg ctgtcttctg cttttttttt  27420
taaaatgaat ggatataata tcccaataca ttttgataat tgaacaacag ctacattttt  27480
aagtgaggct actttcttct aattttttaa atttattttt ctcagttttt aaaaaaaatg  27540
tcagattggc taagagttgg ggcagctttc ttatgtgaga gtagtagatg acagcaaata  27600
tttgtgatgt taaaatgata atcctaatag ttttctttta gaatctttat aataaaaacc  27660
ctttgaggct gagggtgaat ttgtatgttc ctaaagtgac aaaaaatgtt cttggggcat  27720
agtaatttaa atcttagatg cttttattag tataattttt tggtagaaat ttggcattaa  27780
aaaatgcata cagagctttt tctacataca gggcaagaca gcattttgtc atggcaatta  27840
gtaaatagat aattataaaa catctaattt taagcaattt gttacagaaa cgatacaggt  27900
acattgtggc aaaaatagaa gatacaaaac aagcaaatat gagaaaaaat atacatgcca  27960
ccacctatat atgactttta gtactttata atcttttgtc tatatatgtc tatatggata  28020
tatacgtatt ctttttatcc aaatggtatt acattgtaca ttctgttttg aaacctgcct  28080
tttttagtca tttacatcta cttttccatc tcagtaactt ttcatcttgt gtaatgcccg  28140
gatcacatta aaatgtttcc aattagctca aaaatgtcct ttatggctgg tttggctaaa  28200
acagtatcca ggccagcatt gcacctatga aattggctgt taggaatctt gtatctttaa  28260
aaatcaaggg cagcaaccca tcctcccgct tcccccacct cccaccaccc ccccaccttt  28320
ttttttctt aaagatactg gcttgttgaa gagagaatgg gtcatgtcct acaaactgtc  28380
tgaatttgtc cagtttgctg tctcatagtg tcatttagct tgttttatcc tatgtatttc  28440
ctgcaaatta aaatttgtat ctgaatcctt ggtggatttg agttgaagat ccttaaccat  28500
```

```
catagatgat gctgtgtcct ttatattgca tgtcagaagt tacatgatct ttacttgatt  28560
catgatgagg agatggccac tgaaattgga cagtgacagt cttttctgcc cattgttcaa  28620
ttatattcgt ctctttacat tagaaagtat tttgggtagt agtattttgg tgctgtaaga  28680
aagttcattt tctcatcaac cactcaccta ttggtttaac accatttgtt gatctttgag  28740
tatatcagta atttcatcag ggtttgcaaa ataagacttt aaattctatt gttttacatt  28800
attaattgat gtttttgat aaggtagaac ttgtgaaatg ggactatttg tttgtcttta  28860
aatacagtct ctataggaaa gacaaaataa atacttaaat ctcactcttt accatttttc  28920
aaagtgaaga actattccgt taaccacctc aaaagatgat aaataaaaag ggtattttta  28980
gttgtttcaa cttttttttt ttttttgaga tggggtctta ctctgttgcc caggctggtg  29040
tgctgtggtg caatcatggt acaccgaagc ctcagtctcc ctgggctcag atgattctcc  29100
cacctcagcc tgggactaaa ggtgtacacc accatggcca gccaattttt ttgtattttt  29160
tgtagagatg gggttttgcc atattgccca gcctagcctc aaactcctgg gctgaaggaa  29220
tccacccatc tcagcctccc aaagtgctag gattacagac gtgaccaaca atatccggcc  29280
ttaacttttt tcttttgagt gtctttatag actcaaggac ttttatttaa ttcagggtgt  29340
tagtaccatt taaatgtttt ctttgatgct cagattatca cagctagtca tttggacctt  29400
tataccacct cctatgtcca tttgatatag gccattaatc tctataagcc ttcctccttc  29460
tcttggaatg aaaaggtatc ctaggctcac ctgtaccttc cctactccag acctggcatt  29520
aagtcttttt ccaaggagtt tggtaccttt tagtttatta tgatattaga gatgaaaatc  29580
tgtgttctag gaatgtttat tactgctaga gtgatgttgc ttttaggcca tttcagagaa  29640
aagacctaga aaacagattt ttacaaacat gaattcatac tgatattttt agtttttttac  29700
atgatttctt gattttacaa tattatctgc tttcttaact taaaattatg aaccttaaag  29760
tcattagcat aacttctttg cttatttcta caacataaag aaaatagtcc tggtgcggtg  29820
gctcacactg taatcccagc actttgggag attgaggcag gtggattgct tgagctcagg  29880
agttcaagac caacctgggc aacatgatga aaccttgtct ttacaaaaaa ttagctgggc  29940
atggtggcat gtgcttgtat tcccagctac tcaggaggct gaggtgggag gatcacctga  30000
gcccaggagg tcaaggctct agtgagccat gatcatgcca ccacactcca gcctgggtga  30060
caaagtgaga ccctgtttca gggggaaaaa aaagataaaa tagtttgagg aggctggatg  30120
tagtggctca tgcatgtcat cctggcactt tgggaggtca aggtgggagg atggcttgag  30180
cccaggagtt tgagaccagc ctgtgccaca tcatgagacc tggtctctat ttaaaaaaaa  30240
aaaaaaaaga aaatagtttg aggatatcaa taatgatatt actagaatca gtaaaactac  30300
caaaagaagt ttaaagtttc ttcctagtgt tttttgttc ttagaatact tcctaccaag  30360
aagtgcagta aaagtgcagt gtccaaatag cccttgtaac aaaacctttc tctttctcct  30420
gggtgccaat ttgacattta atcagttttg tttctagcag tgttcaattt attagattat  30480
aagtcttttt tttctttata ttattctaag atcaaaaata tataaagata tacacaggag  30540
tcctgctgct acctgttctt gctatgcttt tccccttttc ttccctttct ctgtgaagca  30600
gccattttta ttagtttctt gtttatcact catgcatgca tatgtttatt gaggatgttg  30660
acattcaagc aaatatatgg gttaacattc tttttgtcat ccctatacga aagatatacc  30720
cagtatactc tattgggtgg gttttttttcc ttaaaatatt cagtagatct ctccagttag  30780
cacatagtta tcttatagat agaacatata catataacct tttcttaaac tatgctatta  30840
```

-continued

```
aaataatagc tttcagtaac ttgataatta tttttggatt gaaaatacta ctgaaatcaa  30900
ctcaatcatg tgaaagctgc agaaagaaaa agacctagaa aaagggcatt ggattaggtc  30960
aactttgaat tttatttgga agataaatga gtccagaagt gagtgggcag agattattgg  31020
agttggtctt gaaatgaggc gttaggcaga ttgactgggc tggtgtgaaa ggtctgtcag  31080
aaaatcatga gattagattg aggtacctca aaaaatgaga gctggtatga tgagtgggta  31140
agaatcataa aagcgtagag tgttgatgat ttttatagtt tataaatggt tcttgtgtgt  31200
agagttttgt ttttatgcta gctatagtct gtaacataat tcactataat gggcatgcta  31260
aatatccatg acagttgacc cttgaacaac acagagggta ggggcgccta cccctgtgca  31320
gttgaaaatt cacatgtaac ttttgactcc ccaaaactta atatttagcc tatacttgac  31380
tagaagtctt actgatgaca taatgttcgt taatacatat tttatatatg tgtcagatag  31440
catatttgta taataaagta agctgcagga aaaatattaa aatcataaag aagagaaaat  31500
atacttacta ttcattaagt ggaagtggat cctcataaag gtcttcatcc tcactgcctt  31560
cactttgagt aggccgagga gtaggagaga gaggaaaggt cagacttgct gtctcatggg  31620
tggcagaggt agaagaaggt ccacatacaa gtggtccgac acagctcaaa ccggttttgt  31680
tcattggcca actgtagttt gattgaaagt aataataaat gaagtttctg cctcagttca  31740
gtattatcaa gtcatagata gcaagggctg gaagaaacct tagtagtaat ctctttgagt  31800
ctaattatca tgtagaatag gaaattgcgg tctagaaagg ttaagtgact tgtccaaatt  31860
acacaactag ttagagacat agccagctct taaatctgac ttccagattt tcactgtgtc  31920
ttcttttttc tgtaacgtgt tgcctttttt agccatgaaa aattagaagt tgaactcttg  31980
tcttttcagg caggtgtcaa ttttggggtt ttgttttgat ttttggtttt tgacataaag  32040
tactttagtt ctgtgatgta taaaccgtga gtttctgttt ttctcatata cctgaatact  32100
gtccatgtgg aagttacctt ttatctttac cagtattaac acataaatgg ttatacataa  32160
atacattgac caccttttat tactccagct atagtgggga aaactttctt ttcataacta  32220
gctaatgttt taaaaagtat tcttttagtt tgattgctgc atatttcaga tatttctttc  32280
cttaactaaa gtactcagat atttatccaa acattattgc tatgggattt cctgcagaaa  32340
gacttgaagg cgtatacagg aacaatattg atgatgtagt aaggtaagaa tgctttgatt  32400
ttctatttca aatattgatg tttatattca tgttgtgttt tcatttagaa aagatttcta  32460
agccacagaa aaagatactt tgtgatgtaa actattattg tagtgctcta taatcatttt  32520
ttggcttacc gtacctaatg gacttcaggg ggatacagtt catttgataa gaactgacct  32580
tatacattac ataatcaggt acttatgtga tatcatttcc tggactccat aaaatgctgg  32640
tcaccaggtt taatacctgg attccattac agtgtgattt ttgtcttatt tcatagttgg  32700
ggattaggct taaaatccta gagtggattt attcagttaa atttattcac actaagatgt  32760
agatgactaa tactgtatat ttttatgtag accaaatttt aaggtaccac tgtgcatatg  32820
tataccaact acctgaagaa gtatttggtt ggtacaagag atatagaaag gaatcgctgg  32880
gtgtaccaag gctaatcagt tttataattt tgcataattt tctaactgcg attatcattt  32940
agtttagaac aatttatttc tcaaggccca tgtaaatatt atttttaaaa tatacagtct  33000
taagaattca tggcatattt tatgaaagga ggaattcatg tctgatgtgc aaatagtctt  33060
aacatatttt ctaatttcag agcaaaaata tatatgtatg aataaattaa ctgtaaattg  33120
tcagtaggaa ccttaagaat tcgtggcgta ttttatgaaa ggaattcatg tctgatgtgc  33180
aaatagtctt aacatatttg ctaatttcag agcaaaaata tatgtgtatt aataaatcaa  33240
```

```
ctgtaaattg tcagtaagaa ccttaatggc tttaaaagtt aaaatttcag gtcaagcatt  33300
gtggtgtgct cctgtagtcc cagctacttg ggaggctgag gtgggaggat cacttggctt  33360
gaacccccag gtagagggta gaggccagtc tgggtaacac agcgagaacc catctcttaa  33420
aaaaaaagtt taagttgtgg attatttcct ttacactctt tcattagtat ctttcctgga  33480
gactttcaat ttaaatactt ggtgcttatg acaattagat gttaaaatgg atgggaaagt  33540
actttgtaac ttataaagca ttatgcagat gtagactcct tttataatag ttgtgtaagt  33600
atataagaca acctacattc ttcatgagct agccataagt tttagcaact tgctttgaac  33660
cacggtagat ttacaatttt ctgtagtatt gagttgtgtt catttagaat tttgtaatat  33720
ttatattgaa aatcaaattt ttgtacctac aaaaactaca aaaaatcccc ctagttttta  33780
tagtttctat taaaattata gctggtacat agggatgcca gaaggactgt ttaagaagct  33840
gaaaatagag aaatgaattt atcttctcat agttaggcag ggcacagtag aaggatgctt  33900
aacattgcaa gctgatggga acagcaggtt gatatagctt gtgataacac ttctaaagaa  33960
aaagcaatga gccatagaaa aaagaaaaag atacattttg aattaaggaa gatggtgaat  34020
ctgggaagtg agcagtacag tcaccagacg tgtatcctct cctatggtac agaagtgttt  34080
attgggtctc tttatggcct gcatgatata tcccacaaga tgacctactt cacattattt  34140
taattctgta ttcaactaag cactaattca acccagccag attagtactc ataccaaaaa  34200
agagtgaata ctctgaatag agggcaggtt ttctgattat ggtgagaata tctttgtggt  34260
aaattaatct ggtgtgctag tttttacgtt ggtctcttct cagtgtcgtt agtcactgag  34320
gctgattgat catcttttag gttactgata aagttcctgt acagctgatt ttcagacctt  34380
agattgcaat aacttcacca agaaaatact tcattgggaa gcattttggt ccttccattt  34440
gattcataac tcttaccttt atgcctctga aggaaaagat ttatacattc agcttgtaat  34500
tagtaatcaa gactgaggtt tagtctatct agcttcacaa tctatctagt ttgttttgtc  34560
tagccatatg atttcttcaa atatgccatt tcttaaaaaa aaatgtttta tgtatcccga  34620
ttaatattta gccagtggtt cttttagccg atggatcttg tcacctctta tgatactatt  34680
aatagcatgt caacatgaag aattatctgc tgaatataat agctatgctg tccttgtttc  34740
cttttgtctc attctttttt gattggggga taattggcca ataaagcttt gatagcctct  34800
attgcccagg cccctcctct tcttttatga gagaaaggat gaacagtgac cagaaataaa  34860
ggtattgttt ttttctatca actaaaatgg aaataaataa ttcctaagta atttgcctgt  34920
taggattaaa gtctccaaga gaatggctgt gcctagtacc taagtgatta atttccttga  34980
ttggttcaca ttatattgag gatattagta atcagtagtg attccttttt tggttcaaag  35040
atgatagtgt cacagtgaaa aatgttttta aaatttttgt atacttaatt tttctgttaa  35100
cgaaagtatt ttcagttgga tttttgtttg ccctctctat tagaatgccc aaagaatatt  35160
taaaatttc  cttttctctt atactgcata tttttcctgt gatttttccc caaacggaaa  35220
atactctgca gagattagac tttgttattg ttgtactaca tcattgcttt gactaaaata  35280
aactcagatt gcaaatacct tcaagcttac attgctcagt attttttttt tttttttttt  35340
ttgagacgga gtctcactct tgtcgcccag gctggagtgc agtggtgcca tctcagctca  35400
ctgcaacctc tgcctcctgg gttcaagcga ttctcctgcc tcagcctgcg gagcagctgg  35460
gattatagat gcccgccccc acgcccagct gatttttgta tttgtagtag agatggggtt  35520
ttaccttgtt ggccagtctg gtctcaaact cctgacctcg ggtgatccat ctgtctcggc  35580
```

-continued

```
ctctggaatt acaggtgtga gccgccacgc ctggctaaat tgatcagtat tatttaactt  35640
tgagggatat gatttgttat ggaatgcgaa gttttatact tgaggtactc agagtccttt  35700
tgagacaaat atttaacttc tccttttgag gttaccgcct acgattggga attaatgtaa  35760
aaaataagcc aaaagaaagt gagggaaaag tgaaccaagc tgtaattttt ttactctttt  35820
ttattgttgt tgttattgtt gctgtttttt actatcttga ttgcaacagt ttggcttata  35880
tatatagcat ttggaattga cagtaagaaa gccacatctc atagaagcta actattccca  35940
aattgttttt ttcttctttt cctcttacta ctgctgtttt cctcctttct tgctgctaag  36000
ctcttgtcct gacatgctgg taatatgaaa cagtgtttta ttcagataat tgattattct  36060
gtaatatgta tgttaatctt ttttattaca ctttaagtaa tagggtacat atgcacaact  36120
tacagattcg ttacatatgt atacatgtgc cgtgttggtt tgctgcaccc attaactcgt  36180
catttacatt aggtatttct cctaatgtta tccctctccc aaccccccac cccaggacag  36240
gccccggtgt gtgatgttcc ccgccctgtg tccaagtgtt ctcgttgttc agttgccacc  36300
tgtgagtgag aacatgcggt gtttggtttt ctgtccttgc gatagtttgc tcagaatgat  36360
ggtttccagc ttcatctatg tccctacaaa ggacgtgaag ctcatccttt tttatggctg  36420
catactactc cgtggtgtat atgtgccaca ttttcttaat ccagtcagtc attgatggac  36480
atttgggttg gttctaattc tttgctattg tgaatagtgc tgcagtaaac atacgtatgc  36540
atgtgtcttt atagtagcat gatttataat cctttggata tatacccagt aatggaattg  36600
ctgggtcaaa tggtatttct agttctagat ccctgaggaa ttgccacact gtcttccaca  36660
atggttgaac tagtttacag tcccaccaac agtgtaaaaa tgttcctgtt cctccacatc  36720
ctctccagca cctgttgttt cctgactttt taatgatcgc cattctaact ggtgtgagat  36780
ggtatctcat tgtggttttg atttgcattt ctctgatggc cagtgatgat gagcattttt  36840
tcatgtgtct gttggctgca taaatgtcta taaatgtctt cttttggaaa gtgtctgttc  36900
atatcctttg cccacttttt gatggggttg tttgattttt ttcctgtaaa tttgtttaag  36960
ttctttgtag attctggata ttagccattt gtcagatggg tagattgcag aaattttctt  37020
ccattctata ggttgcctgt ccactctgat ggtagtttct tttgctgtgc agaagctctt  37080
tagtttaatt agatcccatt tgactatttt ggcttttgtt gccattgctt ttggtgtttt  37140
agtcatgaag tccttgccca tgcctatgtc ctgaatggta ttgcctaggt ttgcttctag  37200
ggtttttatg gttttaggtc tacatttaag tctttaacat ttaagtcttt aatccatctt  37260
gaattaattt ttgtataagg tgtaaggaaa tgatccaatt tcagctttct acatatgact  37320
agccagtttt cccagcacca tttattaact agggaaccct ttccccattt cctgtttttg  37380
tcaggtttgt caaagatcag atggttgtag atgtgtcatg ttatttctga gggctctgtt  37440
ctgttccatt ggtctatatc tctgttttgg taccagtacc atgctgtttt ggttactgta  37500
gccttgtagt atagtttgaa gtcaggtagt gtgatgcctc cagctttttt ctttctgctt  37560
aggattgtct tggcagtgcg ggctcttttt tggctccata tgaactttaa agtagttttt  37620
tccaattctg tgaagaaatt tattggtagc ttgatgggga tggcattgtt tctataaatt  37680
accttgggca gtgtggccat tttcacgata ttgattcttc ctacccatga gcatggaatg  37740
ttcttccatt tgtttgtgtc atcttttatt tcgttgagca gtggtttgta gttcttgaac  37800
aggtccttca catcccttgt aagttggatt cctaggtatt ttattctctt tgtagcagtt  37860
gtgagtggga gttcactcat gatttggctc tctgtctgtc tgttattggt gtataagaat  37920
gcttgtgatt tttgcacatt gattttgtat cctgagactt tgctgaagtt gcttatcagc  37980
```

```
tgaaggagat tttgggctga gacagtgggg ctttctaaat atacaatcat gtcatctgca  38040
aacagggaca atttgacttc ctcttttcct aattgaatac cctttatttc tttctcttgc  38100
ctgattgccc tggccagaac ttccaacact gtgttgaata ggagtggtga gagagggcgt  38160
ccctgtcttg tgccagtttt caaagggaat gcttccagtt tttgcccatt cagtatgata  38220
ctggctgtgg gtttgtcata aatagctctt attattttga gatacgttcc atcaatacct  38280
aatttattga gagtttttag catgaagggc tgttgaattt tgtcaaaggc cttttctgca  38340
tctattgaga taatcatgtg gtttttttgtc tttggttctc tttatgtgat ggattatgtt  38400
tattgatttg cgtatgttga accagccttg catcacaggg atgaagccaa cttgatcttg  38460
gtggataagc tttttgatgt gctgctggat tcggtttgcc aatattttat tgaggatttt  38520
tgcattgatg ttcatcaggg gtgttggtct aaaattctct ttttttgttg tgtctctgcc  38580
aggctttggt atcgggatgg tgctggcctc ctaaaatgag ttagggagga ttccctcttt  38640
ttctatgaat tggaatagtt tcagaaggaa tggtaccagc tcgtcttttt acctctggta  38700
gaattcggct gtgaatctgt ctggtcctgg acttttttcg gttggtaggc tattaattat  38760
tgcctcaatt tcagagcctg ttactggtct attcagggat tcaacttctt cctggtttag  38820
tcttgggagg gtgtatatgt ccaggaattt atccatttct tctagatttt ctagtttatt  38880
tgcatagagg tgtttatagt attctctgat ggtagtttgt atttctgtgg gatcagtggt  38940
gatatcccct ttatcatttt ttattgcatc tatttgattc ttctctcttt tcttccttat  39000
tagtcttgct agcagtctat caattttgtt ttttaaaaaa accagctcct ggattcattg  39060
attttttttt tgaagggttt tttgtgtcct atctccttca attctgctct gatcttagtt  39120
atttcttgcc ttctgctagc ttttgaattt gtttgctctt gcatctctag ttgttttaat  39180
tgtgatatta gggtgttgat tttagatctt tcctgctttc tcttgtgggc atttagtgct  39240
ataaatttcc ctgtatacac tgctttaaat gtgtcccaga gattctggta cgttgtgtct  39300
ttgttctcat tggtttcaaa gaacatcttt atttctgcct tcattttgtt atttacccag  39360
tagtcattca ggagcaggtt gatcagtttc catgtagttg tgcagttttg agtgagtttc  39420
ttaatcctga gttctaattt gattttactg tggtctgaga gacagtttgt tgtgattttt  39480
attcttttac atttgctgag gagtgagtgc tttacttcca actatgtggt caattttgga  39540
ataagtgtga tgtggtgctg ataagaatgt atattctgtt gatttgggat ggagagttct  39600
gtagatgtct attaggtctg cttggtgcag agctgagttc aaatcctgga tatccttgtt  39660
aaccttctgt ctcgttgatc tgtctcatat tgacagtggg gtgttaaaat ctcccgatat  39720
taactgtgtg ggagtctaag tctctttgta ggtcactcag gacttgcttt atgaatctag  39780
gtgctcctgt attgggtgta tatatattta ggatagttag ctcttcttgt tgaattgatc  39840
cctttaccat tatgtaatgc ccttctttgt ctcttttgat ctttgttggt ttacagtttg  39900
ttttattaga gactaggatt gcaacccctg ctttttcttg ctttccattt gcttggtaga  39960
tcttcctcca tccctttatt ttgagcctgt gtgtgtgtct gcatgtgaga tacatctcct  40020
gaatacagca cactgatggg tcttgactct ttatccaatt tgccagtctt tgtcttttaa  40080
ttggggcatt taccccattt acatttaagg ttaatattgt tatgtgtgaa tttgatcctg  40140
tcattgtgat gttagctggt tattttgccc attagttgat gtagtttctt cctagcatca  40200
atggtcttta caatttggca tgtttttgca gtggctgata ccagttgttc ctttccatgt  40260
ttagtgcttc cttcaggagc tcttgtaagg caggcctggt agtgacaaaa tctctcagca  40320
```

```
tttgcttgtc tgtaaaggtt tttatttctc cttcccttat gaagcttagt ttggctggat  40380
atgaaattct gggttgaaaa ttctttttctt taagaatgta gactattggc ccccactctc  40440
ttctggcttg tagagtttca gcggagagat ctgctgttag tctgatgggc ttccctttgt  40500
gggtaacccg acctttctct ctggctgccc tttacatttt ttcctgcatt tccaccttgg  40560
tgaatctaac aattatgtgt cttggggttg ctcttctcta ggagtatctt tgtggtggtc  40620
tctgtattcc ctgaatttga atgttggcgt gccttgctat gttggggaag ttctcctgga  40680
taatatcctg aagagtgttt tccagcttgg ttccattctc cccgtcactg tcaagtacac  40740
caatcaaacg tagatttggt cttttcacat agtcccatat ttcttggagg ctttgttcat  40800
ttctttttac tgttttttct ctaaacttct cttcttgctt catttcattc atttgatctg  40860
caattactga taccctttct tccacttgat cgaatcggct gctgaagctt gtgcatgcgt  40920
catgtagttc tcgagccatg attttcagct ccatcaggtc atttatggtc ttctgtacac  40980
tgtttattct agttagccat ttgtctaatc ttttttcaag atttttagct tccttgcgat  41040
gggtttgaac atcctccttt agctcggaga agtttgttac tactgacctt ctgaagccta  41100
cttctgtcaa ctcgtcaaag tcattcttca tccagctttg ttccattgct ggtgaggagc  41160
tgtgatcctt tggaggagaa gaggcactct gggttttaga attttcagct tttctgctct  41220
gttttctccc catctttgtg gttttatcta cctttggtct ttgattatgg tgacctacag  41280
atggggtttt ggtgtggatg tcctttttgt taatgttgat gctattcctt tctgtttgtt  41340
agttttcctt ctaacagtca ggtccctcag ctgtaggtct gttggagttt gctggaggtc  41400
cactccagac actgtctgga tatcaccagt ggaggctgca gaacagcaaa tattgcagaa  41460
cagcaaatat tgctgccgga gccttcctct ggaagcttcg tcttgggggc acccggctgt  41520
atgaggtgtc agtcggcccc tactgggagg tgtctcccag ttaggctaca agggggtcag  41580
ggacccactt gaggaggcag tctgtccgtt ctcagagctc aaacactgtg ctggtagaac  41640
tactgctctc ttcagagctg tcagagaggg atgtttaagt ctgaggaagt ttctgctgcc  41700
ttttgttcag ctatgccctg cctccagagg tggagtctac agaggcaggc aggcctcctt  41760
gagctgtggt gggctccacc cagttggagc ttcccaacca ctttacctac tcaagcctca  41820
gcaatgatgg acgcccctcc cccagccagg ctgctgcctt gaagttcaat ttggaactgc  41880
tacgctagca gtgagcaagg ctctgtgggc gtaggacctg ctgagccagg cacgggatat  41940
aatctcctgt tgtgccattt gctaagaccg ttggaaaagc gcagtatttg ggtggcagtg  42000
tcccaatttt cccggtatag tgtgtcacag cttcccttgg cttggaaagg gacatccccc  42060
gaccccttgt gcttcctggg tgaggcaatg ccccgccctg cttcagctca ccctccgtgg  42120
gctgcaccca ctttccaacc agtcccagtg agaagaacca ggtacctcag ttggaaatgc  42180
agaaatcacc tgtcttccgc gtggatcatg ctgggagctg cagacaggag ctgttcctat  42240
ttgaccatct tggaatgcca cctttttttt tttttttttt tttttaaggc agtttcttgc  42300
tctgtcaccc aggctggggt gcagaggcat gatcacggct cactgcaacc tctgccttct  42360
gggctcaagt gatcctccca cctcagcctc ccaagttgct gggaccacag ccacgcatca  42420
ccaggcctgg ctaattttg tgttttttgt agagataggg tttcgctgtg tttcccaggc  42480
tggtctcaaa ctcctgcgct caagcgatcc gcctgcctca gcctcccaaa gtgctgggat  42540
tacaggcatg agccactgca cccggccaat atgtatgtta atctcatccc tcaagctgat  42600
actgaagttt ttcaatttat gttatttggt gtaaatctag gcagtcttta acaaaattgg  42660
tgcttcatgt gtttaagagg cataacttaa gaattgtttg tttcttataa atcaggagaa  42720
```

```
tggaggttta atagaggtga actgtctttc tcactgcaga acctttaata tgccactatg  42780
cattgtaaat ctcccaagag tgagattcta gtatgatgct tttcttttcc ttttctgttc  42840
tttccctttc cctctacctc ctttttcttt tctttgttgg tggcatgagt cctatattat  42900
aaggaaatgc ttttagagta cagtcttctg atatatagtg atttttgaaa aagatttatt  42960
tattgtcttg ttcactgtga gctttttccc ccatgtataa gcagctgtgt aatagattca  43020
agagcacccc ctcgcccctt ttttttgag acagagtctc gctcggtcac tcaggctgga  43080
gtacggtggt gctgtgatca tggttcacct cgacttctgg gctccagcga tcctcccacc  43140
tcatcctctc aagtagctgg gaccacaggc gtgtgtcacc gtacatggct aatttttcta  43200
tttttagtag aggcagagtt tcgccatgtt ttccaggctg gtctcgaact cctgaactca  43260
agcagtccac ctgtctcagc ctcccaaagt gctgggatta caggcgtgag cctccactcc  43320
cagtctcaaa tattcttttg aaatatttga aatatgttga tctctcagtc tttcaacctt  43380
agttgtatgt tgattttcaa taaaaaggaa gtatttgttg ccctaacatc agtattggct  43440
attcagttta aaaaaggagt taaagagatg ttatttatag gcaggcttca aaagaggaaa  43500
gaatgatcag tttcattctc tgtttctagc atattctgac tccttctctc atattacctc  43560
gtttttccca catttttctt ttaataaagt gaaattcaca taacagctaa ccattttaac  43620
cacggaaagt gtacattccg tggcatttat taccttcaca gtgttacctc tacctttatc  43680
aagtttcaaa acattttatc accccaaaag aaagccctgt tcttattggg tgcctcttgc  43740
ttttttttt ttttttttt ttaaatcttg agacggggtc ttggtttgtt tcccaggttg  43800
tagtgcaatg gggcgatctc atctcattgc aacctctgcc tcccgagttc aagcaattct  43860
cctgcctcag cctcccgtag ctgggactac aggcacgcgc cacatgcctg gctaattttt  43920
gtatttttag tagaaacgtg gtttcaccat gttggccagg ctagccttga actcctgacc  43980
ttaggtaatc tgcctgcctt ggcctcccaa agtgctggga ttataggcgt gagccaccgt  44040
tctggccacc tcctacttct ttcattagtc ttaattcctt agtggatttg acagtgttta  44100
tattatctac accaatgcat ttttttgtat gttaataata ggagatattt attgggcatt  44160
tatttacata cttatttgca tgtgtaactg ttgtatagcc agtttatgta tataatctta  44220
ctaaatctct acagtaaatc tatccccatt tcatagatgg tttaaaagaa gttaacttcc  44280
ccaagcatta cttttagtaa gtagtgagac tgaaggttga gttctggtct gtcagattcc  44340
gaagttgttt ccttaggaac catattatct tgtgtacaac tcttgggcta atcttgttaa  44400
tattctttat ttgacctcac actgttgatt cataccatgt ttaaaattga aatacattac  44460
ctatatttaa aaattgagac ctcacataaa aagctatatt tctagctgct tttgaaattt  44520
cgaaggatct tccaacactt ggctgacatt cctgcgtgac aaaaatcagc tggagctgtg  44580
taatgtccga cctgtctctg tcaatgaaca gattattcat tgtcatttct catctgtttt  44640
tgagattgta actttgattc tgtataactc atagaattag tagttagacc tatatatgtt  44700
agttattaca ttatttgtat atgtacagac tgctttagac aatattgtag tgttatatgt  44760
taattttatc aattaaaatg tgctatagga tcattgtaga gatcttgtct ctaattaaca  44820
ggattcataa agagaaaaca aaggagagaa acatccagat tgaaaagacc tacatagtgc  44880
caagcacaat aaaagaaacc ctatactagg caaattatta tgaaatttgt tttaggacac  44940
cagaaataaa gataatatct aaaaactttt tagaatcgcc taggagggat taggaatatg  45000
aatagcatct aacttgttgg cagtagaatt gaaggtagaa ggtggtaaaa catcaccttg  45060
```

```
aaagttctgc attcagccta gaattctgta tccagttaaa ccatcaatca agtgtgaaag  45120
tagggggaaa aactcaagga ctaaaaaaat gtgctcatga agaacatttt ttttggacat  45180
tacccagaag atgtggttca acaaaacaag ggaataaacc aagaaaggaa ataaaagagc  45240
ttcagtaaac agagaatccc actcagaagc aacaaagaag aaagtcccag gatgacagct  45300
gtgacacaag ctgaaaagtt accagttttg cttggagcag gagattagaa cttccgggaa  45360
aataatcaaa ttgatagatg gatgttgaaa tatttggaga aaaatgtaat ggattcttgc  45420
aaaactgagc aaattagaaa aaggaaacaa ttattagcat tggtggtttg agttaaccca  45480
aaattgtgat gttgctattt taggggaatt aagataagtg aaacacgtat ggaatactgc  45540
tagttttgta agtctccttt accatggcag gacatctgta gttaataaat ctgtaagaag  45600
cagtattaag aataatattt taaaatacct aattaaatag gaggaaaaag aatccgagta  45660
gttgagggtg attgcatctg gggagaagca ggaataaagg tttgaagata aatagggcca  45720
gagatgagta attttgttac tgtgataata tattttatat atatgtgtat gtgtgtgcgt  45780
gtgtatatat atatatgaga tatatctcat atatatgaga tatatatgat atatatatga  45840
tatatatgat atatatatat aaaacataca gttcagtagc attaacatct agcattcagt  45900
acatttacat tgttgtgcaa ttgtcaccac tgtccatctc tagaactttt tcattatccc  45960
acactgacat accacaccca ttaaataata actcctcatt gctcctcctg ttagtaccaa  46020
ccattgttct actttcatct ctatgtattt gactattcta ggtacctcgt ataagcggaa  46080
tcacgtgata tctttttgta actggcttat ttcactaact atcttcgagg ttcatccatg  46140
ttgtagcagt tgttagcatt tccttccttt taaaaggccg aataatattc cattgttatg  46200
tatataccat attttgttta tccatttatt catcaataga cacttttggc tgttgtgaat  46260
aatgctgcta tgaatatggg tatgtaatac ctgtttgagt atctgctttc atttcttttg  46320
gatatgtacc caaaagtgag attgctggat tgaatggtaa ttctatattt aaatttttga  46380
gaaaccacca tactgtttga tatactggct gcccaatttt acattaccac cagcaataca  46440
ctagggttcc gaatttgcca catcctcacc atcgtgttgt tttgtttatg ttttttttta  46500
ataatagcca tcctaatggg tgtgaagtct cattgtggtt ttaatttgca ttttcctaat  46560
gatcagcgat attgaacatt tgcacatgct tatttggtca tttgtatatc agctttggag  46620
caatgatgtc tcttgaagcc ttttgcccat ttatgaattg agtagtttgg gatttttaaa  46680
ttgtgtttta gaagttcttt gtatactctg gctgggcacg gtggctcgtg cctttgggag  46740
gccgaggcag gtggatcacg aggttaggag ttcaagacca gactggctgg tatagtgaaa  46800
ccccatctct actaaaaata caaaaattag ctggtgtggt cgggcgtgat ggtgcacacc  46860
tgtagtccca gctgttgggg aggctgaggc aggagacttg cttgaacccg gaaggtgggg  46920
gggttgcagt gagctgagat tgtgccactg cactcagcct gggtgacaga gcgagactct  46980
gtctcaaaaa aaaagaaaaa gaagttcttt gtattctctg aatattaatc ccttattgga  47040
tatgttattt gcaaatattt tctcccataa agaatgggtt actttttcac tctgttgatt  47100
gtttcctttg ctgtgcagga gctatttagc ttgaaaaaat ccaacttgtc tgttttcttt  47160
tgttgcctgt acctttggtg tcacattcaa gaaataattg ccaaattcat accatgaaac  47220
tttcccccat gttttctcct gaaggttttt atagttttag ctctcacatt taggtgtttg  47280
atccattttg agttaaattt tgtatataat gttatgtaag agtccagctt cacacttttg  47340
gatgtgaata tctagttttc ccagcattat ttgttgaaaa gagtgtcttt ttccccattg  47400
aatagtcttg gcactcttgt tgaaaattat ttgacaatag atgcaagggt ttatttttgg  47460
```

gctctctcga ctattctgtt agactatatg tttgtttttt tatgtcagga ccaccctaat 47520
tttagtactg tagctttata gtaaaatttg aaaccaggaa gtatatgtct tgtgtattta 47580
tttacttatt ttttgaaata gcatctggct ctgttgccca ggctggagtg cagtggcaca 47640
atcttagctc actgcaacct ccacatctga ggttcaagca atcctcccac ctcagcctcc 47700
tgagtagctg ggattgtaga cacataccac catgctcagc tagtttttgt atttcttgta 47760
gagacagggt tttgccatat tgcccaggtg ggtctcgaac tcctgagccc aagcagtctg 47820
ccctcctcag tgtcccaaag tgttgcgatt acaggtatga gccaccgtgc atggccccaa 47880
cttcttatat ttcaagatgg ttttggccct tcagggccct ttgtgagttt taggatggat 47940
ttttttttta acttttaagt ttaggggtgc atgtgcaggt ttattacata ggtaaatttg 48000
tgtcaaggtg ttctgttgta tagattattt catcacccag gtattaagcc tagtacccat 48060
tagttatttt tcctgagctc gcctcctccc acctggattt ttttttttat ttctaccaga 48120
aacattgttg ggattttggt agggattgta ttagtctgta gattgcattg aatagtactg 48180
acatcttaac aatattaagt ctttaaagcc atgaacacca gatgtctttc catttattta 48240
cgtattcttt cttttctttc agcaatgttt tgtaattttc agtgtacaag tattttacct 48300
ccttggttaa gttaattcct aagtatttta ttcattctga tgatcttata aatctgtttt 48360
cttaatttcc tttcctaatt gttcattctt agggtataga aacacaactg attcttcgca 48420
cattaaattt gtgccctgct tcttcgcggg tttgtttatt cttttttgt gtttgaaatc 48480 cttgaggttt tctgcatata agattatatc atctgcaaat gagataattt tacttgttcc 48540
tttccaattt gagatgattt ttattcattt tcttaatgct ctctcataca ttcaatacta 48600
tgttgaatgg aagtggtgaa agcaggcatc ctgtcttgtt tctgacctta taggaaaagc 48660
tttcaattct ttgccattga ctatcatgtt agctatggga tttttttttt ccccccagat 48720
agagtctcgc tgtgtcgccc aggctggagt gcagtggtgc gatctcggtt cactgcaccc 48780
tcctcctccc gccaggttca agtgattctc ctgcttcagc ctcccaagta gctgggatta 48840
caggtgtcca ccactatgcc cagctaattt tcgtattttt agtagaaaca tggtttcacc 48900
atgttggcca agctggtctc gaactcttgg cctcaagtga ttcacctgcc tcggcctccc 48960
atagtgctgg gattatagtc agccaccatg cctggccact gtgggatttt tatatatggc 49020
cttcattatg ttgtggtaat ttctttttat tcttagttta ttgagtgttt ttatcataaa 49080
atcttgttga atttttcaa atatttttc tgtgctagtt gagatgacca tgtgatttgt 49140
tttcttcttt ctattaacat gatatattgt ttttcatata ttgagccatt tttgcatccc 49200
aggaataaat tttacttggt cttcgtgtat aatccattta ataagctgtg gaattcagtt 49260
tgttggttct gtgttgagga ctttatatca atgttcctaa gggctactgg tctatagttt 49320
tcttttgtag tttctttgac tttgctatca gggcaatgct ggcctcattg aatgtgttag 49380
gaagtgtttc ctcatccatt tttggcaaaa ctttgggaaa aaacgatgtt ctttaaatgt 49440
ttgatagaat tcacagataa aaaaatcaca tctagggctt ttgtctggaa ttttttttatt 49500 gttattattg attcagtctt gttactagtt ataggtctat tcagattttc tttttgtgtg 49560
tgtgattcag tattagtaca ttttgtactt ctcgttattt ctccatttaa tctatattat 49620
ctaatttgtt ggcatacaat tgttcatagt actgtcttct cttttttta aacttctgtg 49680 cagttgatac taatgtccct acttttattt cagattttag taatttgaat cttctttatc 49740
ttaatacagg taaagctggg tcaattgtta aaattttttc aaagaaccag tttttggttt 49800
cattgatttt tctctgttat ttttctatta tttatatcct ctctaagctt tgttatttcc 49860
ttcatcctgc tagctttggg tttattagtt tgttcttttt ctagttcctt aagatttgaa 49920
gttggattat tgatttgaga tcgttttcaa ttaaatgtgt acaactacaa atttccctct 49980
taggactgct tttgctgttc tgtaattttt ggcatgttgt gtttttttgt tttaatttat 50040
ttctaagtat tttctaagtt cccttgtgat ttcttctgcg tttaaccgtg tatttttttaa 50100 tttccacagt tggtgaattt tctacttttt cttcagttat tgattttatt gattttcagt 50160
ggcatcctgt tgtgatagaa gatactttat ttggttccct gttttttttt taaaacagag 50220
tgttgctctg tcacccaggc tggagtgcag tggtgcgatc ttggctcact gcaacatcca 50280
cctcctgggt tcgagcaatt ctcctggtct cagcctcccc agtaggtagg attacaggca 50340
catgccacca tgcccagcta atttttgtat ttttagtaga gacagggttt cgccatgttg 50400
gccaggatga tctcgaactc ctgacttcaa gtgatccacc cgccttggcc tcccgaagtg 50460
ctaggattat aggcgttagc caccttgtct ggcccagatc ctctattttc ttgcctatat 50520
tctgactggg tgtttttgtc cattattgag agtagggtat cgaagtgtcc agctgttatt 50580
tcagaactgt ctgtttacct tcaattctgt caatttttttg cttcatataa ttgggtggtc 50640
tcttattagg catgtaaatg tttttgatta ttatatcttc ttgctatatt gacacttatt 50700
gatgtgtaat atcttttttg tctcaacctt gttttgattt agtttgtcta atattaatgt 50760
agctacctgc actctcattt ggttattact tgtatagaat gtctttttac atcccttatt 50820
tgtgtctttg gatctgaaat gagtctcttg tagacagcat atacaatctc ttgtagattg 50880
tgtttttctt atacattctg tcaaactctg ccttttgatt gaagagtttt atcatttaca 50940
attaaagtaa ttattgataa ggatttaact gctgccattt tgctgtttat tttctatatg 51000
ccttacagct tttttgtccc tcatttcctg ccttactggc acttgtgttt agttgatatt 51060
ttgtggtgaa gtgttttaat ttccttgtta tttccttttg tttatattct gctatttttct 51120 gtgtgtgtgt gtgtgtggtt gccattgggg gtcacattta atgccctaaa gttataacac 51180
tgcaatttca atttatacca atttactttc aatagcatac aaaaattcag ctcataagat 51240
tcagtccctg ctcccttcca gttattgatg tcataaaatt acatttttat gtattgtgtg 51300
tctaaaagcg tagactaata attgtttttt aatgcagtag tgtcttaatt tgtggaaaac 51360
aaaaagtgga gttgtaaacc aatgttacaa taatgctagc tttggtaatt gctcatgtat 51420
ttatcatttc tcagatcttt atttcttaat acagcttcaa gttactgtct agtctccttt 51480
tatttcagcc tgaaagactc acttcagcgt ttcttgcagg acaggtctgg tgataatgaa 51540
ctctctcaga ttttgttaat ctggaaatgt cttaatgtct tcatttttaa ggacattttt 51600
gctggatata gtattctcag ttgacaggta tttgtgttta tttgtttgtt tcctttcagg 51660
attttaaata tatcatccca ctgccttctg tccttcaaga gttctgatga gaaatctgct 51720
gatattgagg atccctttgt atgttacaag ttgcttctct cattccatgt tcaggattct 51780 ctttttttcat agtttgatta taatctatct cagtttttcc tacttggatc tctgagtttt 51840
tcctacttgg agttaattga gcttcttgaa tatttatatt catgtctcat caaatttggg 51900
aagtttttga ttaatatttc ttcacataat cttttttgcc ccttttctct cttttttattc 51960 tgggattccc agagtgtgta tgtgttggtc cacttgatga tggtgttcca caggtgtctt 52020
aggctcttgt cttcaatttt ccttcagttt tttttttctg ttcctcagac acgtggtatt 52080
ttcagctgtt ctgccttcca agtttactga ttcttctgcc tgcccaaatt ggcttttgaa 52140
ttcctctagt aaatttttat ttcagttttt gtacttttca gctccagcat ttattttttg 52200

```
atttttttat gttttctctt tattgatatt tcaattttgt tttttgacat tatccatatc  52260
ttcctttagc tttttgagca cctttcaaca tttgttttaa agtctatgtc tagtaagtgt  52320
ctgccatctg atcttctcag gcacagtttc tgttaattta tttttttcct tttggcctat  52380
acttaatgtt ttgcttgggg tagttttttt ttttggtatg ctttgtgatt tttgttgttg  52440
ttgtcaaaaa ctggaatttg aatcttaaag agtggtaact ttggaaatta gatttttctc  52500
ttttctctaa gatgtgctat tttgtttggt ttttttattt gttgtagagt atttctatgc  52560
tgggtgtaat cttaagatct tctcggcctg tgtttttccc tgggcatgtg tagtgacttt  52620
ctaaattgcc ctatgtatgc agttcttttg cagtagtatc ctccttaaat gtttggctcc  52680
taaaaggcaa aataaataaa taaataaata aaaattaaaa attaaaaata aatcaaaggg  52740
gtgaaatagc tctggatctt taaatccctg gagcaatttt ttcagccaat ggcagttaaa  52800
taatgatagt ctgcctctgt gtcacatttt gatcagaagc agcaattagc aatcagaaca  52860
cagattcctg atatttggag ggcaaggtct ttgttgccaa ccttgactct tacaaactgt  52920
gtgcagggtg ctctgggaac atgtgcatgg ttgcctgctt tgagagtggg tgatgggtag  52980
ccgcgacggc acaaagagct gaaattgact caaactaact gatttaccat tcaagtcttt  53040
ccttagaaac tgaaaacctg aatagactcc agagttccag aatcacagat tctgcttaca  53100
gtcgtctagg tggggagatg ggttcctggt acttctgatt ctgccatctt tctttgacta  53160
attttttttt tttgttcttg agatggagtc ttactctgtt gcccgcccag gctggagtac  53220
agtagcatga cctcggctca ctgcaacctc tgcctcccgg gttcaggcaa ttctcctgcc  53280
tcagcttccc aagtagctgg aattacaggc gtgcaccacc atgcctggct aatttttttgt  53340
atttttagta gagacagggt ttcaccatgt tggccaggct agtctcgaac tcctgacctc  53400
aggtgatcaa cccgcctcag cctcccaaag tgctaggatt acaggtgtga gccactgcac  53460
ccagctctta gacaaatttt ttattccaaa cttttttat tttatcattt gaaaggtata  53520
tgtttattat tttgtcaaaa ataattttaa aacgtattct tgaagcttat ttagatctgt  53580
ttcataggaa ctgtgaagaa agtaaagaat ttaaaaaatg aagacagatt ttctcaccct  53640
gcttatgggt gcttctcgtg ctagcctttt gcaagtgtcg ggaagtgtaa cctgcaggag  53700
gcatcagggc tttgggcctg catggtctga gtgctgccct gtgagtttca gaaggcgcag  53760
caacctgtat acctgaaagc catctctgct ggggcaggta cctagtgtcc ccacctacct  53820
gggtcgtagt caggccctgg gcaagcctgc tatgcttttc cttccctaat ccctcagggg  53880
tgggatagag agcacagtgg cctcccaggg aggtagaagc tgctccagac taacaatcag  53940
agctgccagt tcttaatccc caagaccgcc agacttcaca aagacatacc gaggtctgtg  54000
ctgtcagtgc cccactacta cactccctta agtagcccca cattcttgtg cttgtttctt  54060
ttttctgctc tctttccttg cccaggtaag aggtctgccc ataagggata ttttgcagca  54120
tgtgaagctt tttaaaaagt taggcttatt gaagtataat ttacacacaa agtacaaaaa  54180
aaaaaagact gtgttctcaa atctgtgagt cattaatggg tttagatgtt tatatattga  54240
aattattgga agtaaggtat gtttatatta gaaagatttg tagtctagat tatccaagtt  54300
ttgggagtat tacctctctg cttttgttta tctacttttt tagtctctac tttccaagta  54360
tctataggca aattttccca tttccctttg gaaagtgctg ttttcttgct ttttttccgc  54420
ctttccattg tgtcagactt ataaggcaat cagccaactg tgggcatgaa atccttggga  54480
ggaaagagaa ggaagtggga ggggcagcca tggtgaatgt ttccctaagt tatagtcaag  54540
```

```
ttctttgaga gaacataacc tcatcccctt tttaaactgt tgtaatactt tcttttaaat  54600
agattgttta ttctcctgca agtctcacag ttgttcacag tggtaggtaa gaaatcataa  54660
agttcaaata ttaaagggag ctcacaaaag agcatggttt caccagccct cactaaaaac  54720
aaaattatgg gaaaatgctg taaaagaaac cagaattctt ggttgcaaat gatagaaagt  54780
gactctgatt tacctaatca gaaaggaatt tttaaaaaag tattaggtag gtcatagttt  54840
gacaacaaga cttggaagat aggtggaagc taagggaagc aagacatggc cccaaggttt  54900
caacaggagc aatctgctta ggactttgct gcttggacac ttggtgtaat agctgctgcc  54960
actatgcctc gaaactggtg actctgctca ttaactcacc tcctctggtg atctctagga  55020
ataatctctg actctcctgt accttgtcct cactaggatt cggtatccac ggcaaaaaga  55080
tctattaata gttggtatca ggcctgtaca tgtgttaaga gaaagatgag gaaagaagta  55140
tctgcttcta atctcttgaa attatctcca aattgaaatg gtattttggt tgcctaacag  55200
cctgaagatg acaaatatcc cctacaaatt tctcctattt taccctcttc ctaactatat  55260
ctgtaattta aagtttcaca tattcttttg aaaattgttt tcattgttta cccacttttt  55320
aagaaaagca aatgggaaca tactaccact gtttggcccc tttcaaaaat tttatatctg  55380
aggaatcttc catattgttg tggacatcta cctacctgat tcttttatta actacctttt  55440
atttcatttt atgatcatgc tatcattaat aggcccctat gatgaatata taagttgttt  55500
ccagtttttt ttttgtcatt gagaacagtt cacatatgta tcttgttgtc ttttccaagt  55560
atatctttaa ggcaaattct tagcagtgga gttgctaggt ccattgcgtc tatggtttaa  55620
actagtgcct tcaaaaatgg tattttatat actcactgtt taagagtgct tcttccttct  55680
atccccacta actttggcaa actgaatagt ttcaaacttt aactttttat agcttgttgg  55740
caaaaaatgg tatcttgtta tttgatcgtg ttttttaat tgtgaggttt agcgactttt  55800
tgatgtattg gtcttatgta ctttctggtg tgtgtgtatg tatatactga ccctattttc  55860
aacttatttt tcttttagtt tgtttgtatt ttccttaatg attttcagga aaccaatttt  55920
attctttctt cagacagttg tctaatgttc tgcttctctt gccatttgaa ttttgtgact  55980
acaaaattca gatgaaacaa taatagcata aagaacttgg tgggttatct tttgttttgc  56040
attattgatt gtttattaag aaatattctt taaaagtcac cttgcttaaa ttagcaagta  56100
ggaaatgctt tcaataaaga gaactgtcat gtacccacta ctccttactt actgaatcat  56160
cttcttttgg atagagaaga taaaagtgaa aagggaattt aagagttcct gccttttttcc  56220
ttgtctttag cattatatag ctgtttaatg tgtgggagtc taatttcttt tttctttctt  56280
gagacaaagt ctcactctgt tgcccaggct ggagtgcagt ggcacagtct tggctcactg  56340
caacctctgc ctcccaggtt caagcaattc tcctgcctta gcctcctgag tagctgggac  56400
tacaggcatg tgccaccatg cccggctaat ttttgtattt ttagtagata tgggacttca  56460
ccatgttggc caggctggtc ttgaactcct gacctctagt gatctgcctg ctttggcctc  56520
ccaaagtgct gggattacag gcatgagcca ctgcacctgg cctaattttt ttattgttct  56580
ttttggtgtg aacattctcc cctcctccaa gccttttgtt tttactattt tcatgttcct  56640
ttatatgtgc tgctgttttg tttcatctgt aattatctct catccccttt tttggctatt  56700
ataatatata tatgtacgtt ttgaatctga gctttgaagg taaattcact gcagctgtgt  56760
tggttgattt tagataattt gtgtatttcc tcctttgtct tttttaaact ggagtcattt  56820
gtagttgttt atacagaatt ttagttttta aaaccacaag tctttcatta taggttgagt  56880
tatgaattca tagcctgtta tttaaatgaa gcttttgaaa tctgttttac tgatctgtat  56940
```

```
catatctaac tacgccagta tttccttcct tgtctgacgt gaactctaaa attatgtgaa  57000
cactttctcc ctgtttcctg gcatttccac tcaaacttgt tcctcattct tagttagaaa  57060
tatatccaga attgtagttt ctttctaatc taatgacaga agcaaattaa tcaagcatgg  57120
caagaattta ttggaaaact gcatgtagtt gaaaatatgt ttagtatata ttttgacagc  57180
tgtgaagtct ctaattttta ctgtaccttt tctctgttcc aattttatgc tctattctaa  57240
ggatgtaccc atttctacta cctgactagg gagcatgtgt attgtatccc agcagatttt  57300
ttttttcata gatagatatc ctttagatat ctgttatcca gtgtaggtag ccactagcca  57360
catgtagcta tcattatgtt taaatgtaaa taaaataaaa taaatttact gagttgtttt  57420
tgctagctac atttcttgtg ctcagtagct acatgtggct tgtgattact gtattaagac  57480
agcacagata cagaacattt tcattattgc aaaagttctg ttagacagtg ctgttctata  57540
cagtgtcatt ctgcctctca ttctaaaaag ttctaattcc tgaagttgat gtactctttc  57600
tgttgctgtc ctctagctta atcaaaataa atttgagtct ttttaaaggt aggttgcatt  57660
ttacatactg atatttctaa atcagaggct atttatatta cttttttat attactttta  57720
aaaattagct ttattggagt ataatttaca tgcaataaaa tctacccatt ttaaatgtac  57780
ggttcattga cttttgagaa atacacacac acacacacac acacacacac cttcttgtaa  57840
acacacacct tcttgtaaac acaacaacca agatttagaa cactcgcttt atgaaaagtt  57900
tccctcatgc ccatttgtag tcagtcccca aacctggttt caggcaatct ctgatctgct  57960
ttctatatgc tttgcctata ctaggattac atataaatac agtcatatag catgtattcc  58020
tttttgtgtc tggcttcttt cttttagtat aatatttttg aaatttatcc ctgttgttac  58080
tagtatcaat aatttgttct tttttattgc tgactaatat tacattgtat ggatatgaca  58140
tttctttatt agtgtggtgg gcatttgagt tgttttcagt ttgggtctgt tatgaacaaa  58200
gctgctgtaa gcattcatgt gcaagacttt tgtggacata tatttttgtt tctgtttatt  58260
caataccttt gagtagaatt gttgggtcac atgatgtaga tcagttgaac agagtagatt  58320
ccagaaaagt tcacatacac atttcttgac aaaggtgctg agattattca tgggaaaagg  58380
ataatctttt aaacaaataa tactggaaca atagagaaaa caaagtgaac cttgactttt  58440
atgtcttatc atatacaaaa attaatttga agtggattgt tgacctaaat gtaaaagtaa  58500
aatttaaaaa tataaaactt ctagatgaaa acataggaga aaatctctgt gacttttggt  58560
ttaaagattt cttagacagt acatataaaa ttaactatat aaggaaaaaa tggacaaatt  58620
tgactttatc aacattaaaa atttctgctc attgaaagac tcaaaatgaa aaggcaagca  58680
gttttggaga aaatatttgc aatacatata tctgaaaaag gacttgaatg tataatatat  58740
acataaagat gctcttacaa cttcataatg agaaaataac cccataaaga gaagggcagg  58800
ccgggtgcag tggctcatgc ctataatgcc agcacttttg gaggctgagg tgggtgaatt  58860
gcttgagccc aggagtttga gaccagcctg ggcaacatgg tgaaacccag tctctacaaa  58920
ataaaaaaat acaagaaatt agctgggcat gatggcatgc acctgtagtc ctagctgttt  58980
gggaggctga ggtgggagga tagcttgagc ctgggaggcg gaggctgcag tgagctgtga  59040
tcgcaccgct gcacgcttgc ctgagcaaca cagtgagatc ctgtctcaaa acaaacaaac  59100
aaaaaaaaaa acaaaaaatg gaaacagaaa ttttacaaaa gaagatatat agatggccag  59160
taggcatatg aaaagatgtt taaaatcagt catcagggaa atgaaaattt aaacgtaatg  59220
agatagctca tatttactgg aatggctcaa aaagggctta caggaattgg caaagacata  59280
```

-continued

```
gattaactgg aactcttatg catgttggtt agagcacaaa atgatatgat ttcttgggag  59340
aaatatttgg cagtttttaa gattattttt gatagccttc tgaatttctt agtgagttat  59400
aggtcagttc tgccactgtt tctttctttt ctttctttct ttctttcctt ccttcccttc  59460
cttcccttcc ttgcctgtct tgcctgcctt ccttgccttg cctgccttgc cttcctttct  59520
tcctttcttc cctttctttt ctttcttttc tttttttttt taaaggagtc tcgttttgtt  59580
gcccaggctg gagtgcagtg gcacgatctt ggctcactgc aacctccacc tcccgggttc  59640
aagcaattct ccctgcctca gcttccccaa tagctgggat tacaggcgcg ttccaccata  59700
cttggctaat ttttttaatt ttggcagagg cagggtttca ctgtgttggc caggctagtc  59760
tcgaacacct gacctcaagt gatctgcccg ccttggcctc ccagagtact gggattacag  59820
gtgtgagcca ctgcgcctgg cctggcactg tttatttctt ttccctccag ttttatacct  59880
atttagagag attagatttt cttgagtact aggaatcact atttttgagc agaattattc  59940
aaaactgtta ttattttttc tttaacttga ggcaatgtag gagaaagcag tactgtgcag  60000
gtgaaagtta caaacaagaa cattttaaac aagatagtta ctttccatgt attggatacg  60060
taacagaatt aattctaata accatcctga agatggtcag gaggcattag ttaagaattg  60120
aaatgtttgg agcttgcctg tgttgatggg attaaggcag ggatgattta tgtgtaaatt  60180
tatgcgttag taacagcagt aaccgctgta gttacactag ggttctaaga gcaaatgttg  60240
attaaacatg aatgtagcag gagtgataag gtttggctct gtgtccccac ccaaatctca  60300
tgtggagttg tgatcctcag tgttggagga ggggcttggt aggaggtgat tggatcatgg  60360
gagtggtttg taatggtttt agcactatca ccctagagct gtctcgcgaa agagttctcc  60420
tgagatctgc ttgtatataa gtgtgtagca cctcccctct ttgctctctc tcttcctcct  60480
actcctgccg cggggacgtg cttgctttcc cttggccttc tgccatgatt gtaagtttcc  60540
tgaggcctct gattaaacct ttcttcttct aaaagattac ccagtctcag gtagttcttt  60600
atagcagtgt gagaatggac taatacaagg ggaaatatat atggttacca aatagcgaat  60660
tagccatggg aaaaagtagc aaataaataa ttattttact ttttcagatg ctaatttttc  60720
ttttcgttta ttttaggatt ggtgggagct gtccaatgtc cttaggctgt tttccaaatg  60780
agataccaaa agctagttct ccatcgggtt tctcaggctg ctagaagcat tcattattat  60840
ggttgtcatt acttcgagtt ctgttgccgc tatgcccaca gtagtatttg ttacataaca  60900
ggtgcttgat aaatatttgc taaatgaatt tttggaaaat acaatctgcc acacctttct  60960
tctacagttt acaatcttct gttgagatca tccgatagat ttttttttctt agatattgta  61020
cttttgaggc ctcaaattgc tgtcttttgt attttctatg tctgcagaga ctttccatct  61080
ttcactcatt gtattcattg ttttttaaca tctttgtaca tatttatagt aactgtttta  61140
aagtcactgt ctgttaattc aaacatctgg ttcatcttgg agtctgattc tattgcctgc  61200
tctttttttct ttgtaatagg tcatgttttt ctgctttgcc tgtctagtaa attttaatcg  61260
tatgttgaaa tgtagggagt ttggattgtt acttccttta agggtgctga gtttcatttt  61320
gtcaggcatt taaattgata gttgatttag tattgtcagg tttggttctc tttgttaaag  61380
caggcatttt tcagatttgt cttttgtcct agggcatggt ttttaacttc aaggttgccc  61440
tttccaatgt ctcagctaag tatctggggt gttccatgag gtctcttcca ctttgcctag  61500
gccagaactc cagcttctcc cagtattata tttcgttacc tctggcgtca tctccgttat  61560
gctttcagat cctgcgcata gacagcccag cccccagcca aggacctgag atgaaatcca  61620
tacaaaattc ttagtccctt gctccacaaa ctccaacagc cttagcagtc taatctcttc  61680
```

```
ctgtttacct cagtgaaatc tgtgttccac ttgagttcca tttccttctg tatcagagaa  61740
gagccaccat gctgaaagca aggggcacta tgtttctttg ttcttaagga tggtagccta  61800
tctgcaacaa ctgtagtgtg atataaaaat atataattta tgttgctgac agttacaaat  61860
actgcttgca gtactttgta acataatttt tcagattcaa gttcatatac tctttttttc  61920
cacatcacca cacacatatt ttcagacttc ctcctcatcc ttcttcttgc cagtagttgt  61980
attataattc ctgccagtag ttacattata attttggtta tatcaatatt gagtttttat  62040
gggattataa ctagataaat gccattcata gttaagtgat agagtatatt gtgacttttt  62100
tcctgcatgt tttatttttt ctggacttca cagttgtctc tctttttttt aaaaaaatta  62160
gttttcaatg ttcttagctt taattcataa actcacccct aattgtataa atctctcaac  62220
atgtttaagc acatttggca ttatatcaat tttatctttt ccaggtgcct tctaatctgt  62280
cccagtctgg actaattgtt cttcctggct tgctgtatgg ctgtctactc aagatgtccc  62340
ttcaccatca ttctagggat tcccttttcc tctcttgtgg gttagattct tcagttcttg  62400
gagactgtca tcttctttca tggtttccca ctcttgtttt ggcggagcac atctttagta  62460
acttcctgac aaagtgtatg gtttgagatt tcgctgattt taaaatgccc ttattatata  62520
gtcacacttg atttatagtc tgtcttggta tagaattcta ggctgagaag agtttccct  62580
caaaatcaga aggttttgcc caattgtttt ttagctgcta gtattgctgt taaaaaggat  62640
aatgtcattt tgattctaga ttcttttatg aaacctgttt cttctctggc agcttttagg  62700
atcttctgtt tctttggtat tcagaaattt catgagatat gtgtgcttct attttggtct  62760
tattttcatc tgttttgcca ggtactcatg caactttcca gtttgaaaac tcacatcctt  62820
cacttttgag tatttttctt gagttatgtc ttcggtttct tctcagtgtt ctctgtttct  62880
ggaactccta aaatatattt aacatcctga actcttagtt tttgtttagt cttctgattt  62940
tcatttgtct ttttattctg tatattctgt taattcctcg gcttcatggt cttctagccc  63000
ttcttttgcc tatcttatgg ggttgaggat taaacagttt atatacctga ggtgcttagg  63060
atatgtctgt catatagtaa gtgcttgtgt tagctgtaat tgttgtttac tttcataact  63120
gtcttgaggg aaaggtcttt ggtcttgatt ctttgacttc ttggctgtac atgaccttgg  63180
acgagttatg taatctcttt gagacctacc tccctcttct gtatagtgtt aataagctct  63240
agctctcaga tgtttgtgag ggtcgaatgg agtatatatg tgaaaatgtt taataccttt  63300
gtacagaatt aatagttagt acgtggatct ttcaaatatc aaaagtttc agtttgatgg  63360
gaaaatgatg tctgaatttt cagggttatt tttaagagta cttgattatg actgtcttgt  63420
aaatctctat gagctaggta tacttgcact aaatgctaat gctttttaaa gaagttatgt  63480
cttaatattc agtctcatta tgttaggttg aagatagaag attatgaaaa tattctctga  63540
aaagctctgg ttttacttca gattgtataa atctgtgtaa tgtaataatt atttaagaat  63600
gacatgatta ctactctaaa cccatagaag gggtatttgt tggattattt attttcactt  63660
aaatggtatt tgagattagg aaaaagaaaa tctgtctttt ggtttttctt gatagtatta  63720
atgtaatttc aaatgttagc tcatttttgt taatggtggc tttttgtttg tttgttttgt  63780
tttaaggttt ttggattcaa agcataaaaa ccattacaag atatacaatc tgtaagtatg  63840
ttttcttatt tgtatgcttg caaatatctt ctaaaacaac tattaagtga aagttatctg  63900
cttgttagag tgaggtagag ttaaagatac attttaacag aattgtattc ctaaaccgat  63960
taagtcaaga agtccaagag cattgttaga tcatttagaa agtgtagtga tgaggtaaaa  64020
```

```
cattgttggc acagattcat gttacttgat ctgctttaaa tgacttggca tctagcccat  64080
atttgagccc ataaccgtgt ggtaatttga agtgtaattc acagtagagc ttctgttaaa  64140
gcactaatag catcttccat ggaggtatac ttcagagtga atataatttt gtttatcctg  64200
tgtctctaga gctattgact gaaaaagctg ttagggcatt ctctaactgt acatcaccta  64260
agttatttaa aattgctgaa ttaggtggct tgtcttgtct aggacagagt tttaaggact  64320
gcccacctga ttgatagagc tagttgacct tatctttaac tttttgtttt tcttttgact  64380
ttgggagtag agatgtgaaa aggtaaaaag gaaggaagga agagaaaact taactctttt  64440
tgcccatgaa gactgttttt ccttctcaaa atattgacta ttttctgatt tgtaaaaatc  64500
ggcacataaa acgtgttatt ttttacttga cttttatctt tcccatgtga tatctataaa  64560
ttatagatag gaaaaattta tctgtaattt agtgatcttt ctagtgtgat aaaacgtcag  64620
aagtactgag agtggagtgg acattgatat tgttactctc agtaagtttt cactgatttt  64680
tctcagagtc atgaaggaac aaacgtttgt taagtcctta tcacttatta gataacacaa  64740
aacatgttgg gggggtgtgt acagaggtga gtaagatgta gctcccattc tcaagtcgct  64800
tacattctaa tgtaaaaggt agacaaagca ttacagaaga agtaactctg ctatagaagg  64860
ttgcaatgaa gagaacattg gaaacactaa ttttacctta taaagaaggt ttcataaagg  64920
aaggcaagtt tgagctgggg tgaaaaggac cagtaagggt tgactttcaa gccaaggaga  64980
ggaggggaag tgatgttaca ggccaaagga atggcattgt aagaagcttg ttggcataaa  65040
agtgtttaga atatggcagc gaattcatta tcatcagatt gtggtgtctg tatgttgggg  65100
gtgggagaga attgtggtgg caataggcaa caagataaaa gaaagtaaaa ggtgttatgg  65160
aaacttaatg ggtccagctt acaaatgatc tatgcattta ggggtctttc tcttttcctg  65220
ataaacctct cctacaaaga gccttgttgc ggataccata gtgtttcttt ggaggaaaat  65280
aaaaactaca aagctttgta ttttttgcac aactggattc agaatataag taataaaaaa  65340
ggacaagaac tttcaaaagc tagaagccat taaactgagt cacttcaggg ttagactatc  65400
agaactgggg atttagaaag tctcagaatg gaaatcgaag gacaccaaag acaaattcgg  65460
cctttttcaa aattttattc tagtttaaca tattcaaaga aagggaagga aattcttttc  65520
attcctgtgt gtagtgactt cctgctttaa gaacttagga cttcagctgt actatcagta  65580
ttgtaggcca cttaacatta ttatggttaa agttggcatt ggagagagcc taggaaccta  65640
actgcctgtt tgtttttata tttccaacca ttggattccc aagttaatga agtctgttta  65700
ttagttgagg gtagctctta atgcatatat tttaatgccc cttccccaca tggaatcata  65760
agctttcaga actggagagt acctgaaaga gatcatttag tccaaccttc tcattttaca  65820
gatggggaat ctgaggccta gagaagttaa gtgagttgaa caaggtcaca caggtacata  65880
tggtagccga ccatccactg tttatgccaa tattcccttt acgttttgct tttttgcttg  65940
ttcgttttaa cctctccaaa ttttactgac ttcagaagtt tctagaacta agttatagca  66000
tgttttgagt tctaatgtca ctttccgatc ttctttacct tttttctacc tctgtttgta  66060
tttctggttc tggttaagtg agtctggtaa gcagcaggtg ttctatttta tttcttttat  66120
ttttaggata gtattacatg tgatatatat gtctttgcaa acatacataa tttgaagatc  66180
ttaaaatatt tgcactaggc atacccacat ttaatagtat gttaaatctt ttatagcaat  66240
tatgatatac atgggtgaag aagagttcct aatatggcct ttctgattaa ctgtatctgt  66300
ttatatctgt gttttcttca ggcattcata acattaagca aattcaggtg tactgttact  66360
taattgaatt aatcagtttg ttttgtacaa gtatatttta tttttgttcc ttgttgtata  66420
```

```
atctggtagg aatggggaag gggagatagt gaataaagag atgtatactt cttgcctttg  66480
aggaatttaa gttttcactg tataccaatt ttttaaaggt atttactata tttcagtgca  66540
tattttattt gacatacttt atcattttgt ggtaaacctt tagctttact aattttcatc  66600
tattaagttt tcttttgtaa gatggtgata gcttcatcaa agagagtaaa gaagagacct  66660
gcctacctag ctgattctat ggcaaatctc acttctctgg aagcttttcc tgttaatctt  66720
attccttcag tttctgcctc ttgtttcata aaaactcatt ctttaaatgc ttattcattt  66780
ctcttgtctc atataaacca atatgaggta ctggtatctt ttgagtttta gttataagga  66840
agcataaatg gttaaattta aatggctaaa ccccatttgc catttgtgta tctttaattt  66900
tagtttgttg agagacttat cactaccaaa ccacaaagaa tttaaaagaa actgtcagta  66960
ggtataggtg gaaggagggc atttatcaga gattttaatt taagaagaaa gtcttcatcc  67020
ttatcctacc aacccccatt ccctgagcat atttatcatt actagtccca gcatatttgc  67080
tcccatattt cctatgctta cctgtgaaga ttttcataac tttttccttg ctttttactg  67140
tcactgttgg ttctgtgatt tatgacagat actgctcttg taggaatgct ggctttgact  67200
gaaatttgtt actgcttttg tatttaaaac ttttttttta ttataagtag aattatggaa  67260
cagtagtaga aaaagtttga cttttgtaat cagagatact gagcttgagt tctggctctt  67320
tcatttgtat actgttattt ggggcaagtt ttttaatgct cttaagtctt agctttctca  67380
tatataaaat ggagataata acagttatca cgtgattgtg aggatgaaac aaaaaaaagt  67440
ggaaactctt tgtaaggtgt gttcatctgg ttgacactta gtagtcatta cttccacttt  67500
ccgtccatat agtcctctta acagtaatat ttgagaggca tttttattaa agcagtctta  67560
aggagtgttc gtcaaaccac atgttctggg atcctgagaa agtaggggaa gtttagagaa  67620
ctgaagctgc acaaaactaa tgtttatttt ctgttgtgtt gtcctgagac cagcttctta  67680
gattgtgttt cctagtccta catctctgat tccttataaa atattccatt atgaattctt  67740
cactattgac aatttctccc cttttatctt aaaagtacca aagaaagtgt aaaatgtgac  67800
tgtcttgtca gtcctctttt tcctgttttt catgtcagtg ggtatgaaat tactagcaag  67860
gatgcatata tgtgcatatg tcattactaa atgcattttc tttctagaaa aactcaatat  67920
actaaattgt actaaaaagg aaaagcttgt tttgttttga gtggtagtat gaaagttgtt  67980
ttattttagg tctgaccagt tagaaaccaa tggattgtag tttatttata attagttaaa  68040
ccttcatgtg aatttggttt tgaattacct ttaaggtaga gaagaaacta tatagatgtt  68100
tttcagggtt tctaaatgta caatacaggt tcacaatcac ttatttgaaa ctcttggggc  68160
caagtatgtt tccattttca gaaattttag ttttcaaaag gtagcacaga taaatatact  68220
tttacataaa caccccagtg gggtgtgggt cagtacctga aatgaaatgt tttactcttc  68280
gctctaagtg tattaaatat tatgtacaat cttattactt cagatcagga tttgctgtag  68340
ttgagtttgc cataaaactt aagagaaaat tttagatgtt ttgaactttt gggatattga  68400
aattgcaggt taaggagcta tggaccttta tttgttttaa aatgctaaga gtttatttta  68460
agtaattttt aaaaaatttg ttttgcatag tagttggagt taccagggta ctgctaacca  68520
cactgatatg taagatctct ttctgagcct tttattgttt gtaaacatgg cctgttaatc  68580
attagaaagc cagtacatac taacatatca ctgctattaa gacaaatatt agcatactct  68640
agtaatgaca agtcagcatt ttactattct gtattgattt tacttattct ttcattactc  68700
tcatactgta attaaaactt gcaatctgag agactgttga aaaaggtgat cgttggcttt  68760
```

-continued

```
tcaacaggga gtaaggtctg gtttaaaaaa aaattagtaa gcatttggcc aagtagatta  68820
acaacattca gtttttcttt actgtcctta tgcttttact atttttaaca tatatctttt  68880
tgaagaatag tttgagaatt atgtatgctt aactatgaga tacagatact attgaaacta  68940
gtcagttgtt tataggtact tgtaaaatta aaaatatatt ccaatagcat gcagattttt  69000
catagaggaa atttgaaagc atggaagcac ctgaatttac agtactctgt attagtggca  69060
tcacaagttt ttaagcaaat gtattagctc taattgcata cacttaatct tttaagcttt  69120
ggttttatta ttataatatg gggtgataa cagtatctac ttaatagaat tcttgttatt  69180
acatgaaata attaatgtta aacacagcat aatatgtgtc acattataaa gattcaggca  69240
atgtttgtta gtattagtac ttttttttct tcctaagtgc aaaagataac tttatatcac  69300
ttttaaactt ttcttttagt tgtgctgaaa gacattatga caccgccaaa tttaattgca  69360
gaggtaggta tgaatgtact gtactatgtt gtataactta aacccgatag actgtatctt  69420
actgtcataa caataatgag tcatccagat tatcgagtga gatacatatt taagaattat  69480
ctttaaaaat ttcaaaaatt ttaattttac tgttgtgttt taggaaaaag tattgcataa  69540
agctattaat attgtcagga agactaaagt gcagcataga ctaagaatta ggaaaattcc  69600
tagactaaaa atagtataag gagagggttt acctactatt tgaggcagtt ggtctaatag  69660
taagcaatca cagggagaaa gcagaactac ttaactcttc tgtgttgagg aatgacataa  69720
aaggtaggaa aggatataac aaatgttgat aagaggagtc tgatggatga gaggagggaa  69780
ctgctttaaa tgagtttcta cttcagacat aagttaattc tcagagccca caaaaacttt  69840
cacttttatt tgtgaaatac aactcagttc tcatggctta acactttaaa ccatgagaaa  69900
actgaagagt tgagaagctt ggcagatgct gctgtgatag tcaaaaagaa agtgggtgcc  69960
atgagctact attgatgtat ttgccattga tccctcctga aaatctagaa tggactttca  70020
gacaaatggt ttgaaaattc taaatcacta atgattgaga tttagtatag gtttactaag  70080
aacgggtttt ttttgttttt gtttttggtg gatttaggct gttgcttact aagcaaagca  70140
ggctttagtt gaggtttatc ttgctttaaa cagatattta acagatttc ctggaggttt  70200
ttgtgtacca ctgggaaaat gaagttaggc agatgactaa gtgaaagctg tcctgctgac  70260
tccttataat gatagtcatt gtctaccaga agatctctcc tgtcacacca aaggataatt  70320
gattatatcc tgtaccatat tatgagtcac ctgattggag atataagaca tacttctcac  70380
atatttagat gacacaggtt agtacattga atatcagcca gggtttttaa ggatcttaat  70440
agagtggaac taaggtagaa actattaaga gcaattaata gtgatatatc tatagtcctg  70500
tttctaaaca agttttttta aaaacctcaa ctctgactat agtgaacaga gaagtcttgg  70560
actcttacaa ttcatgtgag aagacctgaa actttgataa caattatata cattttgtga  70620
gtaatttctt tggtgtatgc cttcacatat ctctggtatg tgacctatgc tgcagtccat  70680
tgagcataga ttcccagaat gtattctcct gcagaaaatg gaggaaaata atacttggct  70740
tccctaatga ttacatgtgt atacaacact aacatttgca agaccacctt taaataacac  70800
acttagcatt tttattttat gaaatgtaat atgtagttct ttgcatagtt tatcctatta  70860
gtaatctatt ctgtctttgg aatatgtttt gtgatgatga aataaatact ataaatagta  70920
ttattccttt tgcattgaga gtcctgacga aatgtccatg tgacagttca ttttgggttt  70980
agctctacct ctaatatgtg acctatgcta ccagtccgta tagcgtaaat tcccagaata  71040
tatcctcctg aataaaatgg gggaaaataa tacctggctt ccttaatgat tatatttaag  71100
acttatcaag agactatttt ctatttaaca attagaaagt taagcaatac attatttttc  71160
```

```
tctggaatcc agtgtttctt ttaaatacct gttaagtttg tatgcaacat ttctaaagtt  71220
acctacttgt taattaaaaa ttcaagagtt ttttttctt attctgaggt tatcttttta  71280
ccacagttgc acaatatcct tttgaagacc ataacccacc acagctagaa cttatcaaac  71340
ccttttgtga agatcttgac caatggctaa gtgaagatga caatcatgtt gcagcaattc  71400
actgtaaagc tggaaaggga cgaactggtg taatgatatg tgcatattta ttacatcggg  71460
gcaaattttt aaaggcacaa gaggccctag atttctatgg ggaagtaagg accagagaca  71520
aaaaggtaag ttattttttg atgtttttcc tttcctcttc ctggatctga gaatttattg  71580
gaaaacagat tttgggtttc tttttttcct tcagttttat tgaggtgtaa ttgacaagta  71640
aaaattatat ataaatacaa tgtataatat gatgttttga tgtatgtgta tatacattgt  71700
gaaatgatta ctacagtcaa actacttaac atattcatca cctcacataa ttattattct  71760
ccccccaggg tgaaagcatt taagatctac aagctacaat tttcaattat acaatgttat  71820
tattaactat agtcactatg ctgtccagta gagcttcaga tcttgttcat cttgtgttcc  71880
tccctcccca ccctcagtcc ctggaaaaca ggttttaaag atagttgcta atccttattt  71940
cttctaaatt tttaaatcag ttgctgcctc aatttctata tgagaaatga ctgattgatt  72000
tcatttttct gttcacgcta ccattttcat atcatactag cacatgttac ccattaactg  72060
tattgcagat ttggtctcac aaaattcttc taaaataaca tttttaaaaa gcatattaat  72120
caaaaataag ctttatattt ctgaagcttg tttgagcata gaatgccttt ggataaaata  72180
ccattaccta gtaaagtgtg aacttttata atccataaaa attattcttt tataagaata  72240
ttcataaatg tagttagatt aatagaagat tctcgattct ttgatcagaa aactaaggac  72300
tatattgaaa aatcagtgac aaatttaatt cttatagtac atctgaaaga aaaaagaaaa  72360
ctcttgggag aacttttaca gtgatttaat tttgctgttg atatatttct ttgggtggta  72420
agtatggcaa aacatgttaa aatttaatgc aaagagattt tgtacatttt tccatctcta  72480
agaaggacaa agcctaagcc cctccagata gatagaaaaa ctcatttaga gagttctcct  72540
tcatgttaat ctaatttctt cttaattcag ctgtaaaaca gaaatagaat gatcgtatta  72600
atcatttaaa gctgtgtaat tgcatagatt ccttgttcct ttaccccctc ttatatcttg  72660
tttcctatcc tttgtgactt tttttgcatt atatataagg atgccgaaat actgtttatt  72720
gttgatagtt tacaaaattg aatcttacat tagtgcataa ttttggtgaa tgttgaagat  72780
tatggtagat tgccttacat ttctgcatat tgtttgcacc ttggaatgat agcactggca  72840
tgaattatag agctgaggat ctaaagattt ttactttgat ttatcccatt atcatctgca  72900
gggaaacaat tgcttttact gattaaaaat gcaggctggg cacagcggct cacgcctgta  72960
atcccagtac tttgggaggc cgaggcgggc ggatcacaag gtcaagagat cgagaccatc  73020
ctggccaacc aacatggtga aacctcatct ctactaaaaa tacaaaaatt agctgggtgt  73080
ggtggcgcgt gcctgtaatc ccagctactc aggatgctga ggcaggagaa tcgcttgaac  73140
ccgggaggtg gaggttgcag tgagccgaga ctgtgccact gcactccagc ctggtgatag  73200
agggagactc catctcaaaa aaaaaaaaaa atgcagtagc aaaagcgatg gtagaaattt  73260
aaaacagagt tgatgagcag catatatttt ggtagtggaa aaaaaggtaa aaaatttttt  73320
gtaataaaat agaaaaattt tgtaatgtgg aggcgcagaa cactagattt aagccagggg  73380
gtcttaaatt gtgttacatt ccttttaaag tctgatggaa ggtataaatg ttctcccctc  73440
aaaaaatgtg catagtgtac ataaaatttt gcagttttta ttacattgaa atatattctt  73500
```

```
ttagacagaa tgtaaaagaa ccttcatgaa aactatgtca ctttttttatg caaaaaccag  73560
tggctactac atgagagcaa tgaataaatc taagtggtac aaattaacca aaattaagct  73620
ttagttctgt tcaatactaa attttaatga aaagactgct atttaacttt taaaataaca  73680
agttgaaact atgctctttg actttgactt tgcaactttt atatgatctt tgatatccaa  73740
tcagtgttga ctttggtaaa aagtgctgaa aatgctattt tacaaaagaa agaagagtaa  73800
atggaatctg tagattctat tgcctgatga aagtagacgt gtcaagaaat aagaattctc  73860
caaggctctt cagataaatt catgtttcat cattttcttt gccttcaagt tactgagatc  73920
atttttggca agatctgtat cattaatgct gtgttaggaa agaaaagatt atgactccac  73980
attttacttt caaggttgaa gagttaaact gtttaaaaag agtgtatgtt atcctgtaaa  74040
cagcagtatc aggctgtaga atttgtcttc tgaaagcagg gaacttatat atagcaaaga  74100
acttcatagt gctcccattt cttgacaaaa cctctcgaga agctcttgat tgaaagtctt  74160
ggctttcatg aatctggcag ctttcacaat agtggatttt tcatgacaaa tcatcttaca  74220
cagggaatta ttcaagggtt ggcacttgaa acagtagaat actttcacaa caagagataa  74280
gatttctttc aggattgatg acagtcttgc accctagcgc atactgatga agagagcagt  74340
gggtgaccat gacatggaga gcttctgtct ttaccagtgc cccaatatca gatgtgttgt  74400
ctggcagtaa ggtgtactgt ctgcctacag aatactgagg tttcttcagg agaagttttt  74460
tggtaaagaa actttaccat tttgaaagtg ttaatgtttt ctgaagcttc caaaaagatt  74520
ccaaaatggg aatgtttcct tgattgtgtc accatgcttg catttgatga aaacttgtag  74580
ccggctatac tgagaaatca tatctgaaga aaggtggtac ttccaatctt tttgtgacct  74640
actttattat tgttttttta atgtcagggt ttttttggga atggagaaaa gtatttgata  74700
gaggtattgc aacagtctta ttcttcttca tgctacaagt atatttgact ctttctaaga  74760
tacttgcctt cactgttcaa ctgtgtgact ttttgtttgt ttagcattac aatcaatatc  74820
ctagtaggat gatttaatca atgattttta attggaacaa atagtttttg taatggtcta  74880
ggcttttcca acttaactgt gctctcacat gtggtctctt tttctccctc tttcctcctt  74940
cttatacact ctcacccaca cacatatgca tacataccct gtctgatgta tctgcttctt  75000
cagaatagtt ggctgtgctc tgctgatgat gagaacttgc catttaagaa ggacttggga  75060
tagtccatgt catcatgttc agggataaaa gtaaaaccca agggcattta aactttattg  75120
tattttattt tctgtttcca gtccaaatta aatccaagag aaggctccat aatcaaaaag  75180
taaggacata ttttaaattt gccaatggga agatattcta gtcattacag tctggtaata  75240
ctatcaattc tgtttctctt cagaggtgag gggagactat ttgatgaaat cgtaagtcct  75300
gtagggtgtt gtgaaatagg gccagaatga aagatagcaa gaatagtgtt atgaaaataa  75360
aatgcaaagt ttataatatc atgtggtaaa atgtaatagt atttacttca tcagtagaac  75420
tgctctagta gctgtatatt ctccatcctt gcataggttg gaatatcccc caagtgaaaa  75480
gagattgatg ggctaatagt taatagaaaa tggagatctg tacatacagt gttaagaatg  75540
tagatattaa aattgttata tttagctgtt acataatatt aagactcaga gttaagtaat  75600
ttcactgaaa ttgattgctt tttgtgtctt ggagtcaaaa taaataactg aaatctacta  75660
tacttggctc atgcttaatt aatatactta gaccatattt cggatgaatt attcacagaa  75720
tctaaaggag tatcctcgtg ttcttacctt ctttatccct gtgtttattt aaaaaggcaa  75780
aaaaaatgga gcagatgctg ttggttgacc atattttact gaacagtagc atttgtgttt  75840
aggttgaaac agcattagaa aactagatac ggattaaagt cagtggtagg ttttttttt  75900
```

```
tttttcttcc aggaatgttt cttatagatg atcaaacagg cacaggaagg ggaagtgttg  75960
tgatcaatat tatccagtta atattagcat tcagaggaaa atttgagtcc tctgatacac  76020
tgttaaattt ctttctatac tatcaagtcc acaaatcctg gaactgcaaa agaattttga  76080
gactgttcaa aataattaat ctctgtatag gctcaggctt tcctgcaagg ttatgaaatg  76140
ctgataaaat tggtcttatt ttgaaaggct cctcagctta tacctttcct tacaaatgct  76200
tccttacaaa tgctaaagca tttaatgact cctgacttaa agggaatttg gacagattga  76260
ggttgttggt cttggaaata taatactgca ggcttctgta aaatacttga aatgtaattg  76320
ttttaaaact ttcaaagata ccacttgttt gcctgttggt tagaatactg gtgaaataat  76380
ttttaatctt ttatgaataa ctaatttcat cataagaaaa cttagctaag catggtaaag  76440
ctgttgttat acaactgtgg aattcttcct gaggagtaac tatcttataa taaatgtagt  76500
tgattatcta aagtagtttt attcttggaa tatctcataa taggtttatt ctcttcttgt  76560
cagtatttcc ttgtagattg agcctgtgga tttgcatttt tgtaattgtg aatcaccatt  76620
ataggagata catgcatttt atctactttt cagtttgtat ggggttaact ttattagaat  76680
tatctttaat gttattttgc ttatatcctt aattttaatt atagacaaac attaagaagc  76740
tggagaaaat tatgttctag tgacatttat atagaagaag aatctttttt cccccttcct  76800
tttttgaagg gagatgaggc agtcatattt tggtaaagaa tttgtagact ttgcagaggt  76860
ctcttcaaaa taatctggct cagagtcttg acatatcctc agcagacatg gtgcaaatta  76920
gatggcagag tggtgggtac aagttgacca taaaataacg cattaggtta gtaatgccca  76980
aataatactt tgggttttca gtgttgcaga gaagtcagac aactgatagt tattataaag  77040
aaaaatgttc tgagagtgag gtaaccgctt aagggaagga agcctccttc tgtcttattc  77100
actaatttac aagaagataa ttgtgttaca cttccttagg agtcattcat ttgtatattt  77160
gacacttttg ctttatgaac atgtgaagat tattcaaaag taagctgttg gtgatttttt  77220
tcttccaaga aagcatgcca cagggcaact tctagggttg gttctcatct agtcctgtgc  77280
tccacactat ctgcatctgc acttaagttt caatattaga taactcacat gtttaaacta  77340
tgaagaaaga gttaaaacat cctgagaatg ctagtaagta tgtatttttg aaaggacttc  77400
caaaatttga gtttaaagag gtaaactcct tttacatgac aaagttactt agaaacacta  77460
ctgctgtttc cctctccctt gccttctccc tgtcccatgc atacccccag ctgtgttcca  77520
gaatgatggc acataaagta aacattcata tttatttccc ttttttttgtt tttttttttt  77580
tttttttttt ttgcttgttt gttttgtttt tttgtttgag acagtctcac tcaatcaccc  77640
aggctggagt gcagtggcaa catctcagct cactgcaacc tctacctcct gagttcaagc  77700
gattctcctg cctcagcctc ccgagcagct gggattacag gcgcctgccc ccacgcctgg  77760
ctaatttttg tatttttagt agagatgggg tttcgccatg ttggccagac tggtcttgaa  77820
ctcttgacct caagtgatcc gcccacctcg gcctcccaaa gtgctgagat tacaggcatg  77880
agtcactgtg cctggcctct tattttttct ttggttaaac ttttagggaa aaagtttgag  77940
ctgcttttaa ttttcttttt gtttttaaat aaattattaa agtttctcta tgttaggaac  78000
tcttgtgtac atgagttcat tgagcttatt cttaataaag acaaatcttc tagaaataat  78060
agttgtatct ttaaatgatc tcaaggaaaa tgtttggttt ctctggggaa tgaattttca  78120
tgacctaatc ttaaatcagg ttattttttc tagcctgttt actaaatttc tacatgttat  78180
aacctaatga aattttctta cttcctcttt atttaaaaca aactataatt actgtctttt  78240
```

```
taaaaatctt ccaatgtggc gttcttattt ttcttaacat ttgaattttc ctgggccaaa  78300
ccatgttact atgatacaca ttatttaagg ctgttatata atacagtaaa attgtagaac  78360
tttcatacct tgaaggatct tagcaattat ttaattcaaa cccattctaa catagatgat  78420
aaaacagatt tgcagggttg ggcacggtgg ctcataccta tattcccagc actttgggag  78480
actcaagcgg gaagattgct tgagcccagg agttcaagac cagcttgggc aacatagtga  78540
gaggctgtct ctacaaaaaa atatttaaaa aatagccggg catggtgtca cgtgcctgta  78600
gttccagctg cttgggaggc tgaggtggga ggattgccag agcctgggag gttgaggctg  78660
cagtgagcca tgatcacacc acagcactct agcctagagc ctccctgtgt ggcaggctct  78720
acacttcaga taggcaacag atcgagacct tgtttcacaa aacgaacaga tctgcaaaga  78780
tcaacctgtc ctaagtcata taatctcttt gtgtaataat aaaaaacccca tcttctaacc  78840
ttaaacctgg tatttttttc tacgaaacta tgttctgcag tccaaattat ttttctttat  78900
tattttgaat cctaaagtag aaatagaaac ttagaaaaat aaaaagcaac tcctttatga  78960
catatgagga ctttttcagt tttaaataag aaaaacccaa ctcaaagtag cttaaataaa  79020
aggagacatt ttttgactta cataacctaa aagctctggc ctggatctag gtgctcaaca  79080
gatctcaaga gtatctctct tattctctct ccctccctta ccctcctcct cttttctctc  79140
ttctgtatat atgttatttt caaacaggct ctcacaagta gtggcaagat atagttccta  79200
atagcttcag gtttgcattc tacctacttt agcaactatg atgagaagag agctacaatt  79260
tgagcaaaaa tttgtagggt gagttctgat ttccctggat tgaggcacat gcctattatt  79320
cctgaaccaa atattctgtc cagggaatgg aattctctgg ggcatgtatc taaagctgaa  79380
gtgtagagcc tgccacacag ggataataat agttttccaa agaaaaatca aggaggggaa  79440
agaatgttgg aaagagaaaa aaatatcagt tgtctgcttc acatttgttc tcaataatta  79500
gtttcataga agtgaaatac tgtgtaacac cctaaacttt agagattctt cgtagacagg  79560
aaaaataaga actcaatgaa gttgtgactt cattcaaatc acgtagttta tatacatgct  79620
attagtaaaa cccaggacag ctgagtacaa gttttaccct tatattcaca ttgaggtcca  79680
gatcctggtt ttgaatgaga taattacgtg cagtcggact gttttctgat cctaaaaata  79740
gagacaataa tatctatctt gtaaagttat ggtagtgtta aagatatata aaatgttggc  79800
aagtacctta atatacaata actactgcta tatgttgtca ttgtaataat aatcatattt  79860
cttcctttgt tgaattgctt tcctgtagta atcttattgt gatcatcctg aaacatagat  79920
ttccgagctt caagcaaaca ctattatgtt gaaaaatcta cattatttct aagtttagca  79980
gtgccagtgg aaagtttatt gaaatagaaa attacttttt taactgagga gtgtagattg  80040
tgaattcgtg attcatcttc ttaggagatg atcggaatat tgataaatat tgatgcatag  80100
aatatgaaca aaacattaca tatcttgtgc tgtgatatta aagtagtatt ctgttctggt  80160
agtagtatgg cagtatttta ggtctgaaag atgtacataa tctgtacttt gaagtctgtt  80220
ttttaagaga ttaatcacaa gagatttaca taaaacaact aaggttaaaa ataaatggtg  80280
gattagagat acatcaggca aatttcaatt tcaaaagcag atgacagaat ctcagtatca  80340
gggtagcatt taaagcaaaa agcattaaac tggatcaaaa atgtcatttt acatcaacac  80400
agggtacact ccaggtaaag acttaacagt tatgaacgaa tgtgctaaac atcaaaatgt  80460
attaagtaaa agctgaaaga aatgaagaat aattggtaga aaagcaatga taggaatcct  80520
taatgtactt caaaaggcac gaagtaagaa ggtacagtca tgtaccacat aatgatgttt  80580
gagtcaacac ctgacctggt atacgacaat ggtcctataa aattataatg gagctaaaaa  80640
```

gcttctatca cctagtgatg ttgaagccgt tgcaatgcaa tgtatcactc acatgtttgt 80700
ggtaatgctg gtgtaagcaa acttactgta ctgtcagttg tataaaagca tagcacagtt 80760
atgttcagca cataatactt tataatgata aacgaatatg ttactagttt acgtgtttac 80820
agtactatta ttttagcatg tgcttctgct tattaaaaaa tgttaactat aaaataatct 80880
ttaggcagat cctacaggag gtattccaga taaaggcatt attgtcatag gagatggcag 80940
ctccatggat gttattgccc cttaagacct tccagtggga caagatgtat aggtggaaga 81000
cagtgatatt gatgatcctg accttgtaga ggccaaggct aaagtatgta tttattagtt 81060
tttaacaaga gtttaaaaag taaaaaaaaa aaataaattt aaaaatagaa aaaatcttaa 81120
taaggataca aagaaaaaat gtttttgtgt agctgtgtaa tatgtttttg ttttaagtta 81180
aatgttacaa aagagtcaga gttaaatttt tttatattta taaagtgaaa aagttataaa 81240
atgctaaggt taatttactg aagaaagaaa aaatttttaa acagatttag agtagcatgt 81300
ttataaaatc tacagtagtt tacagtaata tcctaggcct tcacattaac tcaccactca 81360
cccactgact cacccagagc agcttccaat cctgtaagct ccattcgtgg taagtgccct 81420
atacaggtgt acaattttta tatcctttat accattttta ctgaaccttt tctgtctttt 81480
agatacacaa ataacattgt gttacagttg cctatgatat tgaatacagt aacttactgt 81540
acaagtttgt agcataggag ctgtatcata tagcctgggt gtgtagtgaa ctataccatc 81600
taggcttgtg taagtatatt ttatgacaca gtgatgaaat catccagata cagtttctct 81660
taagcaacac ataactgtat atatatatat ataggtggct ttaataataa aataatgaaa 81720
tatatttctt tttttctgtc attgacaaaa caattaccag tcttactaat tagatcaact 81780
gcaaaacaaa atctcactca aaaataaaaa tatgtaagtc ccattccttg attacaattc 81840
attagaactg gagattttta aaaatgttta aatttatatg gaaatataaa atcatgtttt 81900
aaataatttt tgattcaatg aggaaatgta aatttagaac taaagattaa taactagaga 81960
tttataaagg caaaaatgtt aatgaattag gaaacagtaa accatttgaa ctaatctaaa 82020
tactgattgc atgaaaatgc caataaaatc aatacatatt tttaaaagcc agtcaaggat 82080
aaaagaaaag agggaaacta aaagtgagac attaagtatg agaaaggaga taaaactaaa 82140
gtgtggaggt gatgttaaaa attatattca ggtctgtgct aatcattttg gaaatttcag 82200
tgagaagtgg gcaattttca gtgaatatat cattgtaaat gctttgagga gagacaaaat 82260
ctgaatagac cctgcaataa tgaaaatgtc taggagccct caagaaatac ctggtttaaa 82320
ttgcatttca ggtggctggt tatcacacct tgaagtatca agtaattatg ttatctaaat 82380
tggaccaggt gttagaaaaa tatgtgagac ttcacaggtg gctgcttatg tagcccttat 82440
accttaatct gataaaggta gcatatattt aaaaagagag aaaaccagaa ggtacaattt 82500
agggaaaatt aaatacttct atttggccaa agtaagagta cattcaaggg aattgtgaga 82560
ggtaagagtg gaaacagagg ttggagctgt atttttatgc tgtgattgaa ttacagtgtg 82620
tgataaatat tgctcttatt tgggtagatt accatttaac attttgaatt aattggtaat 82680
tggattaatc ttaactttta aaaaactaat ctgagagtgg tataaaggat agattacaga 82740
atggataaag ggtgataaat cagttggcta tggcaaaatt gcaggaagaa actgaaatag 82800
gccacagaaa actgaaactg acattttgag tagtatttca gaatcaagat ctggattttg 82860
gcaactgaat agatgcgtag gaatcaaaga tgagtatact aaatgaactt aatctatgat 82920
ttgtctgtca ttttattgtg taccattagt gtgtatgcat gtatgtatgt gccaggtagt 82980

```
taataggctg actgtgtctc ttagctccac tctgctgcct gggcctttgc catagtgctg  83040
gagttccctc acttctcttt tctgtaaccc tattatatta ctgctgtctc tcagctgtgt  83100
ttcattcctc aagcagaaag aagatgggag gatcatatag tagttgacta gaagctgtgg  83160
agtttgagtg ctgggattat atctagttcc attacttatg aagattatat ctagttccat  83220
tacttcacct catctataaa atggtttacc aatagtacct accttacatg gttttatgag  83280
tattaaatta tgtatttcta aagacattta gaacaataca aagaatatag tgtgggctca  83340
ataagtgacg atggtgttag ttattagaag gccatcgagt gctggagaaa ataattgaat  83400
atcattgatg gaaataaagg aagttttcca cgttaaaaag cttcggtttt tggaaatgtg  83460
tgttttcagt atttctgaga ttaccaggta gaaattccag ccagatgttg gaattctgca  83520
ctggcagttg ggaataaagt catgttaaag gagataagtt ttggagttat tgtgtaaaat  83580
tggtaaagca ctggaataga ttggtttgac agaggggaaa ctctttttga gataggccta  83640
tatttaggga caagagaaga gacaaccaat aagggttgaa agaaaccttg agagagtaag  83700
tcctatgaca gaagcaggga agtttcagaa tgattgcaga aagatcagcc aggctcttcc  83760
tgttctccat cgtggtgcag gatcaaggtg aaaaggataa ccccatgcag gaattttgca  83820
tctgcaggct ccgcttcaac atctgtttag gagaaagtgg agacagactg acctgagtaa  83880
ctaaggtctt ggaacagctt acaggtcaga accaggtgtt ttccaaagct agatatactg  83940
ttagcgcctt tggcaacaga agaaatgaaa agactgttgt ctgctgcaca gttcgagggg  84000
ccaaggcaga cgaaatcctg gagaatgatc taaaggtgca ggagtgtgag ttaagaaaaa  84060
ataacttctc agatactgga aactttggtt ttgggaccca ggaacacatt gatctgggta  84120
tcagatatga cccaagcatt gatgtctaca gcctggactt ctatgtggtg ctggaaaagc  84180
caggtttcat cattgcaggt aagaagtgcg ggacaggctt cattggtgcc aaatagaatc  84240
agcaaagagg aggccatgcg ctggttccag cagaagtatg atgggatcat ccttcctggc  84300
aaataaattc tcatttctac ccaaaagggt aataaaaagt tttcagtgaa atgtttaaaa  84360
aaaaaataaa aaaaagatca gccagcagcc aggatgggat tgtgaaaaca gcaggaaatt  84420
agttgttgac aaagcattaa tgaccattaa gaaatcagcc tcggctgggc atggtggctc  84480
atccctgtaa tcgtaacact ttgggaggcc aaggcagatt tcttgagtcc aggagttgag  84540
accagcctag gcaacatggc aaaaccctcg ttcctcctta ataaataaat aaatgaataa  84600
ataaacaagc aagcaagcag ggcttggtgt taggcgcctg tactcctagc tactcgggag  84660
gctgaggggg ttgaacctgg gaggcaaagg ttgcagtgag ccaagattgc actactgcac  84720
tccagcctgg gtgacagagt gagaccatgg caccccccctc cccttcaaaa agaaatcagc  84780
ctcataatca atttctctgg attaaggagt aagagcgtct caagatttgc tgtttataga  84840
gagggaggct aatagtttga gagagataca gaatctaggg agagtgtggg tttttggtct  84900
ttcagttgtt tgccagcctt ggataaagaa tgaagattac ttgagcatat tatttagaga  84960
caagtggaga gaataaaggc acatgccaga taggagataa ttaataaagc acttgtccaa  85020
aatagaaact tgttgaacag gaagagacgt caagtataag gagattttaa gatgggagaa  85080
gggaattttg agtgtttgta ttggatgacc tcagggttcc cagtaaagca ggagctgaat  85140
tcatcgaagg tgatgtgttg gtcaggatca agagagaggt tgggagaaca aagtgctaaa  85200
atcgttgtgg tcaagagttt aaaaagtgta taccagaaga gttattgagt gataggggtt  85260
tgaaataggc aaagctgtag gaaagggggc tggaaggaat attaggagga acactaaata  85320
tacttctgag gtctacctcc tggtctgtga acataaagga gctgaaagag taatggctga  85380
```

```
agttctttag tttagctaaa gtttttagc taaagctaga attgttgaaa gttgtatttg  85440
aggaaaaaaa gttaaggata cagttgaccg ttcgataatg tagcccactg ttgaccagaa  85500
gccctaccca caacataaac aggcaataac acatattttg tatgtgtatt atatagtata  85560
ttcttaacaa taaagtaaac tagagaaaag aacatgtatc aagaaaatca taaggaagag  85620
aaaacacatt tacagtactg tactgtattt attggtacca tacatttatg ttgctgttta  85680
caagatgaag catctgtctg aaatggccag cagctacagc tgtacctatc tactgtacat  85740
atcaagcaag tcactttatt cttataatgt ctatgacttc tttctttgaa agcgcttcca  85800
tcatcactgt tggcacttca tatgggtctc atggtgttaa ggtttacggc attgcactag  85860
acacaatgaa aactacacaa gagggccggg cacggtggct cacgcctgta atcccagcac  85920
tttgggaggc cgaggcgggc ggatcatgag gtcaggagat tgagaccatc ctggctaaca  85980
cagtgaaacc ctgtctctat taaaaataaa aaaattagcc aggcatggtg gcacgtgcct  86040
gtaatcccag ctaatcggga ggctgaggca ggagaatcgc tttttcccag aaggcgtagg  86100
ttgcagtgag ccgagatcgt gccactgcac tccagcctgg atgatagagg gagactctgt  86160
cgcaaaaaaa aagaaaagaa aaagaaaaga aaagaaaaac acacaagagc cgtgagagag  86220
atagcttttg attgcaatac acaatttact ggagagatga gctgatcata cagagatgat  86280
tagtgtcaca cagtgtttta aacagattct tgcaaccctg gagttcactg cagtagcaac  86340
agaagttagc tatgagattt taacagtagt atagtatgta ctacagttaa tattaggtag  86400
ctatgattta atgctgcatc tttgcatttg tttacattta tcttgactac aagtggtatt  86460
atgtctggtc ttaaggtttg tgtgcatatg ttttgatgaa ttttaacttt ttataatagg  86520
tttgtgtata ttttatggca gtaaatgata aaacagacta atctacatat attttatgta  86580
gtcatgacat aaacctaact ttttcttaac tttttgatat ttctagtcta tgtgtttcat  86640
ctgcaggttt tttcaaattg ttgaaatctc tgaaaaattt tattgaaaaa aaatccatat  86700
atgtaagtgg acccacacat ttcaaacctg tgttcaaggg tcagctgtgt aaataatttt  86760
cctcaaaatt aaagtggaaa aggagagtta ctactagtag aaagtagaac tgtacccttg  86820
ggcaggggtg tgtgtgtgta gttaaagatc aatttaactt aaaaggtctt ggttagagaa  86880
taaaaactgg cccttattag ctttaattta catgaaaaat gaaaaatttt aggccaggca  86940
cagtggctca ggcctgtaat cccttaactt tgggagacca aggggagtgg atcacttgag  87000
gtcaggagtt caagacagcc tggccaacat gctgactcac ccttccctac tgaaaataca  87060
aaagttagcc aggcgcagtg gccatcccta cagtgctagc tactcgggag gctgaggcag  87120
gagaattgct tgaacccggg aggcaaggtt gcggtgagct gagatcgcac cactgcactc  87180
cagactgggt gacagagcga gactccatct caaaaaaaaa aaaaaaaaaa aaagatttga  87240
aaacagagta ttttttaatc tgcaagagct ttacagcctt ttattcatat gtataagctt  87300
ttaaagatga ctaaaatttt agtgtggact ttccactcat tggaaatcct atattgcagg  87360
tgttaattca attttagtga gtgtgcatca tggctcagag agataggact agaatgagga  87420
ggtcacattg gagactctga aacagataca tgtgagcctc ccaacttttt aatatttgtt  87480
aatctagaag tgttgaattt tgggtgctga caaggcagca ggtagataag aattgcaaag  87540
ttaagaaaat agactgtaat attgatggta aactaattga ttaaatttta aaatgtactt  87600
ttccatgttt ttctttgaat tgtcagtaat tttgtttcaa ctggtattca tacatagatt  87660
attcacccaa tgttgacaac tagtagattt atatattttt tatgttgcct atcctttttt  87720
```

```
gggtaaggat taacagaatg tataatcacc tacattatag gtacactact aatcacttgc  87780
tacttgaaaa aacctaaagc tttgaaatct ttttattatt gcacacaaac ttatgccaaa  87840
aatggagata aagagaaaaa tgtcatccac taaaccccaa caaataatgt tgacaatgtg  87900
gtctactcgt agactcgcat tgacttaatt tttttaaatc ttattgcata ttttgactag  87960
ataataaatg catatggtta aaaaattcac atggttcaaa aaagtacacc tcccactcat  88020
cttccatgtg atatttcctt tctgcttagc aattctgtat ttatcttgct aaacatgaat  88080
gacagttgtt tgctgaaatt acattaaatg tgacgtaata aaatcattgt aagtttacat  88140
tttttaactt taataatttt taatgtttta atgaagagta tgaagagtag tagtactgct  88200
cttcaaagta ctactacttt accttacctt ttactgtttt gttaagaaaa ttaggccggg  88260
cgcagtggct cacgcctgta atcccagcac tttgggaggc cgagacgggc ggatcacgag  88320
gtcaggagat cgagaccatc ctggctaaca cggtgaaacc ccgtctctac taaaaataca  88380
aaaattagcc gggcatggtg gtgcgcgcct gtagtcccag ctacacggga ggctgaggca  88440
ggagaatggc gtgaacccgg gaggcagagc ttgcagtgag ccgagatcgc accactgcac  88500
tccagcctgg gcgacagagc gaaactccgt ctcaaaaaaa aaaaaaaaaa aaagaaaaaa  88560
gaaaattata tagaaataaa attccagcta ttccaaaact gcaccttgaa tacaggtaca  88620
gaattgctaa aaccgtgtac cattttgtag ttttagcatg cttttgtgta actgcatctg  88680
gtgtttgatc ctcatgagag ccctgttaag gaagggtaca tattattgtc ctcattttcc  88740
ttcgaaaaca catcagagtt tgtattttga ctgtcagcat tcaaatacaa gtcttttatt  88800
tataaaattt tggtctttat actgtggcta aaaatcttaa atcacttgtc atgatttgaa  88860
atggtttata ccgatttttt ttgacattta tacacacata cacatatttt taaattgtct  88920
ataataaaat catgctcatc tttgaaaaaa tattaggagt actacagtgg atacctacat  88980
acttgctatt cagcatacct ggttttttgt ttgtttttg agacagtctt ctctgtggtc  89040
caggttggag tgcagtggca cgatctcagc tcattgcaac ctccgtctcc caggctcaag  89100
tgattgtcct gcctcagcct cccaagtagc tgggactgca ggtacacatc accacgccca  89160
gctaattttt tgtatttttg gtagagacgg ggtttcacca tgttggccag gctggtctcc  89220
aactcctgac ctcaagtgat cagcccacct cggcctccca gagtgctggg attacaggtt  89280
gtgagccact gcacctggcc tgtttttaaa ttcacataaa tatgttttat atttttcatt  89340
agggagaaga aggttgtgtc tacaattttt aagacattgg ggagatttag atgccagtag  89400
taacttaaaa gagaaataat tgcaaattct ttttcctctt gagtatactt tcatttaagg  89460
tacagtgttc tgtaagttac ttttaccgtt aaacttctta atgttgctta ttgtttgtct  89520
tacattttta ggttggattt ttcttaagtc acatgtctaa taaaaaaaac ccttaaatac  89580
ctcatttatt cgtcttcgtt agtgaatgca ttgttgtaca tattagattt ttctctttag  89640
ataactcagc ttcccctatt aagtgccaca tgtattacaa aattttattt atgttttatt  89700
gtttaataaa ctcttgagaa ctagatacat tttaatcatt tgtaatactt acattttcta  89760
aaacacttca tttttccctg gtttcttcaa caaagagatg catgtagtac aaggatagct  89820
ttacctgtgt tagaagattg tttcacacat ttacatcaac tgcatagtcc tgtttttgtt  89880
gggccctaat gccagcatca ctttttgcta ctgctgtttc tgccttaaag gcaatatgcc  89940
tctgtctagt ttgctgattc tgatactctt tcccctggaa agtaggtaat caagtttgtg  90000
aggagctgtg tgtttaagga gtccataaat ccttgtgggg agccctaggt gtatagagca  90060
tagctgtagg gcagaggcct ttgacactta ttctggatat gcagtggcct ttgcctatgg  90120
```

```
ggttcatggg tcagagcgct gttgtgacct ttgaataaat gggttgttat gataattgtt  90180
ttaagggagg agagttattc tgatatcctt tgtattgata ttgctcttat ttattattga  90240
gctggattta agtattaatc atttaaggtc aaatttctaa tgtatatatg ttcttaaatg  90300
gctacgaccc agttaccata gcaatttagt gaaataacta taatggaaca tttttttca  90360
atttggcttc tcttttttt ctgtccacca gggagtaact attcccagtc agaggcgcta  90420
tgtgtattat tatagctacc tgttaaagaa tcatctggat tatagaccag tggcactgtt  90480
gtttcacaag atgatgtttg aaactattcc aatgttcagt ggcggaactt gcagtaagtg  90540
cttgaaattc tcatccttcc atgtattgga acagttttct taaccatatc tagaagttta  90600
cataaaaatt tagaaagaaa tttaccacat ttgaaattta tgcaggagac tatatttctg  90660
aagcatttga acaaattaat tagctttgtt gttcaactca ttgggctaaa gaagccaaaa  90720
gcaatgggtt ttaatgtagt cgaagccaaa ttatatttat gaaagaaata ttctgtgtta  90780
taaccaccaa atacagccca attctgacta gatgatggaa gaacctgtcc catcagaggt  90840
ccagcatgag gtccagcaga ggtccaccag aggagttcag caatttgctg ctcttagggc  90900
agggatcaat tccttaatat cttaggaaga ctaggtattg acagtaatgg tgacaaagca  90960
atgaaaagga aaggaagaag tgataagacg tggcagcaag ctgaagtatg atgagtaaag  91020
aataggaatc aaagtatgtg gagtgttaga gaaaacctgg atttagatcc agattctagt  91080
cctatctctg tcattaatct attgcgtaac cctgagcata tcatctacct ctctttgagt  91140
ttgcttgtca ataaaatgaa gagactttga aatctgagac ttcctggata agtactaaat  91200
acagattatg tcactgatgt ctgcctctat ttatttctcc cttttaccct aatctctata  91260
agtctacctc agtcatcctg atcctattct acttctctga tgttgttgtc agataggtgt  91320
gatcatcctc atcagatctt ttctgtattc ttagagacag ataactttat caaagaccac  91380
agatttatta gtatagcatg ttaaagtctt ctaaagagtc tcattgatgc tcttttcatc  91440
tcagtacaat ttttaaaact gctgaatgca aggtactgag ctgttggaag tgactgacag  91500
atgaatgtaa cagattcata gagaaggaaa aaggaagaaa aactcatgct cttcctatag  91560
tattgatatc agtgtaagag ccaagagaaa ggtataaagt atcatgcaga tattaaggga  91620
aagaaaacat tcactttagt aatctttcct cattttctag tttcctctta tgtactatga  91680
tttaatactg tagtaaagtt ttaataaaat atgagctata tgtaattaag tgggaggttg  91740
tggggctagg cacgaggctc acacgtgtaa ccccagcact ttgggaggct gaggcaggcg  91800
gatcgcttga tctcaggagt tcgagaccag cctggacaac aaggtgaaac cccatctcta  91860
ctaaaaacac aaaaattagc tgggcatagt ggcacacacc tgtagtccca gcttcttggg  91920
aggctgaggc aggagaatcg cttgaatcca ggaggcagag gttgcagtta gccgagatca  91980
tgccactgca ctgcagcctg gacatcggag caagactttg tcttagaaat aaataaataa  92040
atataaaata aaataaatgg gaagttgtgt atataaatta taaatgctac attcagaaaa  92100
gcttttgaag gttgtcagac agtttcttaa aggaagttca ccagttcttt attgaacatt  92160
gaagaaaaca tacagtttag actggcatta aaactgaaag aagtggccag acgcagtggt  92220
agacgcagtg gttcacgcct gtaatcccag cactttggga ggtcaaggtg gatggatcac  92280
ctgaggtcag gagtttgaga tcaggctggc cgacatggtg aaaccctgtc tctactaaaa  92340
atacaaaaat tagccaggca tggtgatgcg tgcctgtagt cccagctact tgggaggctg  92400
aggcaggaga attgcttgaa gccgaaggtg gaggttgcag tgagccgaga ttgcgtcatt  92460
```

```
gcactccagc cagggcggta agagtgaggc tccgtcttaa aaaaaaaata agtaaataaa  92520
ttaaaaacta ctgaaagaag tattacaggc aatgggaaat agcttgagtg gaagtgcagc  92580
agaaggaaaa agctggacaa gaatgtagtg tcagagaata ggtatggaac gtgtgagtga  92640
ctgttagagg atcttgaatg gggataacag acttgatttc ataaatactg agatgtcatg  92700
ataatacttg aggactaaac catgttttaa ggacagttgt atgcaaagtt gtaatcgcaa  92760
gaggaaaaaa tagtggaaaa gaaaccagta ataaaacttg ccttaatgca ggtatgctaa  92820
gacaatcaaa tgggatttca ttaatttttt atttgccatt tatagccaaa gattttgtaa  92880
aagttttgag cccagtcagg tgaaatagtc tcagaaagaa agaaaagtga atctgagact  92940
tggagacatt aatgttgata ttttggtttt aaacgtgttt taaatccggt aaaagtgagc  93000
ttctcacatg acaatattca gtgggtactt gggagtatgg gttcgaatct aggtaggaga  93060
tatatcgata ttttgggcat catcaggaaa gggagagtag ttaagccttt catataaata  93120
atggtgtggc gtttgggcat gggaagtctt ggaggaaagg aagaaaagga gagggtgagg  93180
actgagataa gaatggcaac ttgggtttag gaagaagaag aggaatcaat gtagagaaca  93240
gatagtgctg aaaaatacag catcttctgt agggattggc agctttttct tgatttttgt  93300
cttaatattt ctaagagatg gaaaaagcta ctatattcta gacatttaac agggttaaaa  93360
atgttactaa aagatgatca atgtggtttt cattcaagac tataacaata tgtatatatc  93420
caaggaaatt taattctgac ttaaaaaaat tgttttgctt gtatagattt agggacacaa  93480
gtgtaatttt gttacatgca tagagtgtat agtttcaagt cagggctttt aggttgtcca  93540
tcatctgaat aatatacatt gtacccatta agtaatttct catcttctac tcaccgtttc  93600
aagtctccac tatttatcat tccattcttt acattctgat tttcatttac taggtgtatt  93660
agtctgtttt tgcattgctt taaagaaata cctgagactg agtattaaac aggtttaacc  93720
tgttttcttt atgaattctt ctttaattgg ctcatggttc tgcacgctgt acagaaagca  93780
tagcagcatc tgcttctggg gaggcctcag gaagcctcca atcatggctg aaggcaaaag  93840
gggagcatgg tgagaatggg agcaagaaag agaaggagtg gtggggagaa ggtgccaccc  93900
acttttaaat gccagctcac ttaccaccaa gaggatggcc caagccattc atgtgggatc  93960
tgcccccatg attcaagctt cttccaccag gccccacctc tagcactggg gattacaatt  94020
caacctgaga tttgggaggg aaagatatcc aaactatatc actaggtctg gatcttgtta  94080
tttatttttt ggaacatagt catatatatc caaggatata tattgtagaa gtccacagaa  94140
ccatactaat attggacttc tgcttagtta ggtcttatct atctgaaaca tgatattcat  94200
attgcagaga agattatttt ctttagtgat tgaggaaatc tttactactt atacattttt  94260
aatataatac tataatattt gaagatgcac attttagatg tagtttaatt gaaacctgga  94320
aatactatta atttgctttt taaagtccta aaatcaggat tatcagattc tgaattaatg  94380
gagtttaaat caaaaagatt acaaggcagt tttcagttt tattctggtt aattttatca  94440
cagctttgga atcctacttt gtttatttgc ttcttgaagt tagatttccc agtgaaattt  94500
cagtatcaca taaagtctta tgaaatggct cattgcactt tgaactttga gtcaaggaag  94560
tgaaatttat tgatagattg ttggtgtaat atttatcctg tttgtggtag ctttttttgaa  94620
taataagtgt cttagaagac catgttggag tagcctgcat gcttttatca aacatattaa  94680
ttatgtgatg gctgatactg ctttagatat tacatagaaa tagtagtagg tgtttactaa  94740
actggaaatt tcatttaact tggtttagct ttgccttgtt ctcagtcaca ttgataaaaa  94800
tgtaagactt ttgtttatct tttagaataa tgacaccttt tggtgctgag aatttttttgt  94860
```

```
tttatatata tatatatata tacgtaatat aaatacaaaa tatatttaaa tatgtataat  94920
atttctcata cactttatgt aactttgtgt tcctgtttct ctattatctt ggcatgtttt  94980
cttcaaatgg cacttcttaa cctcctaagg ttaataaatt tctttgtaat ggacttttgt  95040
tttctaattc ctcagcgtat gacaaatgaa ttatactttg tcaaattatt taggtaactt  95100
tcagtttttg aagtcctggg atcataacat tcatcagtct ttaatttctg tcattaaggt  95160
cattagctat aaatgaattt atgagtagat ttaaaaaata aaacatacaa tccttccctt  95220
aacacacttt cccaccattt ggttcaactg ctagtgtaaa agcatgatga attttgagaa  95280
gttatatttt accagttact ttattttta ccagttattt aaaacagaca tgagccaaag  95340
ccagaatact tgttaatgaa aatgaggtgt tttggaggaa aggaaggttg tgctgcagtt  95400
tttacttgaa atctgttaca tttctttaca gaaatttcaa atctcttgtt tcctgttatg  95460
atggtggcat tatatacctt taaaatgtga gctataggaa aatgaatgat ggttaatttt  95520
ttaataaata tttagacttg tgtttttgaa atttttata acattgttat aggttttatc  95580
ctctttctct tgtgaacatg tagtgatttg tattttgtga tctttgccgc atgctagaga  95640
cttaagaata ctatagcaaa tatctgtctt ctttacattt aaaaattttt cgtgactact  95700
ccctgttgat atctgtctta aaagttactt ttgatgtagt tcacaaatgt accagataat  95760
tatttcatcg tttttaatgc ttaaagtttt tatttgtatt aggattttta gtatgatttt  95820
aatgttaaag ttttgaagtt actctgccac tagaagtcta attttgggac ttactattca  95880
tgaaatagga attgactttt atataagtaa taggacctta ttttgaaggt tcaaactgga  95940
gaaaatctta cattgtttat atttttattt catttatttc agttgatttg cttgagatca  96000
agattgcaga tacagaatcc atatttcgtg tatattgctg atattaatca ttaaaatcgt  96060
ttttgacagt ttgacagtta aaggcatttc ctgtgaaata atactggtat gtatttaacc  96120
atgcagatcc tcagtttgtg gtctgccagc taaaggtgaa gatatattcc tccaattcag  96180
gacccacacg acgggaagac aagttcatgt actttgagtt ccctcagccg ttacctgtgt  96240
gtggtgatat caaagtagag ttcttccaca aacagaacaa gatgctaaaa aaggtttgta  96300
ctttactttc attgggagaa atatccaaaa taaggacaga ttaaaagcta tattttattt  96360
tatgacatgt aaggaactat aatttgtttt ctattagatc tgcaggtgtt ttgcttactc  96420
tggcattggt gagacattat aagggtaaat aatcctgttt gaaggaaaag gccttatggc  96480
attgtaacat gagaggaatt tttcttaaca aggatggtta actgagaaga aattagcatg  96540
ggaccaatat tttaaaaatt ttggtctata ggtagaaatg agatctgttc tgtggtctta  96600
tgtagtgaca caaaccactt tttctccatt ttggcttatg tttctttttc tttccttttt  96660
tttttttttc ctttttgtta gagacagggt cttgttctat tgcccaggct gagtagctaa  96720
gactacaagc atgtgccacc acacccagct aatttttttt atttttattt ttgtagggac  96780
agggtctcac tatgttgccc aggctggtct caaactcctg ggcacaagca gtcctcacgc  96840
tttggcatcc caaagagttg gaattacagg tgtgcgccat catgcctggc cttaacgttt  96900
cttaagactt gattattttc tatttagctt ctgtggattt actgattaat tttttaacta  96960
ggagagaaat cagtatgaag aggaagtaat aaagaatgaa aacatggtat ttaaatgtgc  97020
aggtttagaa agttaatgaa gtttgaattt gattgatctg tatttagaga aggcaacgtc  97080
ttattatttt aaaaccaact atccgccctg tgcggtggct cacgcctgta attccagcac  97140
tttgggaggc tgaggtgggc agatcagctg aggtcaggag ttcgagacca gcctggccaa  97200
```

```
catggttaaa ccccatctct actaaaaata caaaaaaatt agccgggtgt ggtggcaggc  97260
gcctgttttc ccagctactc aggaggcttg aggcaggata attgctgaac ccgagaggcg  97320
gaggttgcag taagccaaga atgcaccatt gtactccagc ctgggcaaca agagtgaaac  97380
tccatctcaa aaaaaagaa aaaaaaaca acaactatct tcatttaaaa tattaaatgt  97440
gaatatttaa agtgagacta aggtgcaaca tttttagata gtaatgaaga aaaggactaa  97500
ctttgtagtg ttgctgcctt gttaaacata ctagatagca tattgccaat ctttaaacat  97560
tctcaatgat aggatttatt tactttttct gatttttagc ttttcttttg aaagaaaata  97620
agaggaagtt tcatttactg caaaatttta aatgctgctt tgatgtatca gtagagatat  97680
aattttcctt tatccagaat ccaagtagct ggaaaaaaaa atcaaaatat gctgaacttt  97740
ttttttttta gccagaaacc catttcctat cgtctgtaca aataaaagtt aaatatatct  97800
caataactta gaaaaattat tttttgataa tccaggaagt attagcaact gttttaaaat  97860
taagataact agtaagtttt atttagcttt caaaaatagg catctacatc atcatctctg  97920
catacctttta ggaatttcct aattcttatt tcccttcatc tgtactttaa cacatgcaaa  97980
attgaaggtt agattaaata tttatgattt atttgtttat ccttgactac ataaatttcc  98040
attttattga ttttccctgc cttatttaag aatatgctat gattaaaaca caaaaaaattt  98100
tagtataacc catatatata tagaattcac ctttttgtta tttaaatatt attggcttat  98160
tttcttctaa gtaaaataca attactggct aaaataattg aaataagcaa aaaaaaaatt  98220
ttaaagacct tgtatacaag attactttgc caggtactgt taaaagatgc aatgacattt  98280
aagacgtaac atccttaagg atcttatttt ctgggggata aaaaacttta agataaatta  98340
gaataaaaga tttaaatggc atttaaggt accaggtacc agataagatg tcacaaggct  98400
gtatatcatt aattgccaaa tgatttatac aggccagatt tctttgttgg tcaatagagg  98460
tttaaagtga tgaacttctg ttgtgttttt ttattaagaa ggtattatct tattagtaag  98520
aagtgatttt ttttaagaac aagcatttta taacatcaaa agaaatcagt agtactcttt  98580
cctacccccct catatttatt ctgaaagtat tcaagcatta tattgtcatg taagaaactg  98640
gagcttctca tgtttgtatt gctgtagaag taaacatgta tttgccatgc gtcatcaggg  98700
aagttgcact caccgtccaa gaacttttgt taaagtaaat cttggaatag gtagctcatt  98760
tgaaatgtag aaaaaattaa atccatatct gaattttgtt tatatgtatg tacacgtaaa  98820
ctaaaaacgt atttaaagct agtattagat gagaaaagag gttttttttac ttaaaatttt  98880
aaggcaaaag tagtttatct tagatcttgt gagattgtat ttttggttta aaatttgaga  98940
atttgagtga agaaaaatca tgtgaatgaa aatgcaacag ataactcaga ttgccttata  99000
atagtctttg tgtttacctt tattcagaat atcaaatgat agtttatttt gttgactttt  99060
tgcaaatgtt taacataggt gacagatttt ctttttaaa aaaataaaac atcattaatt  99120
aaatatgtca tttcatttct ttttcttttc tttttttttt tttttaggac aaaatgtttc  99180
acttttgggt aaatacattc ttcataccag gaccagagga aacctcagaa aaagtagaaa  99240
atggaagtct atgtgatcaa gaaatcgata gcatttgcag tatagagcgt gcagataatg  99300
acaaggaata tctagtactt actttaacaa aaaatgatct tgacaaagca aataaagaca  99360
aagccaaccg atacttttct ccaaatttta aggtcagtta aattaaacat tttgtggggg  99420
ttgttgactt gtatgtatgt gatgtgtgtt taattctagg agtacagctg atgaagaact  99480
tgcttgacaa gtttttaact tatgtattat ttcgaagcag tgtttacgta gcagtaacat  99540
gaaagtttct aataaaatac ccaatgtaca cagcgtcaaa aaagctgcat ttttcctttt  99600
```

```
cctaattctt cgttgtttgc tgaaatctgg ggcaaaggtg cgggaggggg ctaaatgact  99660
gggatatgaa gtaggaatgg gagaggaaag aaatagatgg gaactcagtc atttgggaat  99720
gattcatatg gaatgttttt actgcttcca ctcctgtctg ccttccaatt tattctcaat  99780
ccctcagagt gatcttaaaa atagacttga ttgtgtcact tctgtttaca ctttataagg  99840
accttgtgtt ttttttttta ccatgaccta caaggcccag cataatttag cacagggcta  99900
cctcctacat cagcactagt caccttctct ccttgtttct tgagattcag tcatactggt  99960
ctttcttcag ttcttcaaaa tgctaagctt ctgcctcttc tagtctttcc agttattttc 100020
cttctccctg taccttttca tctcagcctt ttcccctgac cttccatagc tatcttcata 100080
tttccagcct tagcttcaat ctcatattct ctgaagtcct ttgattgtcc tcccgttatt 100140
cttttttaa aaatcctatt tccttatatt gtatcttaga attatttggt ttgtttcatt 100200
tttgcctatg tgtgatatat gtatttctac ataggtatat atatctactt atagacaaga 100260
attcttcaga ttaaaaaaat ctgatttgta aacattccca agtggttgtt taccattttt 100320
ttcttccccc ttcctatttc ttattctacc tgattttccc ctgttcattc accacactcg 100380
tttctttctc tttttactc tctcttaatt tttcattcaa tttttataac atgtaataaa 100440
tctaactgta gcgtctgagt attaagaata ttgctagtaa tacttcacct gtaatcccag 100500
cactttggga ggctaaggca ggcggatcac ttgaggccca ggagtttaag accagccggc 100560
caatatggcg aaaccctatc tgcactacaa atacaaaaat tagctgggca tggtgtcgca 100620
cacctgtaat cccagctact tgggaggctg aggcacaaga attgcttgag cctgtgagat 100680
ggaggttgca gtgagccgag atcacaccag tgcacgtgca cttcagcctg ggcaacagag 100740
caagactctg tcttaaaaaa aaaaaaaaaa aaaaaatata tacacacaca cacacacaca 100800
cacacacaca cacacactat tactaccaat atacatacat atatgtatgt atgtatgtat 100860
gtatattggt agtaatagta atacttgggc ccctgcacgt tttaagtgaa aatagatcta 100920
atattaaatg tctttagccc ttaaattttt tttaagtgtt cagaagtttc cctttaaaaa 100980
aatttttaat atataataat tgtacatatt tatgggatac agagtgatat tttcatgtat 101040
gcagtgtgtg atgatcaaat caggataatt agcatatgga tcacctcaaa catttgtcat 101100
ttctttgtgt taggaacatt caaaattctg tcttctagct atttgaaaat atacagtaaa 101160
ttattgttga ctagttacag ttctatagaa cactataatt tattcctcct gtgtgtaatt 101220
ttttatcttt taaccaacat ctccctatcc tcccctccca ctccctttcc cggcctctaa 101280
taaccacact cttatgagct caacttttt agcttccata tatgagtgag aacatacggt 101340
atttatcttt ctgtacctga cttattttac ttaacatcat gtcctccggg ctagacattc 101400
tctttagaat ccacaggttt cctttctttt ctctaaatct gcattttgct cagccattaa 101460
cttttaaaat gtctttttcc ctttagtttt attgttttct attttaatat tgcaagatgt 101520
tttatatttg tgattacaaa taaaaactcc attattagta aacaaataca atgtcatata 101580
gtagtaagtg ctataaaaaa tagacaggat agaaagtaat cttggtttgt atgtttttg 101640
tttttagca aagatgatta gagaaggccc aaccaagcag ataacattta agcagaggcc 101700
taaatcatat aagtgagtta tacaaatatc tgggaaaaga gttaagagta cagatgcaaa 101760
agcccttaga caagagaatg agcttggtat atctgaagag tggataagtc attttgactg 101820
aaacagagtg gacaagaaaa ccagtccaag tgtaaagaca ctagtgtgtg ttcagcatag 101880
gaaggatgta atctgaattt tgtgtttaat attccctgtg ttcatgcttt caaaatacag 101940
```

```
atgagtgagg aaagtaggga gaaggggtaa taaaggaagc tgagagatca gttaagaggt 102000
acttgaatag tttagtaaag atgagagaag atgtttgctt cttgttgccc ctcactgctt 102060
agaatagtgg cagtgaaggg taacaagaag ctgtcagatt aacttaaaga gtttactgat 102120
gcagtggatg ttggttgtaa gagaagaatt gataatgact cttggataat aggggaggga 102180
ggggctgtca atataatata atgaagaagg gatttgaagt catttctgat ttaaatctca 102240
catccactac ctacttttaa tagatatgta gcctttaaca agttccctaa cctttctggg 102300
ccttagctac ctccccttgg aaatggaaat acctaacatg taaggttgtt ttgacagtta 102360
ttttcactag gcatgtaaag gcacttgact ctctgttata gaccactgta ttatgttaat 102420
gtccctctcc ttcctccctt taggtaaagt ttttagggct aataaatccc aaatatcaat 102480
gttgatcagt agtttgtgtt tgtgtagtgt tgtttatatc aaaaactaca ttgaagccgg 102540
gcacagtggt tcacgcctaa aatcgcaaca ctttgggagg ccaaggtggg cctcccacct 102600
tgaactaagg agtttgagac cagcctgggc aacatggtga aatcccatct ctacaaaaaa 102660
tataaaagct agctgggtgt ggtggcatgc acctgtagtc ctagctactt gggaggctga 102720
ggttgatcct gggagtttga gcctgcagtg agctgtgaag atgccactgc actctagtct 102780
gggtgacaga gcaagaccct gtctcaaaaa cacacacaca cacacacaca cacacaaaga 102840
aatacattga tttttcacat aggtagtaag agaaacattc tttttgaact cagctgtttg 102900
tgaattgaat tttgtaattc aaatgctata ttatgtaaac tattgatgac tttcaatctg 102960
catttatttt gtataattat ttagttaata tttgccactt atattcctta aaaaataaaa 103020
ttgaggttgg gcgtggtggc tcacacttgt aatcccagca ctttgggagg ctgaggcagg 103080
cagattgcct gagctcagga gtttgagatc agcctgggca acatcatgaa ccccatttct 103140
actaaaatac aaaaaattat ctgggcatgg tggtgtacac ctgtagccct agctgtttgg 103200
gaggctaagg cacgagaatt gcttgaaccc gggaggcaga ggttgcagtg agccaagatc 103260
atgccactgc actccagctt ggcaacagag caagactctt gtctccagaa ataaaaataa 103320
ataaattgta ttaacatcct gatagtttat ctgtttagta cctagcaaga aagaaaatgt 103380
tgaacatctt aagaagaggg tcatttaaaa ggcctcttaa agatcatgtt tgttacagtg 103440
cttaaaaatt aatatgttca tctgcaaaat ggaataaaaa atctgttaaa aatatatttc 103500
actaaatagt ttaagatgag tcatatttgt gggttttcat tttaaatttt ctttctctag 103560
gtgaagctgt acttcacaaa aacagtagag gagccgtcaa atccagaggc tagcagttca 103620
acttctgtaa caccagatgt tagtgacaat gaacctgatc attatagata ttctgacacc 103680
actgactctg atccagagaa tgaacctttt gatgaagatc agcatacaca aattacaaaa 103740
gtctgaattt ttttttatca agagggataa aacaccatga aaataaactt gaataaactg 103800
aaaatggacc tttttttttt taatggcaat aggacattgt gtcagattac cagttatagg 103860
aacaattctc ttttcctgac caatcttgtt ttaccctata catccacagg gttttgacac 103920
ttgttgtcca gttgaaaaaa ggttgtgtag ctgtgtcatg tatatacctt tttgtgtcaa 103980
aaggacattt aaaattcaat taggattaat aaagatggca ctttcccgtt ttattccagt 104040
tttataaaaa gtggagacag actgatgtgt atacgtagga attttttcct tttgtgttct 104100
gtcaccaact gaagtggcta aagagctttg tgatatactg gttcacatcc taccccttg 104160
cacttgtggc aacagataag tttgcagttg gctaagagag gtttccgaag ggttttgcta 104220
cattctaatg catgtattcg ggttagggga atggagggaa tgctcagaaa ggaaataatt 104280
ttatgctgga ctctggacca tataccatct ccagctattt acacacacct ttctttagca 104340
```

```
tgctacagtt attaatctgg acattcgagg aattggccgc tgtcactgct tgttgtttgc 104400
gcattttttt ttaaagcata ttggtgctag aaaaggcagc taaaggaagt gaatctgtat 104460
tggggtacag gaatgaacct tctgcaacat cttaagatcc acaaatgaag ggatataaaa 104520
ataatgtcat aggtaagaaa cacagcaaca atgacttaac catataaatg tggaggctat 104580
caacaaagaa tgggcttgaa acattataaa aattgacaat gatttattaa atatgttttc 104640
tcaattgtaa cgacttctcc atctcctgtg taatcaaggc cagtgctaaa attcagatgc 104700
tgttagtacc tacatcagtc aacaacttac acttatttta ctagttttca atcataatac 104760
ctgctgtgga tgcttcatgt gctgcctgca agcttctttt ttctcattaa atataaaata 104820
ttttgtaatg ctgcacagaa attttcaatt tgagattcta cagtaagcgt tttttttctt 104880
tgaagattta tgatgcactt attcaatagc tgtcagccgt tccacccttt tgaccttaca 104940
cattctatta caatgaattt tgcagttttg cacatttttt aaatgtcatt aactgttagg 105000
gaattttact tgaatactga atacatataa tgtttatatt aaaaaggaca tttgtgttaa 105060
aaaggaaatt agagttgcag taaactttca atgctgcaca caaaaaaaag acatttgatt 105120
tttcagtaga aattgtccta catgtgcttt attgatttgc tattgaaaga atagggtttt 105180
ttttttttt ttttttttt tttttaaatg tgcagtgttg aatcatttct tcatagtgct 105240
cccccgagtt gggactaggg cttcaatttc acttcttaaa aaaaatcatc atatatttga 105300
tatgcccaga ctgcatacga ttttaagcgg agtacaacta ctattgtaaa gctaatgtga 105360
agatattatt aaaaaggttt ttttttccag aaatttggtg tcttcaaatt ataccttcac 105420
cttgacattt gaatatccag ccattttgtt tcttaatggt ataaaattcc attttcaata 105480
acttattggt gctgaaattg ttcactagct gtggtctgac ctagttaatt tacaaataca 105540
gattgaatag gacctactag agcagcattt atagagtttg atggcaaata gattaggcag 105600
aacttcatct aaaatattct tagtaaataa tgttgacacg ttttccatac cttgtcagtt 105660
tcattcaaca atttttaaat ttttaacaaa gctcttagga tttacacatt tatatttaaa 105720
cattgatata tagagtattg attgattgct cataagttaa attggtaaag ttagagacaa 105780
ctattctaac acctcaccat tgaaatttat atgccacctt gtctttcata aaagctgaaa 105840
attgttacct aaaatgaaaa tcaacttcat gttttgaaga tagttataaa tattgttctt 105900
tgttacaatt tcgggcaccg catattaaaa cgtaacttta ttgttccaat atgtaacatg 105960
gagggccagg tcataaataa tgacattata atgggctttt gcactgttat tatttttcct 106020
ttggaatgtg aaggtctgaa tgagggtttt gattttgaat gtttcaatgt ttttgagaag 106080
ccttgcttac attttatggt gtagtcattg gaaatggaaa aatggcatta tatatattat 106140
atatataaat atatattata catactctcc ttactttatt tcagttacca tccccataga 106200
atttgacaag aattgctatg actgaaaggt tttcgagtcc taattaaaac tttatttatg 106260
gcagtattca taattagcct gaaatgcatt ctgtaggtaa tctctgagtt tctggaatat 106320
tttcttagac tttttggatg tgcagcagct tacatgtctg aagttacttg aaggcatcac 106380
ttttaagaaa gcttacagtt gggccctgta ccatcccaag tcctttgtag ctcctcttga 106440
acatgtttgc catactttta aaagggtagt tgaataaata gcatcaccat tctttgctgt 106500
ggcacaggtt ataaacttaa gtggagttta ccggcagcat caaatgtttc agctttaaaa 106560
aataaaagta gggtacaagt ttaatgttta gttctagaaa ttttgtgcaa tatgttcata 106620
acgatggctg tggttgccac aaagtgcctc gtttaccttt aaatactgtt aatgtgtcat 106680
```

```
gcatgcagat ggaaggggtg gaactgtgca ctaaagtggg ggctttaact gtagtatttg 106740
gcagagttgc cttctacctg ccagttcaaa agttcaacct gttttcatat agaatatata 106800
tactaaaaaa tttcagtctg ttaaacagcc ttactctgat tcagcctctt cagatactct 106860
tgtgctgtgc agcagtggct ctgtgtgtaa atgctatgca ctgaggatac acaaaaatac 106920
caatatgatg tgtacaggat aatgcctcat cccaatcaga tgtccatttg ttattgtgtt 106980
tgttaacaac cctttatctc ttagtgttat aaactccact taaaactgat taaagtctca 107040
ttcttgtcat tgtgtgggtg ttttattaaa tgagagttta taattcaaat tgcttaagtc 107100
cattgaagtt ttaattaatg ggcagccaaa tgtgaataca aagttttcag ttttttttt 107160
tcctgctgtc cttcaaagcc tactgtttaa aaaaaaaaaa aaaaaaaaac atggcctgag 107220
agtagagtat ctgtctactc atgtttaatt aaggaaaaac acttattttt agggctttag 107280
tcatcacttc ataaattgta taagcacatt aaatagcgtt ctagtcctga aaaagtccaa 107340
gattcttaga aaattgtgca tatttttatt atgacagatg tttgaagata attccccaga 107400
atggatttga tactttagat ttcaattttg tggcttttgt ctattattct gtactctgcc 107460
atcagcatat ggaaagcttc atttactcat catgacttgt gccatataaa aattgatatt 107520
tcggaatagt ctaaaggact ttttgtactt gaatttaatc atgttgtttc taatattctt 107580
aaaagcttga agactaaagc atatcctttc aacaaagcat agtaaggtaa taagaaagtg 107640
tagtttgtac aagtgttaaa aaaataaagt agacaatgtt acagtgggac ttattatttc 107700
aagtttacat tttctccatg taattttta aaaagtaaat gaaaaaatgt gcaataatgt 107760
aaaatatgaa gtgtatgtgt acacacattt tatttttcgg tatcttgggt atacgtatgg 107820
ttgaaaacta tactggagtc taaaagtatt ctaatttata agaagacatt ttggtgatgt 107880
ttgaaaaata gaaatgtgct agttttgttt ttatatcatg tcctttgtac gttgtaatat 107940
gagctggctt ggttcagtaa atgccatcac catttccatt gagaatttaa aactcaccag 108000
tgtttaatat gcaggcttcc aaaggcttat gaaaaaaatc aagaccctta aatctagtta 108060
atttgctgct aacatgaaac tctttggttc ttttatttt gccagataat tagacacaca 108120
tctaaagctt agtcttaaat ggcttaagtg tagctattga ttagtgctgt tgctagttca 108180
gaaagaaatg tttgtgaatg gaaacaagaa tattcagtcc aaactgttgt aaggacagta 108240
cctgaaaacc aggaaacagg ataatggaaa aagtctttta aagatgaaat gttggagcca 108300
actttcttat agaattaatt gtatgtggct atagaaagcc taatgattgt tgcttatttt 108360
tgagagcata ttattctttt atgaccataa tcttgctgtt tttccatctt ccaaaagatc 108420
ttccttctaa tatgtatatc agaatgtggg tagccagtca gacaaattca tattggttgg 108480
tagctttaaa aagtttgtaa tgtgaagaca ggaaaggaca aaatagtttg ctttggtggt 108540
agtactctgg ttgttaagct aggtattttg agactacttc cccatcacaa caacaataaa 108600
ataatcactc ataatcctat cacctggaga catagccatc gttaatatgt tagtgactat 108660
acaatcatgt tttcttctgt atatccatgt atattcttta aaaatgaaat ttatactgta 108720
cctgatctca aagcttttta gcttagtata tctgtcatga atttgtagga tgttccattg 108780
catcagaaaa cggacagtga tttgattact ttctaatgcc acagatgcag attacatgta 108840
gttattgaga atcctttcga attcagtggc ttaatcatga atgtctaaat attgttgaca 108900
ttaggatgat acatgtaaat taaagttaca tttgtttagc atagacaagc ttaacattgt 108960
agatgtttct cttcaaaaat catcttaaac atttgcattt ggaattgtgt taaatagaat 109020
gtgtgaaaca ctgtattagt aaacttcatc acctttctac ttccttatag tttgaacttt 109080
```

tcagtttttg tagttcccaa acagttgctc aatttagagc aaattaattt aacacctgcc 109140
aaaaaaaggc tgctgttggc ttatcagttg tctttaaatt caaatgctca tgtgactttt 109200
atcacatcaa aaaatatttc attaatgatt cacctttagc tctgaaaatt accgcgttta 109260
gtaattatag tgggcttata aaaacatgca actctttttg atagttattt gagaattttg 109320
gtgaaaaata tttagctgag ggcagtatag aacttataaa ccaatatatt gatattttta 109380
aaacattttt acatataagt aaactgccat ctttgagcat aactacattt aaaaataaag 109440
ctgcatattt ttaaatcaag tgtttaacaa gaatttatat tttttatttt ttaaaattaa 109500
aaataattta tatttcctct gttgcatgag gattctcatc tgtgcttata atggttagag 109560
attttatttg tgtggaatga agtgaggctt gtagtcatgg ttctagtgtt tcagtttgcc 109620
aagtctgttt actgcagtga aattcatcaa atgtttcagt gtggttttct gtagcctatc 109680
atttactggc tattttttta tgtacacctt taggattttc tgcctactct atccagttgt 109740
ccaaatgata tcctacattt tacaaatgcc ctttcagttt ctattttctt tttccattaa 109800
attgccctca tgtcctaatg tgcagtttgt aagtgtgtgt gtgtgtgtct gtgtgtgtgt 109860
gaatttgatt ttcaagagtg ctagacttcc aatttgagag attaaataat ttaattcagg 109920
caaacatttt tcattggaat ttcacagttc attgtaatga aaatgttaat cctggatgac 109980
ctttgacata cagtaatgaa tcttggatat taatgaattt gttagtagca tcttgatgtg 110040
tgttttaatg agttattttc aaagttgtgc attaaaccaa agttggcata ctggaagtgt 110100
ttatatcaag ttccatttgg ctactgatgg acaaaaaata gaaatgcctt cctatggaga 110160
gtatttttcc tttaaaaaat taaaaaggtt aattattttg actattcggt tttaaacttt 110220
ttattcaaca aataccaagt ccctgctgta tatatgggtt tggaatacat tagtgatcaa 110280
aacacaccct ctatccctgc ccttgaagag tttacactcc agtagaggaa acagaattta 110340
cattaacaat tataaattgt gatacatgct gtggaaagtg aggtgcatgt gataatggtt 110400
atcaaacatt atgctcccca aaatttccat caccttgcag ttgaatgagg cctatgtaac 110460
tagtttattc taatgtaata cagaaagtag tgtgacactc cactttctgt aaaggcaatg 110520
aaaaaaattt accatccagt ttctctcttc ccctactgct gtgattaagg attttgcatg 110580
ttctagatgg tgcagctttg tcagcctggg tcttgagtga tactggagca gaactccctc 110640
aaattgttcc ttctgccacg ctaaacttgt tagatattag cataaataag aaataaacca 110700
tttagactga tactttggga caattttttta tcacagtgta agttatatcc tgactaaaac 110760
agtgctttgg aaagatcagg gaagggtttc ttgagctaca aaagggagtt aagaatgaag 110820
caaaatgaaa tatggcatct ttaaatgaca tgatgcaata aactctaaat tgcaagttat 110880
tcaatagtta ctgagcacca gatatgtgtc agacactgtt ctagatgctt gggatacaag 110940
tgggtgaaca gcaggacctt gccttcatgg agcttacatt ctagcaaggg aaaatagtca 111000
acatactata tgtaaggtaa tgcgtgctat agcagaaatg aaaggtaagg gagctcagga 111060
ttgctgggtg gagagatttc agtgttgaat ggtgtagtcc agaacaggcc tcactgggaa 111120
ggtaagattt gaagactgct gactaacagt ggcattggga ttttccttca ttctttcaac 111180
cagcgagatg cactcagaac cctctataca attttattct cactttatac aactctgtac 111240
attagttctg agtttttaag atgattgttg gcatatctag ggagaatttt taggaatacc 111300
acccaaaata gtcgcaatgt tctaaaacca ttttgttttc taaattggtt tggcaaactc 111360
tatacaaaca gtctgttcct tttcattctc caagttgagt tttaaattt aaattatact 111420 ctttgtgcat tttgacaata cttacctctt ttcagaagac attaaagttc tgttatggcc 111480
ttaaaacatt tctgtaaagc tgaaaggaaa tatcatttat gatttattga tgggaaacag 111540
ttacaaattt tgagttactt gacaaacaga agggatgaaa tttatggcct agtgttgtgt 111600
tttcattctt aacccataag caaaaatctc tggaaaagta ccaatatcta gtaaaagaaa 111660
tattttttca caaaaagtat tttctatttt cccctcacct cttacctcgt ctcacctcaa 111720
agttcaagaa gcttaacttt gtgatcaaag gaaaatagta taattgaata tttgatacta 111780
tagaaatttg caactgtata agggcattat taaccttttg ctagtgatca gtttcctatc 111840
agggcagcca cataaaatta ggcatgacac tttaaaagaa aatgttgact cttaactttt 111900
cctcctctaa tgcttaattt taaaatagat ttaagcaact ttaaagacat tttcctgagc 111960
aactgcattt tgttttcatt ctgaatttaa tgagactctt t 112001

<210> SEQ ID NO 2
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 2
ctgctagcct ctggatttga 20

<210> SEQ ID NO 3
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 3
ccttccctga aggttcctcc 20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(20)
<223> OTHER INFORMATION: bases at these positions are RNA

```
<400> SEQUENCE: 4

cugcuagcct ctggauuuga                                                20


<210> SEQ ID NO 5
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 5

cugcuagccu cuggauuuga                                                20
```